(12) United States Patent
Ramachandran et al.

(10) Patent No.: US 11,774,459 B2
(45) Date of Patent: Oct. 3, 2023

(54) BIOMARKERS FOR DIAGNOSING NON-ALCOHOLIC STEATOHEPATITIS (NASH) OR HEPATOCELLULAR CARCINOMA (HCC)

(71) Applicant: Venn Biosciences Corporation, South San Francisco, CA (US)

(72) Inventors: Prasanna Ramachandran, Menlo Park, CA (US); Gege Xu, Redwood City, CA (US)

(73) Assignee: Venn Biosciences Corporation, South San Francisco, CA (US)

( * ) Notice: Subject to any disclaimer, the term of this patent is extended or adjusted under 35 U.S.C. 154(b) by 155 days.

(21) Appl. No.: 17/535,018

(22) Filed: Nov. 24, 2021

(65) Prior Publication Data
US 2022/0187317 A1    Jun. 16, 2022

Related U.S. Application Data

(60) Provisional application No. 63/251,021, filed on Sep. 30, 2021, provisional application No. 63/118,486, filed on Nov. 25, 2020.

(51) Int. Cl.
| | |
|---|---|
| *G01N 33/68* | (2006.01) |
| *G16B 40/20* | (2019.01) |
| *G16B 20/00* | (2019.01) |
| *G06N 3/08* | (2023.01) |
| *G01N 30/72* | (2006.01) |
| *G01N 30/02* | (2006.01) |

(52) U.S. Cl.
CPC ..... *G01N 33/6893* (2013.01); *G01N 30/7233* (2013.01); *G01N 33/6848* (2013.01); *G06N 3/08* (2013.01); *G16B 20/00* (2019.02); *G16B 40/20* (2019.02); *G01N 2030/027* (2013.01); *G01N 2440/38* (2013.01); *G01N 2800/085* (2013.01)

(58) Field of Classification Search
None
See application file for complete search history.

(56) References Cited

U.S. PATENT DOCUMENTS

| | | | |
|---|---|---|---|
| 2007/0099251 A1 | 5/2007 | Zhang et al. |
| 2015/0219672 A1 | 8/2015 | Meno et al. |
| 2019/0101544 A1 | 4/2019 | Danan-Leon et al. |
| 2020/0137273 A1 | 4/2020 | Ding et al. |
| 2020/0240996 A1 | 7/2020 | Danan-Leon et al. |

OTHER PUBLICATIONS

Sorino, P et al. Selecting the best machine learning algorithm to support the diagnosis of Non-Alcoholic Fatty Liver Disease: a meta learner study. *PLoS One*. Oct. 20, 2020, vol. 15, No. 10; pp. 1-12.
International Search Report and Written Opinion issued in corresponding International application PCT/US21/60776 dated Jun. 24, 2022.

*Primary Examiner* — Xiaoyun R Xu

(57) ABSTRACT

Embodiments described herein generally relate to technologies for analyzing peptide structures for diagnosing and/or treating a disease state advancing through a disease progression. A non-limiting example of a method relating to the technologies described in the subject application may include receiving peptide structure data corresponding to the biological sample obtained from the subject, identifying a peptide structure profile, and diagnosing a disease state within a disease progression. The example may further include generating a diagnosis output relating to the disease state. In at least some cases, the peptide structure profile may include glycosylated peptides, aglycosylated peptides, or both.

21 Claims, 23 Drawing Sheets
Specification includes a Sequence Listing.

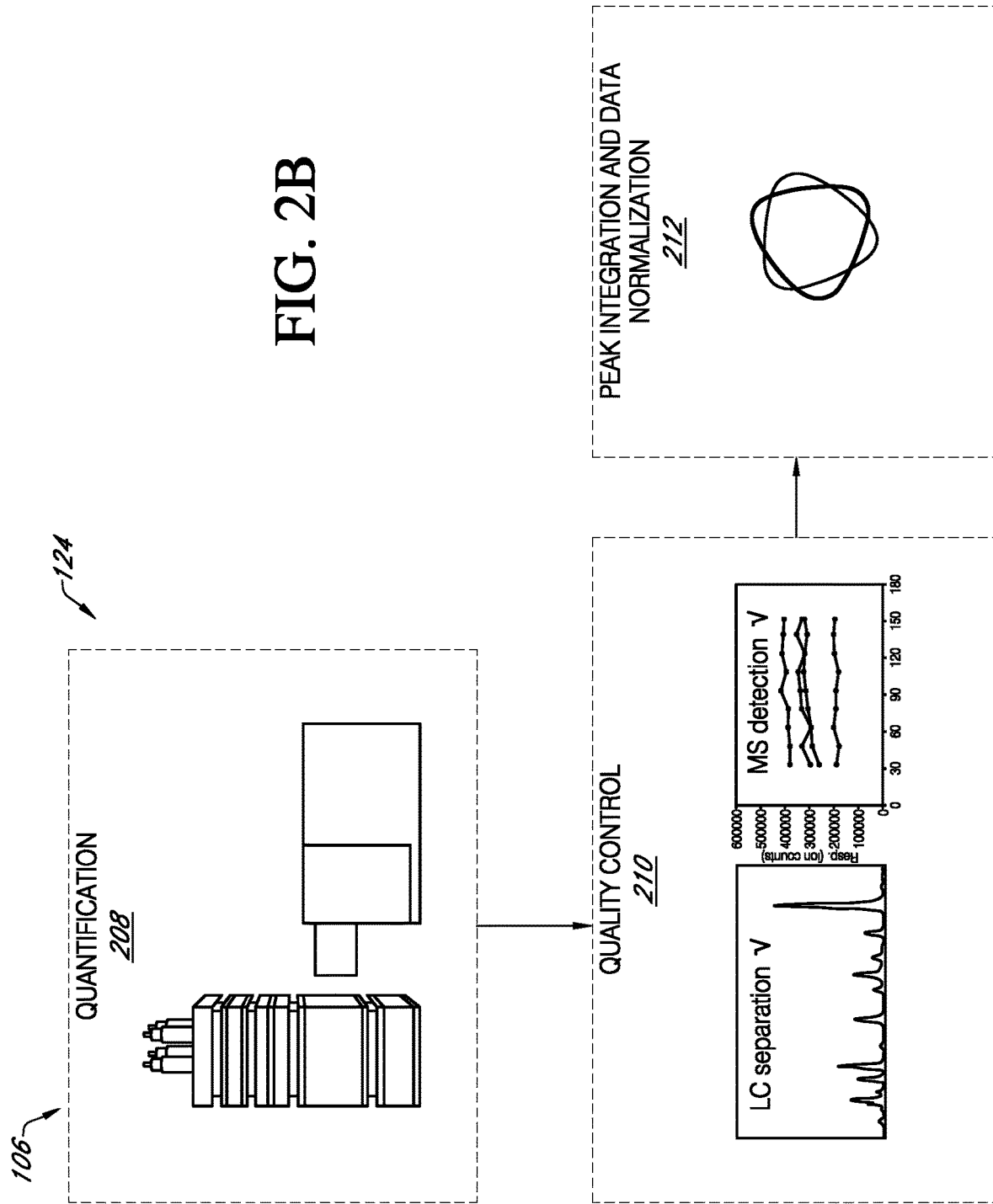

|  | Number of subjects | Male | Female |
|---|---|---|---|
| Control | 56 | 26 | 30 |
| NASH | 23 | 10 | 13 |
| HCC | 20 | 16 | 4 |

FIG. 11

| | Number of subjects | Male/Female |
|---|---|---|
| Control (liver-benign) | 28 | 16/12 |
| HCC | 28 | 20/8 |

FIG. 12

BIOMARKERS FOR DIAGNOSING NON-ALCOHOLIC STEATOHEPATITIS (NASH) OR HEPATOCELLULAR CARCINOMA (HCC)

CROSS-REFERENCE TO RELATED PATENT APPLICATIONS

This application claims priority to U.S. Provisional Patent Application No. 63/251,021, filed Sep. 30, 2021, and U.S. Provisional Patent Application No. 63/118,486, filed Nov. 25, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 31, 2022, is named 61375_6US01_SL.txt and is 112,789 bytes in size.

FIELD

The present disclosure generally relates to methods and systems for diagnosing and/or treating a state of a fatty liver disease (FLD) progression. More particularly, the present disclosure relates to analyzing quantification data for a set of peptide structures detected in a biological sample obtained from a subject for use in a diagnostic assessment of the subject's disease state (e.g., healthy, NASH, HCC) relating to a disease progression and/or treating the subject.

BACKGROUND

Protein glycosylation and other post-translational modifications play vital roles in virtually all aspects of human physiology. Unsurprisingly, faulty or altered protein glycosylation often accompanies various disease states. The identification of aberrant glycosylation provides opportunities for early detection, intervention, and treatment of affected subjects. Current biomarker identification methods, such as those developed in the fields of proteomics and genomics, can be used to detect indicators of certain diseases, such as cancer, and to differentiate certain types of cancer from other, non-cancerous diseases. However, the use of glycoproteomic analyses has not previously been used to successfully identify disease processes. Further, glycoproteomic analyses has not previously been used to successfully identify a disease state relating to a disease progression.

Glycoprotein analysis is fraught with challenges on several levels. For example, a single glycan composition in a peptide can contain a large number of isomeric structures due to different glycosidic linkages, branching patterns, and/or multiple monosaccharides having the same mass. In addition, the presence of multiple glycans that share the same peptide backbone can lead to assay signals from various glycoforms, lowering their individual abundances compared to aglycosylated peptides. Accordingly, the development of algorithms that can identify glycan structures on peptide fragments remains elusive.

In light of the above, there is a need for improved analytical methods that involve site-specific analysis of glycoproteins to obtain information about protein glycosylation patterns, which can in turn provide quantitative information that can be used to identify disease processes. The present disclosure addresses this and other needs by combining site-specific glycoprotein analysis with machine learning and advanced mass spectrometry instrumentation to quantitatively analyze peptide structures that are indicative of specific disease states, including, but not limited to, NASH and HCC.

Nonalcoholic fatty livery diseases (NAFLD or FLD) are byproducts of a global epidemic of obesity and metabolic syndrome. FLD progresses through stages of fat accumulation and inflammation to NASH, and a small percentage of NASH patients progress to HCC. Knowing an FLD stage of a patient with a high degree of accuracy would allow medical practitioners to customize treatment for individual patients and achieve better outcomes. However, current diagnostic techniques do not have the accuracy necessary to definitively predict the stage of FLD (e.g., whether a patient just has fat accumulation, NASH, or HCC). Thus, it may be desirable to have methods and systems capable of distinguishing between these and healthy states.

SUMMARY

In one or more embodiments, a method is provided for classifying a biological sample with respect to a plurality of states associated with fatty liver disease (FLD) progression. The method includes receiving peptide structure data corresponding to a set of glycoproteins in the biological sample obtained from a subject. Quantification data identified from the peptide structure data for a set of peptide structures is input into a machine learning model. The set of peptide structures includes at least one peptide structure identified from a plurality of peptide structures in Table 1. The quantification data is analyzed u sing the machine learning model to generate a disease indicator. A diagnosis output is generated based on the disease indicator that classifies the biological sample as evidencing a corresponding state of the plurality of states associated with the FLD progression.

In one or more embodiments, a method is provided for training a model to diagnose a subject with one of a plurality of states associated with fatty liver disease (FLD) progression. The method includes receiving quantification data for a panel of peptide structures for a plurality of subjects diagnosed with the plurality of states associated with the FLD progression. The quantification data comprises a plurality of peptide structure profiles for the plurality of subjects and identifies a corresponding state of the plurality of states for each peptide structure profile of the plurality of peptide structure profiles. A machine learning model is trained using the quantification data to determine which state of the plurality of states a biological sample from the subject corresponds.

In one or more embodiments, a method is provided for detecting a presence of one of a plurality of states associated with fatty liver disease (FLD) progression in a biological sample. The method includes receiving peptide structure data corresponding to a set of glycoproteins in the biological sample obtained from a subject. The peptide structure data is analyzed using a supervised machine learning model to generate a disease indicator based on at least 3 peptide structures selected from a group of peptide structures identified in Table 1. The presence of a corresponding state of the plurality of states associated with the FLD progression is detected in response to a determination that the disease indicator falls within a selected range associated with the corresponding state.

In one or more embodiments, a method is provided for classifying a biological sample as corresponding to one of a plurality of states associated with fatty liver disease (FLD)

progression. The method includes training a supervised machine learning model using training data. The training data comprises a plurality of peptide structure profiles for a plurality of training subjects and identifies a state of the plurality of states for each peptide structure profile of the plurality of peptide structure profiles. Peptide structure data corresponding to a set of glycoproteins in the biological sample obtained from a subject is received. Quantification data identified from the peptide structure data for a set of peptide structures is input into the supervised machine learning model that has been trained. The set of peptide structures includes at least one peptide structure identified in Table 1. The quantification data is analyzed using the supervised machine learning model to generate a score. A determination is made that the score falls within a selected range associated with a corresponding state of the plurality of states associated with the FLD progression. A diagnosis output is generated, where the diagnosis output indicates that the biological sample evidences the corresponding state. The plurality of states includes a non-alcoholic steatohepatitis (NASH) state, a hepatocellular carcinoma (HCC) state, and a non-NASH/HCC state.

In one or more embodiments, a method is provided for treating a non-alcoholic steatohepatitis (NASH) disorder in a patient to at least one of reduce, stall, or reverse a progression of the NASH disorder into hepatocellular carcinoma. The method includes receiving a biological sample from the patient. A quantity of each peptide structure identified in Table 1 in the biological sample is determined using a multiple reaction monitoring mass spectrometry (MRM-MS) system. The quantity of each peptide structure is analyzed using a machine learning model to generate a disease indicator. A diagnosis output is generated based on the disease indicator that classifies the biological sample as evidencing that the patient has the NASH disorder. Obeticholic acid (OCA) or a derivative thereof is administered to the patient. The administering comprises at least one of intravenous or oral administration in a range of 10-25 mg daily.

In one or more embodiments, a method is provided for treating a hepatocellular carcinoma (HCC) disorder in a patient. The method includes receiving a biological sample from the patient. A quantity of each peptide structure identified in Table 1 in the biological sample is determined using a multiple reaction monitoring mass spectrometry (MRM-MS) system. The quantity of each peptide structure is analyzed using a machine learning model to generate a disease indicator. A diagnosis output is generated based on the disease indicator that classifies the biological sample as evidencing that the patient has the HCC disorder. A treatment is administered, where the treatment includes at least one of: Sorafenib or a derivative thereof to the patient, the administering comprising at least one of intravenous or oral administration in a range of 775-825 mg daily; Lenvatinib or a derivative thereof to the patient, the administering comprising at least one of intravenous or oral administration in a range of 7.5-8.5 mg/day when the patient weighs <60 kg and 11.5-12.5 mg/day when the patient weighs >60 kg; Nivolumab or a derivative thereof to the patient, the administering comprising at least one of intravenous or oral administration in a range of 0.75-1.25 mg/kg; Regorafenib or a derivative thereof to the patient, the administering comprising oral administration in a range of 150-170 mg/day; Cabozantinib or a derivative thereof to the patient, the administering comprising at least one of intravenous or oral administration in a range of 50-70 mg/day; or Ramucirumab or a derivative thereof to the patient, the administering comprising at least one of intravenous or oral administration in a range of 8-12 mg/kg.

In one or more embodiments, a method is provided for designing a treatment for a subject diagnosed with a disease state associated with a fatty liver disease (FLD) progression. The method includes designing a therapeutic for treating the subject in response to determining that a biological sample obtained from the subject evidences the disease state using part or all of any one or more of the methods disclosed herein.

In one or more embodiments, a method is provided for planning a treatment for a subject diagnosed with a disease state associated with a fatty liver disease (FLD) progression, the method comprising generating a treatment plan for treating the subject in response to determining that a biological sample obtained from the subject evidences the disease state using part or all of any one or more of the methods disclosed herein.

In one or more embodiments, a method is provided for treating a subject diagnosed with a disease state associated with a fatty liver disease (FLD) progression, the method comprising administering to the subject a therapeutic to treat the subject based on determining that a biological sample obtained from the subject evidences the disease state using part or all of any one or more of the methods disclosed herein.

In one or more embodiments, a method is provided for treating a subject diagnosed with a disease state associated with a fatty liver disease (FLD) progression, the method comprising selecting a therapeutic to treat the subject based on determining that the subject is responsive to the therapeutic using part or all of any one or more of the methods disclosed herein.

In one or more embodiments, a method is provided for analyzing a set of peptide structures in a sample from a patient. The method includes (a) obtaining the sample from the patient; (b) preparing the sample to form a prepared sample comprising a set of peptide structures; (c) inputting the prepared sample into a monitoring mass spectrometry system using a liquid chromatography system; (d) detecting a set of productions associated with each peptide structure of the set of peptide structures; and (e) generating quantification data for the set of product ions using the monitoring mass spectrometry system. The set of peptide structures includes at least one peptide structure selected from peptide structures PS-1 to PS-53 identified in Table 4. The set of peptide structures includes a peptide structure that is characterized as having: (i) a precursor ion with a mass-charge (m/z) ratio within ±1.5 of the m/z ratio listed for the precursor ion in Table 4 as corresponding to the peptide structure; and (ii) a product ion having an m/z ratio within ±1.0 of the m/z ratio listed for the first product ion in Table 4 as corresponding to the peptide structure.

In one or more embodiments, a composition is provided, the composition comprising at least one of peptide structures PS-1 to PS-53 identified in Table 1.

In one or more embodiments, a composition is provided, the composition comprising a peptide structure or a production. The peptide structure or production comprises an amino acid sequence having at least 90% sequence identity to any one of SEQ ID NOS: 23-52, corresponding to peptide structures PS-1 to PS-53 in Table 1. The product ion is selected as one from a group consisting of product ions identified in Table 4 including product ions falling within an identified m/z range.

In one or more embodiments, a composition is provided, the composition comprising a glycopeptide structure selected as one from a group consisting of peptide structures PS-1 to PS-53 identified in Table 4. The glycopeptide structure comprises an amino acid peptide sequence identified in Table 5 as corresponding to the glycopeptide structure; and a glycan structure identified in Table 1 as corresponding to the glycopeptide structure in which the glycan structure is linked to a residue of the amino acid peptide sequence at a corresponding position identified in Table 1. The glycan structure has a glycan composition.

In one or more embodiments, a composition is provided, the composition comprising a peptide structure selected as one from a plurality of peptide structures identified in Table 1. The peptide structure has a monoisotopic mass identified as corresponding to the peptide structure in Table 1. The peptide structure comprises the amino acid sequence of SEQ ID NOs: 23-52 identified in Table 1 as corresponding to the peptide structure.

In one or more embodiments, a kit is provided, the kit comprising at least one agent for quantifying at least one peptide structure identified in Table 1 to carry out part or all of any one or more of the methods disclosed herein.

In one or more embodiments, a kit is provided, the kit comprising at least one of a glycopeptide standard, a buffer, or a set of peptide sequences to carry out part or all of any one or more of the methods disclosed herein. A peptide sequence of the set of peptide sequences is identified by a corresponding one of SEQ ID NOS: 23-52, defined in Table 1.

In one or more embodiments, a system comprises one or more data processors; and a non-transitory computer readable storage medium containing instructions which, when executed on the one or more data processors, cause the one or more data processors to perform part or all of any one or more of the methods disclosed herein.

In one or more embodiments, a computer-program product tangibly embodied in a non-transitory machine-readable storage medium is provided, including instructions configured to cause one or more data processors to perform part or all of any one or more of the methods disclosed herein.

BRIEF DESCRIPTION OF THE DRAWINGS

The present disclosure is described in conjunction with the appended figures:

FIG. 2B is a schematic diagram of data acquisition in accordance with one or more embodiments.

FIG. 11 is a table of the sample population used for the experiments in accordance with one or more embodiments.

FIG. 12 is a table of the sample population used for validation in accordance with one or more embodiments.

DETAILED DESCRIPTION

I. Overview

Figure 1:
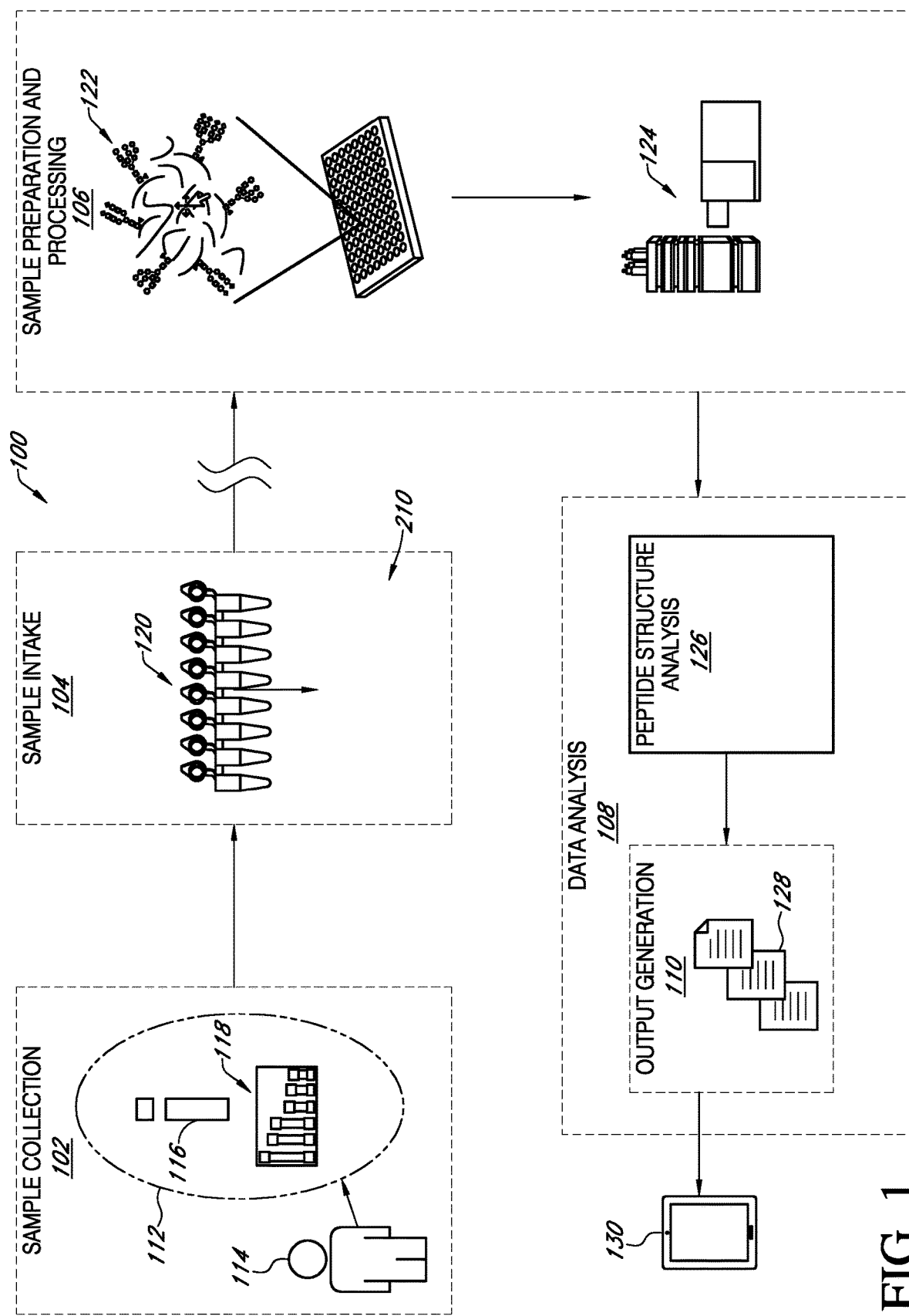
FIG. 1 is a schematic diagram of an exemplary workflow for the detection of peptide structures associated with a disease state for use in diagnosis and/or treatment in accordance with one or more embodiments.

The embodiments described herein recognize that glycoproteomics is an emerging field that can be used in the overall diagnosis and/or treatment of subjects with various types of diseases. Glycoproteomics aims to determine the positions, identities, and quantities of glycans and glycosylated proteins in a given sample (e.g., blood sample, cell, tissue, etc.). Protein glycosylation is one of the most common and most complex forms of post-translational protein modification, and can affect protein structure, conformation, and function. For example, glycoproteins may play crucial roles in important biological processes such as cell signaling, host-pathogen interactions, and immune response and disease. Glycoproteins may therefore be important to diagnosing different types of diseases. Glycoproteins may also be important to differentiating between stages within disease (e.g., the stages of FLD).

Although protein glycosylation provides useful information about cancer, other diseases, and stage determination of a disease analysis of protein glycosylation may be difficult as the glycan typically cannot be traced back to the protein site of origin with currently available methodologies. Glycoprotein analysis can be challenging in general for several reasons. For example, a single glycan composition in a peptide may contain a large number of isomeric structures because of different glycosidic linkages, branching, and many monosaccharides having the same mass. Further, the presence of multiple glycans that share the same peptide sequence may cause the mass spectrometry (MS) signal to split into various glycoforms, lowering their individual abundances compared to the peptides that are not glycosylated (aglycosylated peptides).

But to understand various disease conditions and disease progressions and to diagnose certain disease states more accurately, it may be important to perform analysis of glycoproteins and to identify not only the glycan but also the linking site (e.g., the amino acid residue of attachment) within the protein. Thus, there is a need to provide a method for site-specific glycoprotein analysis to obtain detailed information about protein glycosylation patterns which may be able to provide information about a disease state. This information can be used to distinguish the disease state from other states, diagnose a subject as having or not having the disease state, determine a likelihood that a subject has the disease state, or a combination thereof. Such analysis may be useful in distinguishing between, for example, without limitation, two or more of a non-alcoholic steatohepatitis (NASH) state, a hepatocellular carcinoma (HCC) state, and a non-NASH/HCC state (which may include at least one of a non-alcoholic FLD disease state, a control state, a healthy state, a liver disease-free state, or a benign hepatic mass state).

Accordingly, the embodiments described herein provide various methods and systems for analyzing proteins in subjects and, in particular, glycoproteins. In one or more embodiments, a machine learning model is trained to analyze peptide structure data and generate a disease indicator that provides information relating to one or more diseases. For example, in various embodiments, the peptide structure data comprises quantification metrics (e.g., abundance or concentration data) for peptide structures. A peptide structure may be defined by an aglycosylated peptide sequence (e.g., a peptide or peptide fragment of a larger parent protein) or a glycosylated peptide sequence. A glycosylated peptide sequence (also referred to as a glycopeptide structure) may be a peptide sequence having a glycan structure that is attached to a linking site (e.g., an amino acid residue) of the peptide sequence, which may occur via, for example, a particular atom of the amino acid residue). Non-limiting examples of glycosylated peptides include N-linked glycopeptides and O-linked glycopeptides.

The embodiments described herein recognize that the abundance of selected peptide structures in a biological sample obtained from a subject may be used to determine the likelihood of that subject having a particular disease state (e.g., stage of FLD).

Analyzing the abundance of peptide sequences and glycosylated peptide sequences in a biological sample may provide a more accurate way in which to distinguish the state of progression within FLD. This type of peptide structure analysis may be more conducive to generating accurate diagnoses as compared to glycoprotein analysis that focuses on analyzing glycoproteins that are too large to be resolved via mass spectrometry. Further, with glycoproteins, there may be too many potential proteoforms to consider. Still further, analysis of peptide structure data in the manner described by the various embodiments herein may be more conducive to generating accurate diagnoses as compared to glycomic analysis that provides little to no information about what proteins and to which amino acid residue sites various gly can structures attach.

The description below provides exemplary implementations of the methods and systems described herein for the research, diagnosis, and/or treatment (e.g., designing planning, and/or manufacturing of a treatment) of a disease state (e.g., a NASH state, an HCC state, etc.) associated with FLD. Descriptions and examples of various terms, as used herein, are provided in Section II below.

II. Exemplary Descriptions of Terms

The term "ones" means more than one.

As used herein, the term "plurality" may be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "amino acid," as used herein, generally refers to any organic compound that includes an amino group (e.g., —NH2), a carboxyl group (—COOH), and a side chain group (R) which varies based on a specific amino acid. Amino acids can be linked using peptide bonds.

The term "alkylation," as used herein, generally refers to the transfer of an alkyl group from one molecule to another. In various embodiments, alkylation is used to react with reduced cysteines to prevent the re-formation of disulfide bonds after reduction has been performed.

The term "linking site" or "glycosylation site" as used herein generally refers to the location where a sugar molecule of a glycan or glycan structure is directly bound (e.g., covalently bound) to an amino acid of a peptide, a polypeptide, or a protein. For example, the linking site may be an amino acid residue and a glycan structure may be linked via an atom of the amino acid residue. Non-limiting examples of types of glycosylation can include N-linked glycosylation, O-linked glycosylation, C-linked glycosylation, S-linked glycosylation, and glycation.

The terms "biological sample," "biological specimen," or "biospecimen" as used herein, generally refers to a specimen taken by sampling so as to be representative of the source of the specimen, typically, from a subject. A biological sample can be representative of an organism as a whole, specific tissue, cell type, or category or sub-category of interest. The biological sample can include a macromolecule. The biological sample can include a small molecule. The biological sample can include a virus. The biological sample can include a cell or derivative of a cell. The biological sample can include an organelle. The biological sample can include a cell nucleus. The biological sample can include a rare cell from a population of cells. The biological sample can include any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological sample can include a constituent of a cell. The biological sample can include nucleotides (e.g., ssDNA, dsDNA, RNA), organelles, amino acids, peptides, proteins, carbohydrates, glycoproteins, or any combination thereof. The biological sample can include a matrix (e.g., a gel or polymer matrix) comprising a cell or one or more constituents from a cell (e.g., cell bead), such as DNA, RNA, organelles, proteins, or any combination thereof, from the cell. The biological sample may be obtained from a tissue of a subject. The biological sample can include a hardened cell. Such hardened cells may or may not include a cell wall or cell membrane. The biological sample can include one or more constituents of a cell but may not include other constituents of the cell. An example of such constituents may include a nucleus or an organelle. The biological sample may include a live cell. The live cell can be capable of being cultured.

The term "biomarker," as used herein, generally refers to any measurable substance taken as a sample from a subject whose presence is indicative of some phenomenon. Non-limiting examples of such phenomenon can include a disease state, a condition, or exposure to a compound or environmental condition. In various embodiments described herein, biomarkers may be used for diagnostic purposes (e.g., to diagnose a disease state, a health state, an asymptomatic state, a symptomatic state, etc.). The term "biomarker" may be used interchangeably with the term "marker."

The term "denaturation," as used herein, generally refers to any molecule that loses quaternary structure, tertiary structure, and secondary structure which is present in their native state. Non-limiting examples include proteins or nucleic acids being exposed to an external compound or environmental condition such as acid, base, temperature, pressure, radiation, etc.

The term "denatured protein," as used herein, generally refers to a protein that loses quaternary structure, tertiary structure, and secondary structure which is present in their native state.

The terms "digestion" or "enzymatic digestion," as used herein, generally refer to breaking apart a polymer (e.g., cutting a polypeptide at a cut site). Proteins may be digested in preparation for mass spectrometry using trypsin digestion protocols. Proteins may be digested using other proteases in preparation for mass spectrometry if access is limited to cleavage sites.

The terms "immune checkpoint inhibitor therapeutic" and "immune checkpoint inhibitor drug," as used herein, generally refer to drugs or therapeutics that can target immune checkpoint molecules (e.g., molecules on immune cells that need to be activated (or inactivated) to start an immune response). Non-limiting examples of immune checkpoint inhibitor therapeutics can include pembrolizumab, nivolumab, and cemiplimab.

The term "disease progression," as used herein, refers to a progression of a disease from no disease or a less advanced (e.g., severe) form of disease to a more advanced (e.g, severe) form of the disease. A disease progression may include any number of stages of the disease.

The term "disease state" as used herein, generally refers to a condition that affects the structure or function of an organism. Non-limiting examples of causes of disease states may include pathogens, immune system dysfunctions, cell damage caused by aging, cell damage caused by other factors (e.g., trauma and cancer). Disease states can include, for example, stages of a disease progression. For example, for FLD, the progression may be from healthy to a stage of fat accumulation and inflammation (Fatty Liver), to non-alcoholic steatohepatitis (NASH), to fibrosis, and to cirrhosis. In some cases, the progression may advance from NASH to hepatocellular carcinoma (HCC). Disease states can include any state of a disease whether symptomatic or asymptomatic. Disease states can cause minor, moderate, or severe disruptions in the structure or function of a subject.

The terms "glycan" or "polysaccharide" as used herein, both generally refer to a carbohydrate residue of a glycoconjugate, such as the carbohydrate portion of a glycopeptide, glycoprotein, glycolipid, or proteoglycan. Glycans can include monosaccharides.

The term "glycopeptide" or "glycopolypeptide" as used herein, generally refer to a peptide or polypeptide comprising at least one glycan residue. In various embodiments, glycopeptides comprise carbohydrate moieties (e.g., one or more glycans) covalently attached to a side chain (i.e. R group) of an amino acid residue.

The term "glycoprotein," as used herein, generally refers to a protein having at least one glycan residue bonded thereto. In some examples, a glycoprotein is a protein with at least one oligosaccharide chain covalently bonded thereto. Examples of glycoproteins, include but are not limited to apolipoprotein C-III (APOC3), alpha-1-antichymotrypsin (AACT), afamin (AFAM), alpha-1-acid glycoprotein 1 & 2 (AGP12), apolipoprotein B-100 (APOB), apolipoprotein D (APOD), complement C1s subcomponent (C1 S), calpain-3 (CAN3), clusterin (CLUS), complement component C8AChain (CO8A), alpha-2-HS-glycoprotein (FETUA), haptoglobin (HPT), immunoglobulin heavy constant gamma 1 (IgG1), immunoglobulin J chain (IgJ), plasma kallikrein (KLKB1), serum paraoxonase/arylesterase 1 (PON1), prothrombin (THRB), serotransferrin (TRFE), protein unc-13 homologA (UN13A), and zinc-alpha-2-glycoprotein (ZA2G). A glycopeptide, as used herein, refers to a fragment of a glycoprotein, unless specified otherwise to the contrary.

The term "liquid chromatography," as used herein, generally refers to a technique used to separate a sample into parts. Liquid chromatography can be used to separate, identify, and quantify components.

The term "mass spectrometry," as used herein, generally refers to an analytical technique used to identify molecules. In various embodiments described herein, mass spectrometry can be involved in characterization and sequencing of proteins.

The term "m/z" or "mass-to-charge ratio" as used herein, generally refers to an output value from a mass spectrometry instrument. In various embodiments, m/z can represent a relationship between the mass of a given ion and the number of elementary charges that it carries. The "m" in m/z stands for mass and the "z" stands for charge. In some embodiments, m/z can be displayed on an x-axis of a mass spectrum.

The term "peptide," as used herein, generally refers to amino acids linked by peptide bonds. Peptides can include amino acid chains between 10 and 50 residues. Peptides can include amino acid chains shorter than 10 residues, including, oligopeptides, dipeptides, tripeptides, and tetrapeptides. Peptides can include chains longer than 50 residues and may be referred to as "polypeptides" or "proteins."

The terms "protein" or "polypeptide" or "peptide" may be used interchangeably herein and generally refer to a molecule including at least three amino acid residues. Proteins can include polymer chains made of amino acid sequences linked together by peptide bonds. Proteins may be digested in preparation for mass spectrometry using trypsin digestion protocols. Proteins may be digested using other proteases in preparation for mass spectrometry if access is limited to cleavage sites.

The term "peptide structure," as used herein, generally refers to peptides or a portion thereof or glycopeptides or a portion thereof. In various embodiments described herein, a peptide structure can include any molecule comprising at least two amino acids in sequence.

The term "reduction," as used herein, generally refers to the gain of an electron by a substance. In various embodiments described herein, a sugar can directly bind to a protein, thereby, reducing the amino acid to which it binds. Such reducing reactions can occur in glycosylation. In various embodiments, reduction may be used to break disulfide bonds between two cysteines.

The term "sample," as used herein, generally refers to a sample from a subject of interest and may include a biological sample of a subject. The sample may include a cell sample. The sample may include a cell line or cell culture sample. The sample can include one or more cells. The sample can include one or more microbes. The sample may include a nucleic acid sample or protein sample. The sample may also include a carbohydrate sample or a lipid sample. The sample may be derived from another sample. The sample may include a tissue sample, such as a biopsy, core biopsy, needle aspirate, or fine needle aspirate. The sample may include a fluid sample, such as a blood sample, urine sample, or saliva sample. The sample may include a skin sample. The sample may include a cheek swab. The sample may include a plasma or serum sample. The sample may include a cell-free or cell free sample. A cell-free sample may include extracellular polynucleotides. The sample may originate from blood, plasma, serum, urine, saliva, mucosal excretions, sputum, stool, or tears. The sample may originate from red blood cells or white blood cells. The sample may originate from feces, spinal fluid, CNS fluid, gastric fluid, amniotic fluid, cyst fluid, peritoneal fluid, marrow, bile, other body fluids, tissue obtained from a biopsy, skin, or hair.

The term "sequence," as used herein, generally refers to a biological sequence including one-dimensional monomers that can be assembled to generate a polymer. Non-limiting examples of sequences include nucleotide sequences (e.g., ssDNA, dsDNA, and RNA), amino acid sequences (e.g., proteins, peptides, and polypeptides), and carbohydrates (e.g., compounds including $C_m(H_2O)_n$).

The term "subject," as used herein, generally refers to an animal, such as a mammal (e.g., human) or avian (e.g., bird), or other organism, such as a plant. For example, the subject can include a vertebrate, a mammal, a rodent (e.g., a mouse), a primate, a simian, or a human. Animals may include, but are not limited to, farm animals, sport animals, and pets. A subject can include a healthy or asymptomatic individual, an individual that has or is suspected of having a disease (e.g., cancer) or a pre-disposition to the disease, and/or an individual that needs therapy or suspected of needing therapy. A subject can be a patient. A subject can include a microorganism or microbe (e.g., bacteria, fungi, archaea, viruses).

As used herein, a "model" may include one or more algorithms, one or more mathematical techniques, one or more machine learning algorithms, or a combination thereof.

As used herein, "machine learning" may be the practice of using algorithms to parse data, learn from it, and then make a determination or prediction about something in the world. Machine learning uses algorithms that can learn from data without relying on rules-based programming. A machine learning algorithm may include a parametric model, a non-parametric model, a deep learning model, a neural network, a linear discriminant analysis model, a quadratic discriminant analysis model, a support vector machine, a random forest algorithm, a nearest neighbor algorithm, a combined discriminant analysis model, a k-means clustering algorithm, a supervised model, an unsupervised model, logistic regression model, a multivariable regression model, a penalized multivariable regression model, or another type of model.

As used herein, an "artificial neural network" or "neural network" (NN) may refer to mathematical algorithms or computational models that mimic an interconnected group of artificial nodes or neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways: when it is being trained it is in training mode and when it puts what it has learned into practice it is in inference (or prediction) mode. Neural networks learn through a feedback process (e.g., backpropagation) which allows the network to adjust the weight factors (modifying its behavior) of the individual nodes in the intermediate hidden layers so that the output matches the outputs of the training data. In other words, a neural network learns by being fed training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), or another type of neural network.

As used herein, a "target glycopeptide analyte," may refer to a peptide structure (e.g., glycosylated or aglycosylated/non-glycosylated), a fraction of a peptide structure, a sub-structure (e.g., a glycan or a glycosylation site) of a peptide structure, a product of one or more of the above listed structures and sub-structures, associated detection molecules (e.g., signal molecule, label, or tag), or an amino acid sequence that can be measured by mass spectrometry.

As used herein, a "peptide data set," may be used interchangeably with "peptide structure data" and can refer to any data of or relating to a peptide from a resulting mass spectrometry run. A peptide data set can comprise data obtained from a sample or biological sample using mass spectrometry. A peptide dataset can comprise data relating to a NGEP external standard, data relating to an internal standard, and data relating to a target glycopeptide analyte of a sample. A peptide data set can result from analysis originating from a single run. In some embodiments, the peptide data set can include raw abundance and mass to charge ratios for one or more peptides.

As used herein, a "non-glycosylated endogenous peptide" ("NGEP"), which may also be referred to as an aglycosylated peptide, may refer to a peptide structure that does not comprise a glycan molecule. In various embodiments, an NGEP and a target glycopeptide analyte can originate from the same subject. In various embodiments, an NGEP can be labeled with an isotope in preparation for mass spectrometry analysis.

As used herein, a "transition," may refer to or identify a peptide structure. In some embodiments, a transition can refer to the specificpair of m/z values associated with a precursor ion and a product or fragment ion.

As used herein, a "non-glycosylated endogenous peptide" ("NGEP") may refer to a peptide structure that does not comprise a glycan molecule. In various embodiments, an NGEP and a target glycopeptide analyte may be derived from the same protein sequence. In some embodiments, the NGEP and the target glycopeptide analyte may be derived from or include the same peptide sequence. In various embodiments, a NGEP can be labeled with an isotope in preparation for mass spectrometry analysis.

As used herein, an "abundance value" may refer to "abundance" ora quantitative value associated with abundance.

As used herein, "abundance," may refer to a quantitative value generated using mass spectrometry. In various embodiments, the quantitative value may relate to an amount of a particular peptide structure (e.g., biomarker) present in a biological sample. In some embodiments, the amount may be in relation to other structures present in the sample (e.g., relative abundance). In some embodiments, the quantitative value may comprise an amount of an ion produced using mass spectrometry. In some embodiments, the quantitative value may be associated with an m/z value (e.g., abundance on x-axis and m/z on y-axis). In other embodiments, the quantitative value may be expressed in atomic mass units.

As used herein, "relative abundance," may refer to a comparison of two or more abundances. In various embodiments, the comparison may comprise comparing one peptide structure to a total number of peptide structures. In some embodiments, the comparison may comprise comparing one peptide glycoform (e.g., two identical peptides differing by one or more glycans) to a set of peptide glycoforms. In some embodiments, the comparison may comprise comparing a number of ions having a particular m/z ratio by a total number of ions detected. In various embodiments, a relative abundance can be expressed as a ratio. In other embodiments, a relative abundance can be expressed as a percentage. Relative abundance can be presented on a y-axis of a mass spectrum plot.

As used herein, an "internal standard," may refer to something that can be contained (e.g., spiked-in) in the same sample as a target glycopeptide analyte undergoing mass spectrometry analysis. Internal standards can be used for calibration purposes. Additionally, internal standards can be used in the systems and method described herein. In some aspects, an internal standard can be selected based on similarity m/z and or retention times and can be a "surrogate" if a specific standard is too costly or unavailable. Internal standards can be heavy labeled or non-heavy labeled.

III. Overview of Exemplary Workflow

FIG. 1 is a schematic diagram of an exemplary workflow 100 for the detection of peptide structures associated with a disease state for use in diagnosis and/or treatment in accordance with one or more embodiments. Workflow 100 may include various operations including, for example, sample collection 102, sample intake 104, sample preparation and processing 106, data analysis 108, and output generation 110.

Sample collection 102 may include, for example, obtaining a biological sample 112 of one or more subjects, such as subject 114. Biological sample 112 may take the form of a specimen obtained via one or more sampling methods. Biological sample 112 may be representative of subject 114 as a whole or of a specific tissue, cell type, or other category or sub-category of interest. Biological sample 112 may be obtained in any of a number of different ways. In various embodiments, biological sample 112 includes whole blood sample 116 obtained via a blood draw. In other embodiments, biological sample 112 includes set of aliquoted samples 118 that includes, for example, a serum sample, a plasma sample, a blood cell (e.g., white blood cell (WBC), red blood cell (RBC) sample, another type of sample, or a combination thereof. Biological samples 112 may include nucleotides (e.g., ssDNA, dsDNA, RNA), organelles, amino acids, peptides, proteins, carbohydrates, glycoproteins, or any combination thereof.

In various embodiments, a single run can analyze a sample (e.g., the sample including a peptide analyte), an external standard (e.g., an NGEP of a serum sample), and an internal standard. As such, abundance values (e.g., abundance or raw abundance) for the external standard, the internal standard, and target glycopeptide analyte can be determined by mass spectrometry in the same run.

In various embodiments, external standards may be analyzed prior to analyzing samples. In various embodiments, the external standards can be run independently between the samples. In some embodiments, external standards can be analyzed after every 1, 2, 3, 4, 5, 6, 7, 8, 9, 10, 11, 12, 13, 14, 15, 16, 17, 18, 19, 20, or more experiments. In various embodiments, external standard data can be used in some or all of the normalization systems and methods described herein. In additional embodiments, blank samples may be processed to prevent column fouling.

Sample intake 104 may include one or more various operations such as, for example, aliquoting, registering, processing, storing, thawing, and/or other types of operations. In one or more embodiments, when biological sample 112 includes whole blood sample 116, sample intake 104 includes aliquoting whole blood sample 116 to form a set of aliquoted samples that can then be sub-aliquoted to form set of samples 120.

Sample preparation and processing 106 may include, for example, one or more operations to form set of peptide structures 122. In various embodiments, set of peptide structures 122 may include various fragments of unfolded proteins that have undergone digestion and may be ready for analysis.

Further, sample preparation and processing 106 may include, for example, data acquisition 124 based on set of peptide structures 122. For example, data acquisition 124 may include use of, for example, but is not limited to, a liquid chromatography/mass spectrometry (LC/MS) system.

Data analysis 108 may include, for example, peptide structure analysis 126. In some embodiments, data analysis 108 also includes output generation 110. In other embodiments, output generation 110 may be considered a separate operation from data analysis 108. Output generation 110 may include, for example, generating final output 128 based on the results of peptide structure analysis 126. In various embodiments, final output 128 may be used for determining the research, diagnosis, and/or treatment of a state associated with fatty liver disease.

In various embodiments, final output 128 is comprised of one or more outputs. Final output 128 may take various forms. For example, final output 128 may be a report that includes, for example, a diagnosis output, a treatment output (e.g., a treatment design output, a treatment plan output, or combination thereof), analyzed data (e.g., relativized and normalized) or combination thereof. In some embodiments, the report can comprise a target glycopeptide analyte concentration as a function of the NGEP concentration value and the normalized abundance value. In some embodiments, final output 128 may be an alert (e.g., a visual alert, an audible alert, etc.), a notification (e.g., a visual notification, an audible notification, an email notification, etc.), an email output, or a combination thereof. In some embodiments, final output 128 may be sent to remote system 130 for processing. Remote system 130 may include, for example, a computer system, a server, a processor, a cloud computing platform, cloud storage, a laptop, a tablet, a smartphone, some other type of mobile computing device, or a combination thereof.

In other embodiments, workflow 100 may optionally exclude one or more of the operations described herein and/or may optionally include one or more other steps or operations other than those described herein (e.g., in addition to and/or instead of those described herein). Accordingly, workflow 100 may be implemented in any of a number of different ways for use in the research, diagnosis, and/or treatment of, for example, FLD.

IV. Detection and Quantification of Peptide Structures

Figure 2A:
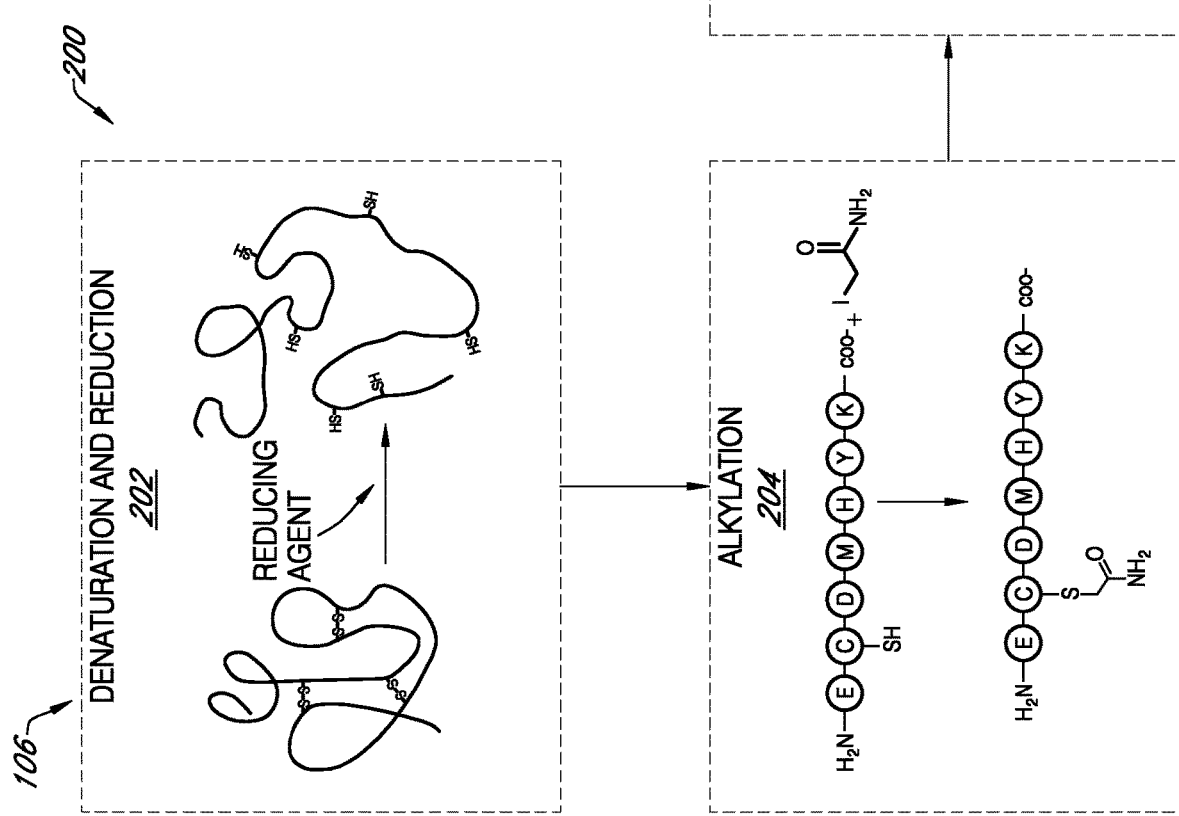
FIG. 2A is a schematic diagram of a preparation workflow in accordance with one or more embodiments. Figure discloses SEQ ID NOS 53 and 54, respectively, in order of appearance.

FIGS. 2A and 2B are schematic diagrams of a workflow for sample preparation and processing 106 in accordance with one or more embodiments. FIGS. 2A and 2B are described with continuing reference to FIG. 1. Sample preparation and processing 106 may include, for example, preparation workflow 200 shown in FIG. 2A and data acquisition 124 shown in FIG. 2B.

IV.A. Sample Preparation and Processing

FIG. 2A is a schematic diagram of preparation workflow 200 in accordance with one or more embodiments. Preparation workflow 200 may be used to prepare a sample, such as a sample of set of samples 120 in FIG. 1, for analysis via data acquisition 124. For example, this analysis may be performed via mass spectrometry (e.g., LC-MS). In various embodiments, preparation workflow 200 may include denaturation and reduction 202, alkylation 204, and digestion 206.

In general, polymers, such as proteins, in their native form, can fold to include secondary, tertiary, and/or other higher order structures. Such higher order structures may functionalize proteins to complete tasks (e.g., enable enzymatic activity) in a subject. Further, such higher order structures of polymers may be maintained via various interactions between side chains of amino acids within the polymers. Such interactions can include ionic bonding hydrophobic interactions, hydrogen bonding, and disulfide linkages between cysteine residues. However, when using analytic systems and methods, including mass spectrometry, unfolding such polymers (e.g., peptide/protein molecules) may be desired to obtain sequence information. In some embodiments, unfolding a polymer may include denaturing the polymer, which may include, for example, linearizing the polymer.

In one or more embodiments, denaturation and reduction 202 can be used to disrupt higher order structures (e.g., secondary, tertiary, quaternary, etc.) of one or more proteins (e.g, polypeptides and peptides) in a sample (e.g., one of set of samples 120 in FIG. 1). Denaturation and reduction 202 includes, for example, a denaturation procedure and a reduction procedure. In some embodiments, the denaturation procedure may be performed using, for example, thermal denaturation, where heat is used as a denaturing agent. The thermal denaturation can disrupt ionic bonding, hydrophobic interactions, and/or hydrogen bonding.

In one or more embodiments, the denaturation procedure may include using one or more denaturing agents, temperature (e.g., heat), or both. These one or more denaturing agents may include, for example, but are not limited to, any number of chaotropic salts (e.g., urea, guanidine), surfactants (e.g., sodium dodecyl sulfate (SDS), beta octyl glucoside, Triton X-100), or combination thereof. In some cases, such denaturing agents may be used in combination with heat when sample preparation workflow further includes a cleanup procedure.

The resulting one or more denatured (e.g., unfolded, linearized) proteins may then undergo further processing in preparation of analysis. For example, a reduction procedure may be performed in which one or more reducing agents are applied. In various embodiments, a reducing agent can produce an alkaline pH. A reducing agent may take the form of, for example, without limitation, dithiothreitol (DTT), tris(2-carboxyethyl)phosphine (TCEP), or some other reducing agent. The reducing agent may reduce (e.g., cleave) the disulfide linkages between cysteine residues of the one or more denatured proteins to form one or more reduced proteins.

In various embodiments, the one or more reduced proteins resulting from denaturation and reduction 202 may undergo a process to prevent the reformation of disulfide linkages between, for example, the cysteine residues of the one or more reduced proteins. This process may be implemented using alkylation 204 to form one or more alkylated proteins. For example, alkylation 204 may be used to add an acetamide group to a sulfur on each cysteine residue to prevent disulfide linkages from reforming. In various embodiments, an acetamide group can be added by reacting one or more alkylating agents with a reduced protein. The one or more alkylating agents may include, for example, one or more acetamide salts. An alkylating agent may take the form of, for example, iodoacetamide (IAA), 2-chloroacetamide, some other type of acetamide salt, or some other type of alkylating agent.

In some embodiments, alkylation 204 may include a quenching procedure. The quenching procedure may be performed using one or more reducing agents (e.g., one or more of the reducing agents described above).

In various embodiments, the one or more alkylated proteins formed via alkylation 204 can then undergo digestion 206 in preparation for analysis (e.g., mass spectrometry analysis). Digestion 206 of a protein may include cleaving the protein at or around one or more cleavage sites (e.g., site 205 which may be one or more amino acid residues). For example, without limitation, an alkylated protein may be cleaved at the carboxyl side of the lysine or arginine residues. This type of cleavage may break the protein into various segments, which include one or more peptide structures (e.g., glycosylated or aglycosylated).

In various embodiments, digestion 206 is performed using one or more proteolysis catalysts. For example, an enzyme can be used in digestion 206. In some embodiments, the enzyme takes the form of trypsin. In other embodiments, one or more other types of enzymes (e.g., proteases) may be used in addition to or in place of trypsin. These one or more other enzymes include, but are not limited to, LysC, LysN, AspN, GluC, and ArgC. In some embodiments, digestion 206 may be performed using tosyl phenylalanyl chloromethyl ketone (TPCK)-treated trypsin, one or more engineered forms of trypsin, one or more other formulations of trypsin, or a combination thereof. In some embodiments, digestion 206 may be performed in multiple steps, with each involving the use of one or more digestion agents. For example, a secondary digestion, tertiary digestion, etc. may be performed. In one or more embodiments, trypsin is used to digest serum samples. In one or more embodiments, trypsin/LysC cocktails are used to digest plasma samples.

In some embodiments, digestion 206 further includes a quenching procedure. The quenching procedure may be performed by acidifying the sample (e.g., to a pH<3). In some embodiments, formic acid may be used to perform this acidification.

In various embodiments, preparation workflow 200 further includes post-digestion procedure 207. Post-digestion procedure 207 may include, for example, a cleanup procedure. The cleanup procedure may include, for example, the removal of unwanted components in the sample that results from digestion 206. For example, unwanted components may include, but are not limited to, inorganic ions, surfactants, etc. In some embodiments, post-digestion procedure 207 further includes a procedure for the addition of heavy-labeled peptide internal standards.

Although preparation workflow 200 has been described with respect to a sample created or taken from biological sample 112 that is blood-based (e.g., a whole blood sample, a plasma sample, a serum sample, etc.), sample preparation workflow 200 may be similarly implemented for other types of samples (e.g., tears, urine, tissue, interstitial fluids, sputum, etc.) to produce set of peptides structures 122.

IV.B. Peptide Structure Identification and Quantitation

FIG. 2B is a schematic diagram of data acquisition 124 in accordance with one or more embodiments. In various embodiments, data acquisition 124 can commence following sample preparation 200 described in FIG. 2A. In various embodiments, data acquisition 124 can comprise quantification 208, quality control 210, and peak integration and normalization 212.

In various embodiments, targeted quantification 208 of peptides and glycopeptides can incorporate use of liquid chromatography-mass spectrometry LC/MS instrumentation. For example, LC-MS/MS, or tandem MS may be used. In general, LC/MS (e.g., LC-MS/MS) can combine the physical separation capabilities of liquid chromatograph (LC) with the mass analysis capabilities of mass spectrometry (MS). According to some embodiments described herein, this technique allows for the separation of digested peptides to be fed from the LC column into the MS ion source through an interface.

In various embodiments, any LC/MS device can be incorporated into the workflow described herein. In various embodiments, an instrument or instrument system suited for identification and targeted quantification 208 may include, for example, a Triple Quadrupole LC/MS™. In various embodiments, targeted quantification 208 is performed using multiple reaction monitoring mass spectrometry (MRM-MS).

In various embodiments described herein, identification of a particular protein or peptide and an associated quantity can be assessed. In various embodiments described herein, identification of a particular glycan and an associated quantity can be assessed. In various embodiments described herein, particular glycans can be matched to a glycosylation site on a protein or peptide and the abundance values measured.

In some cases, targeted quantification 208 includes using a specific collision energy associated for the appropriate fragmentation to consistently see an abundant product ion. Glycopeptide structures may have a lower collision energy than aglycosylated peptide structures. When analyzing a sample that includes glycopeptide structures, the source voltage and gas temperature may be lowered as compared to generic proteomic analysis.

In various embodiments, quality control 210 procedures can be put in place to optimize data quality. In various embodiments, measures can be put in place allowing only errors within acceptable ranges outside of an expected value. In various embodiments, employing statistical models (e.g., using Westgard rules) can assist in quality control 210. For example, quality control 210 may include, for example, assessing the retention time and abundance of representative peptide structures (e.g., glycosylated and/or aglycosylated) and spiked-in internal standards, in either every sample, or in each quality control sample (e.g., pooled serum digest).

Peak integration and normalization 212 may be performed to process the data that has been generated and transform the data into a format for analysis. For example, peak integration and normalization 212 may include converting abundance data for various product ions that were detected for a selected peptide structure into a single quantification metric (e.g, a relative quantity, an adjusted quantity, a normalized quantity, a relative concentration, an adjusted concentration, a normalized concentration, etc.) for that peptide structure. In some embodiments, peak integration and normalization 212 may be performed using one or more of the techniques described in U.S. Patent Publication No. 2020/0372973A1 and/or US Patent Publication No. 2020/0240996A1, the disclosures of which are incorporated by reference herein in their entireties.

V. Exemplary System for Peptide Structure Data Analysis

V.A. Analysis System for Peptide Structure Data Analysis

Figure 3:
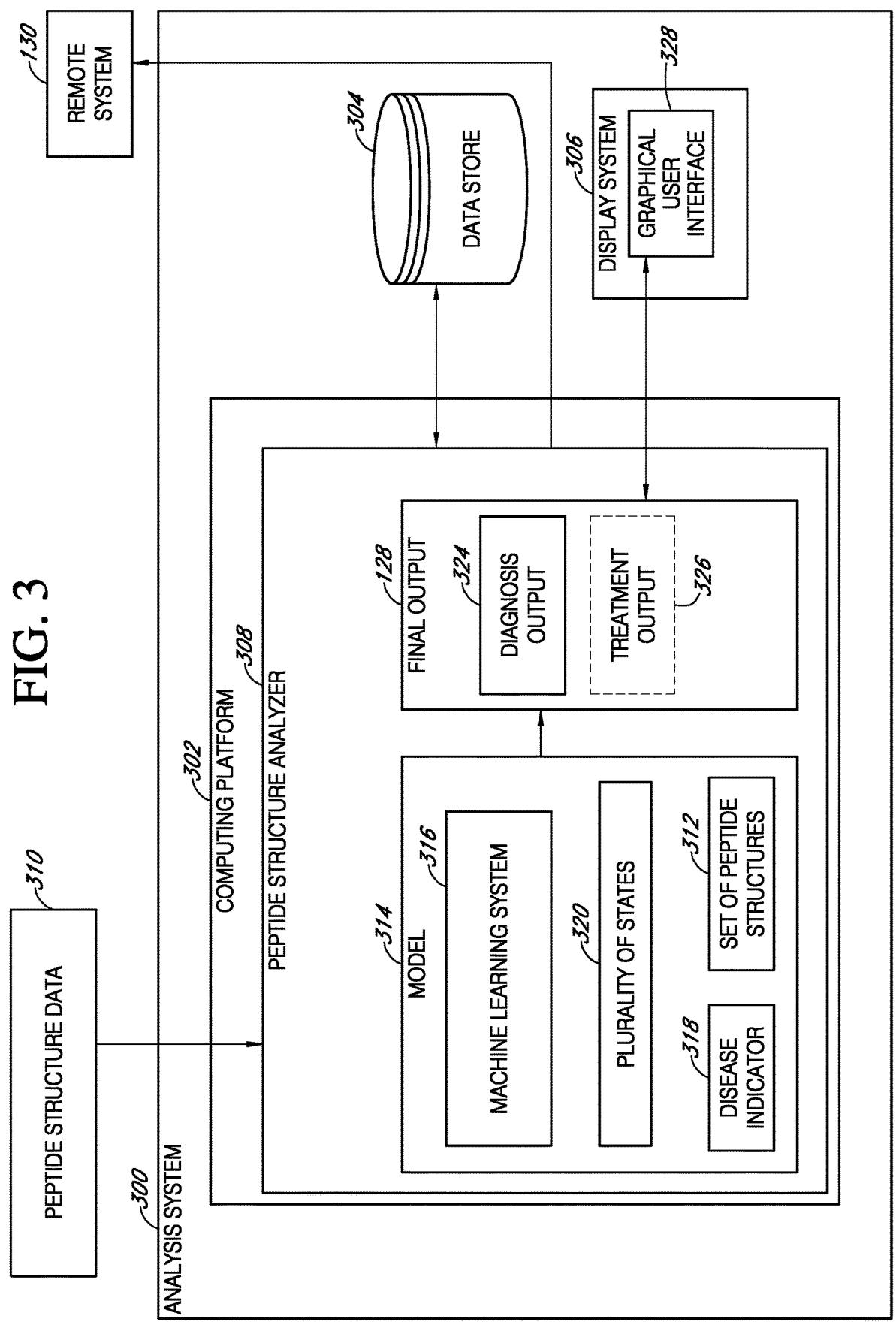
FIG. 3 is a block diagram of an analysis system in accordance with one or more embodiments.

FIG. 3 is a block diagram of an analysis system 300 in accordance with one or more embodiments. Analysis system 300 can be used to both detect and analyze various peptide structures that have been associated with various states of FLD. Analysis system 300 is one example of an implementation for a system that may be used to perform data analysis 108 in FIG. 1. Thus, analysis system 300 is described with continuing reference to workflow 100 as described in FIGS. 1, 2A, and/or 2B.

Analysis system 300 may include computing platform 302 and data store 304. In some embodiments, analysis system 300 also includes display system 306. Computing platform 302 may take various forms. In one or more embodiments, computing platform 302 includes a single computer (or computer system) or multiple computers in communication with each other. In other examples, computing platform 302 takes the form of a cloud computing platform.

Data store 304 and display system 306 may each be in communication with computing platform 302. In some examples, data store 304, display system 306, or both may be considered part of or otherwise integrated with computing platform 302. Thus, in some examples, computing platform 302, data store 304, and display system 306 may be separate components in communication with each other, but in other examples, some combination of these components may be integrated together. Communication between these different components may be implemented using any number of wired communications links, wireless communications links, optical communications links, or a combination thereof.

Analysis system 300 includes, for example, peptide structure analyzer 308, which may be implemented using hardware, software, firmware, or a combination thereof. In one or more embodiments, peptide structure analyzer 308 is implemented using computing platform 302.

Peptide structure analyzer 308 receives peptide structure data 310 for processing Peptide structure data 310 may be, for example, the peptide structure data that is output from sample preparation and processing 106 in FIGS. 1, 2A, and 2B. Accordingly, peptide structure data 310 may correspond to set of peptide structures 122 identified for biological sample 112 and may thereby correspond to biological sample 112.

Peptide structure data 310 can be sent as input into peptide structure analyzer 308, retrieved from data store 304 or some other type of storage (e.g., cloud storage), accessed from cloud storage, or obtained in some other manner. In some cases, peptide structure data 310 may be retrieved from data store 304 in response to (e.g., directly or indirectly based on) receiving user input entered by a user via an input device.

Peptide structure data 310 may include quantification data for the plurality of peptide structures. For example, peptide structure data 310 may include a set of quantification metrics for each peptide structure of a plurality of peptide structures. A quantification metric for a peptide structure may be selected as one of a relative quantity, an adjusted quantity, a normalized quantity, a relative abundance, an adjusted abundance, and a normalized abundance. In some cases, a quantification metric for a peptide structure is selected from one of a relative concentration, an adjusted concentration, and a normalized concentration. In this manner, peptide structure data 310 may provide abundance information about the plurality of peptide structures with respect to biological sample 112.

In some embodiments, a peptide structure of set of peptide structures 312 comprises a glycosylated peptide structure, or glycopeptide structure, that is defined by a peptide sequence and a glycan structure attached to a linking site of the peptide sequence. For example, the peptide structure may be a glycopeptide or a portion of a glycopeptide. In some embodiments, a peptide structure of set of peptide structures 312 comprises an aglycosylated peptide structure that is defined by a peptide sequence. For example, the peptide structure may be a peptide or a portion of a peptide and may be referred to as a quantification peptide.

Set of peptide structures 312 may be identified as being those most predictive or relevant to the symptomatic disease state based on training of model 314. In one or more embodiments, set of peptide structures 312 includes at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23 at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, or all 53 of the peptide structures identified in Table 1 below. The number of peptide structures selected from Table 1 for inclusion in set of peptide structures 312 may be based on, for example, a desired level of accuracy. In one or more embodiments, 40 peptide structures are selected from Table 1 for inclusion in set of peptide structures 312.

In Table 1, "PS-ID No." identifies a label or index for the peptide structure; "Peptide Structure (PS) Name" identifies a name for the peptide structure; "Prot. SEQ ID NO." identifies the sequence ID of the protein associated with the peptide structure (e.g., from which the peptide structure is derived); "Pep. SEQ ID No. identifies the peptide SEQ ID NO. for the peptide sequence of the peptide structure; "Monoisotopic mass" identifies the monoisotopic mass of the peptide structure in Daltons (Da); "Linking Site Pos. in Prot. Seq." identifies the site position with respect to the protein sequence at which the corresponding glycan structure is linked; "Linking Site Pos. in Pep. Seq." identifies the site position with respect to the peptide sequence at which the corresponding glycan structure is linked; and "GL NO." identifies a label or index for the corresponding glycan structure. For glycopeptide structures, the name for the peptide structure includes an abbreviation of the protein associated with the peptide structure, a first number that corresponds with the linking site position with respect to the protein sequence of the protein, and a second number that identifies the glycan linked to the protein. For aglycosylated peptide structures, the name for the peptide structure includes an abbreviation of the protein associated with the peptide structure and the corresponding peptide sequence of the peptide structure.

TABLE 1

Peptide Structures associated with FLD

| PS-ID NO. | Peptide Structure (PS) Name | Prot. SEQ ID NO. | Pep. SEQ ID NO. | Mono- isotopic mass (Da) | Linking Site Pos. in Prot. Seq. | Linking Site Pos. in Pep. Seq. | GL NO. |
|---|---|---|---|---|---|---|---|
| PS-1 | A1AT (271)-5401 | 1 | 23 | 3668.56 | 271 | 4 | 5401 |
| PS-2 | A1AT (271)-5402 | 1 | 23 | 3959.66 | 271 | 4 | 5402 |
| PS-3 | A1BG (179)-5402 | 2 | 24 | 6040.44 | 179 | 27 | 5402 |
| PS-4 | A2MG-AIGYLNTGYQR ("AIGYLNTGYQR" disclosed as SEQ ID NO: 25) | 3 | 25 | 1254.64 | N/A | N/A | N/A |
| PS-5 | A2MG-TEHPFTVEEFVLPK ("TEHPFTVEEFVLPK" disclosed as SEQ ID NO: 26) | 3 | 26 | 1671.85 | N/A | N/A | N/A |
| PS-6 | A2MG (1424)-5402 | 3 | 27 | 4366.95 | 1424 | 3 | 5402 |
| PS-7 | A2MG (247)-5200 | 3 | 28 | 4950.31 | 247 | 10 | 5200 |
| PS-8 | A2MG (247)-5401 | 3 | 28 | 5647.57 | 247 | 10 | 5401 |
| PS-9 | A2MG (247)-5402 | 3 | 28 | 5938.66 | 247 | 10 | 5402 |
| P5-10 | A2MG (55)-5402 | 3 | 29 | 4601.00 | 55 | 9 | 5402 |
| PS-11 | A2MG (55)-5411 | 3 | 29 | 4455.96 | 55 | 9 | 5411 |
| PS-12 | A2MG (55)-5412 | 3 | 29 | 4747.06 | 55 | 9 | 5412 |
| PS-13 | A2MG (869)-5200 | 3 | 30 | 4629.04 | 869 | 6 | 5200 |
| PS-14 | A2MG (869)-6200 | 3 | 30 | 4791.10 | 869 | 6 | 6200 |
| PS-15 | A2MG (869)-6300 | 3 | 30 | 4994.18 | 869 | 6 | 6300 |
| PS-16 | A2MG (991)-5402 | 3 | 31 | 8432.83 | 991 | 46 | 5402 |
| PS-17 | AACT (106)-7604 | 4 | 32 | 5916.41 | 106 | 2 | 7604 |
| PS-18 | AFAM (33)-5402 | 5 | 33 | 3399.32 | 33 | 6 | 5402 |
| PS-19 | AGP1 (33)-5402 | 6 | 34 | 4780.18 | 33 | 15 | 5402 |
| PS-20 | AGP1 (93)-6502 | 6 | 35 | 4484.79 | 93 | 7 | 6502 |
| PS-21 | APOC3 (74)-1102 | 7 | 36 | 3083.34 | 94 | 14 | 1102 |
| PS-22 | APOC3 (74)-1202 | 7 | 36 | 3286.42 | 94 | 14 | 1202 |
| PS-23 | APOC3 (74)-1300 | 7 | 36 | 2907.31 | 94 | 14 | 1300 |
| PS-24 | APOC3 (74)-2110 | 7 | 36 | 2809.26 | 94 | 14 | 2110 |
| PS-25 | APOM (135)-5421 | 8 | 37 | 4736.93 | 135 | 15 | 5421 |
| PS-26 | CFAI (70)-5401 | 9 | 38 | 2976.16 | 70 | 1 | 5401 |
| PS-27 | CLUS (374)-6501 | 10 | 39 | 3961.64 | 374 | 3 | 6501 |
| PS-28 | CO4A (1328)-5402 | 11 | 40 | 3308.37 | 1328 | 3 | 5402 |
| PS-29 | CO6 (324)-5200 | 12 | 41 | 2037.89 | 324 | 3 | 5200 |
| PS-30 | CO6 (324)-5400 | 12 | 41 | 2444.05 | 324 | 3 | 5400 |
| PS-31 | CO8A (437)-5200 | 13 | 42 | 2549.04 | 437 | 13 | 5200 |
| PS-32 | CO8A (437)-5410 | 13 | 42 | 3101.26 | 437 | 13 | 5410 |
| PS-33 | HPT (207)-10803 | 14 | 43 | 5576.18 | 207 & 211 | 5 & 9 | 5401 & 5402 |
| PS-34 | HPT (207)-11904 | 14 | 43 | 6232.40 | 207 & 211 | 5 & 9 | 6502 & 5402 |
| PS-35 | HPT (207)-121005 | 14 | 43 | 6888.63 | 207 & 211 | 5 & 9 | 6503 & 6502 |
| PS-36 | HPT (241)-5401 | 14 | 44 | 3707.68 | 241 | 6 | 5401 |
| PS-37 | HPT (241)-5402 | 14 | 44 | 3998.78 | 241 | 6 | 5402 |
| PS-38 | HPT (241)-5511 | 14 | 44 | 4056.82 | 241 | 6 | 5511 |
| PS-39 | HPT (241)-6502 | 14 | 44 | 4363.91 | 241 | 6 | 6502 |
| PS-40 | IGA2 (205)-5510 | 15 | 45 | 2929.27 | 205 | 6 | 5510 |
| PS-41 | IGG1 (297)-5411 | 16 | 46 | 3248.24 | 180 | 5 | 5411 |
| PS-42 | IGG2 (297)-4400 | 17 | 47 | 2617.04 | 176 | 5 | 4400 |
| PS-43 | IGG2 (297)-4411 | 17 | 47 | 3054.20 | 176 | 5 | 4411 |
| PS-44 | IGM (209)-5401 | 18 | 48 | 4251.75 | 209 | 7 | 5401 |
| PS-45 | KLKB1 (494)-5401 | 19 | 49 | 4159.85 | 494 | 6 | 5401 |
| PS-46 | KLKB1 (494)-5402 | 19 | 49 | 4450.95 | 494 | 6 | 5402 |
| PS-47 | KLKB1 (494)-5410 | 19 | 49 | 4014.82 | 494 | 6 | 5410 |
| PS-48 | KLKB1 (494)-6503 | 19 | 49 | 5107.18 | 494 | 6 | 6503 |
| PS-49 | TRFE (432)-5402 | 20 | 50 | 3680.52 | 432 | 12 | 5402 |
| PS-50 | TRFE (432)-6501 | 20 | 50 | 3754.55 | 432 | 12 | 6501 |
| PS-51 | TRFE (432)-6502 | 20 | 50 | 4045.65 | 432 | 12 | 6502 |
| PS-52 | VTNC (169)-5401 | 21 | 51 | 2824.14 | 169 | 1 | 5401 |
| PS-53 | ZA2G (112)-5402 | 22 | 52 | 4269.72 | 112 | 10 | 5402 |

In one or more embodiments, set of peptide structures 312 includes only peptide structures fragmented from alpha-2-macroglobulin (A2MG) and thus only A2MG glycoforms. In one or more embodiments, set of peptide structures 312 includes only peptide structures fragmented from the alpha-1-acid glycoprotein 1 (AGP1) and thus only AGP1 glycoforms. In one or more embodiments, set of peptide structures 312 includes only peptide structures fragmented from haptoglobin (HPT) and thus only HPT glycoforms. In one or more embodiments, set of peptide structures 312 includes only peptide structures fragmented from Complement Factor H (CFAH) and thus only CFAH glycoforms. In one or more embodiments, set of peptide structures 312 includes only peptide structures fragmented from alpha-1-antitrypsin (A1AT) and thus only A1AT glycoforms. In some embodiments, set of peptide structures 312 includes only peptide structures fragmented from at least one of A2MG, AGP1, HPT, CFAH, or A1AT.

Peptide structure analyzer 308 includes model 314 that is configured to receive peptide structure data 310 for processing. Model 314 may be implemented in any of a number of different ways. Model 314 may be implemented using any number of models, functions, equations, algorithms, and/or other mathematical techniques.

In one or more embodiments, model 314 includes machine learning model 316, which may itself be comprised of any number of machine learning models and/or algorithms. For example, machine learning model 316 may include, without limitation, at least one of a parametric model, a non-parametric model, deep learning model, a neural network, a linear discriminant analysis model, a quadratic discriminant analysis model, a support vector machine, a random forest algorithm, a nearest neighbor algorithm (e.g., a k-Nearest Neighbors algorithm), a combined discriminant analysis model, a k-means clustering algorithm, an unsupervised model, a logistic regression model, a multivariable regression model, a penalized multivariable regression model, or another type of model. In various embodiments, model 314 includes a machine learning model 316 that comprises any number of or combination of the models or algorithms described above.

In various embodiments, model 314 analyzes the portion (e.g., some or all of) peptide structure data 310 corresponding set of peptide structures 312 to generate disease indicator 318 that classifies biological sample 112 as evidencing a corresponding state of a plurality of states 320 associated with FLD progression. Disease indicator 318 may take various forms. In one or more embodiments, disease indicator 318 is a score that indicates a classification of the corresponding state for biological sample 112. For example, each of the states 320 may be associated with a different range of values for the score. If the score falls within a selected range associated with a particular state of the states 320, then the score indicates that biological sample 112 evidences that particular state. Thus, the score provides a classification of biological sample 112 as corresponding to that particular state.

In other embodiments, disease indicator 318 includes a score that indicates a probability that a subject (e.g., subject 114 in FIG. 1) falls within one of the states 320 associated with FLD progression. For example, disease indicator 318 may include one or more scores, each of which may indicate whether biological sample 112 evidences a corresponding state of the states 320 associated with FLD progression. In some examples, disease indicator 318 includes a score for each of the states 320 associated with FLD progression. A higher score indicates a higher probability that biological sample 112 evidences the corresponding state.

In various embodiments, machine learning model 316 takes the form of regression model 320. Regression model 320 may include, for example, at least one LASSO regression model (or LASSO regularization model) that is trained to compute disease indicator 318. Regression model 320 may be trained to identify weight coefficients for peptide structures of set of peptide structures 312.

Peptide structure analyzer 308 may generate final output 128 based on disease indicator 318 that is output by model 314. In other embodiments, final output 128 may be an output generated by model 314.

In some embodiments, final output 128 includes disease indicator 318. In other embodiments, final output 128 includes diagnosis output 324 and/or treatment output 326. Diagnosis output 324 may include, for example, an identification of a classification of which of the states 320 evidenced by biological sample 112 based on disease indicator 318. Treatment output 326 may include, for example, at least one of an identification of a therapeutic to treat the subject, a design for the therapeutic, or a treatment plan for administering the therapeutic. In some embodiments, the therapeutic is an immune checkpoint inhibitor.

Final output 128 may be sent to remote system 130 for processing in some examples. In other embodiments, final output 128 may be displayed on graphical user interface 328 in display system 306 for viewing by a human operator. The human operator may use final output 128 to diagnose and/or treat subject when final output 128 indicates the subject is positive a state (e.g., NASH, HCC) along a disease progression of a disease (e.g., FLD).

V.B. Computer Implemented System

Figure 4:
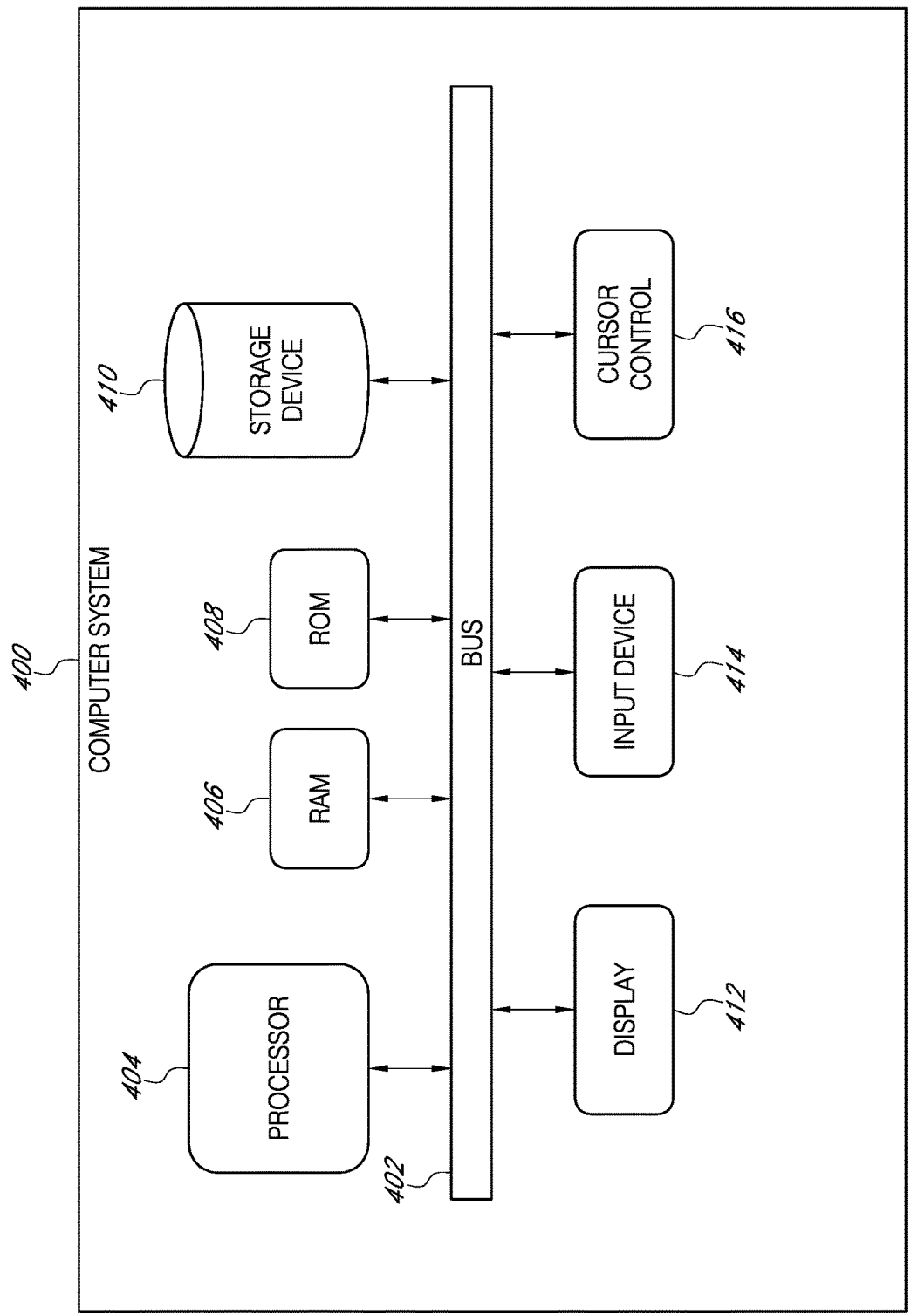
FIG. 4 is a block diagram of a computer system in accordance with various embodiments.

FIG. 4 is a block diagram of a computer system in accordance with various embodiments. Computer system 400 may be an example of one implementation for computing platform 302 described above in FIG. 3.

In one or more examples, computer system 400 can include a bus 402 or other communication mechanism for communicating information, and a processor 404 coupled with bus 402 for processing information. In various embodiments, computer system 400 can also include a memory, which can be a random-access memory (RAM) 406 or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a joystick, a trackball, a gesture input device, a gaze-based input device, or cursor direction keys for communicating direction information and command selections to processor 404 and for controlling cursor movement on display 412. This input device 414 typically has two degrees of freedom in two axes, a first axis (e.g., x) and a second axis (e.g., y), that allows the device to specify positions in a plane. However, it should be understood that input devices 414 allowing for three-dimensional (e.g., x, y, and z) cursor movement are also contemplated herein.

Consistent with certain implementations of the present teachings, results can be provided by computer system 400 in response to processor 404 executing one or more sequences of one or more instructions contained in RAM 406. Such instructions can be read into RAM 406 from another computer-readable medium or computer-readable storage medium, such as storage device 410. Execution of the sequences of instructions contained in RAM 406 can cause processor 404 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as RAM 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 400 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 400, whereby processor 404 would execute the analyses and determinations provided by these engines, subject to instructions provided by any one of or combination of, the memory components RAM 406, ROM, 408, or storage device 410 and user input provided via input device 414.

VI. Exemplary Methodologies Relating to Diagnosis Based on Peptide Structure Data Analysis

VI.A. General Methodology

Figure 5:
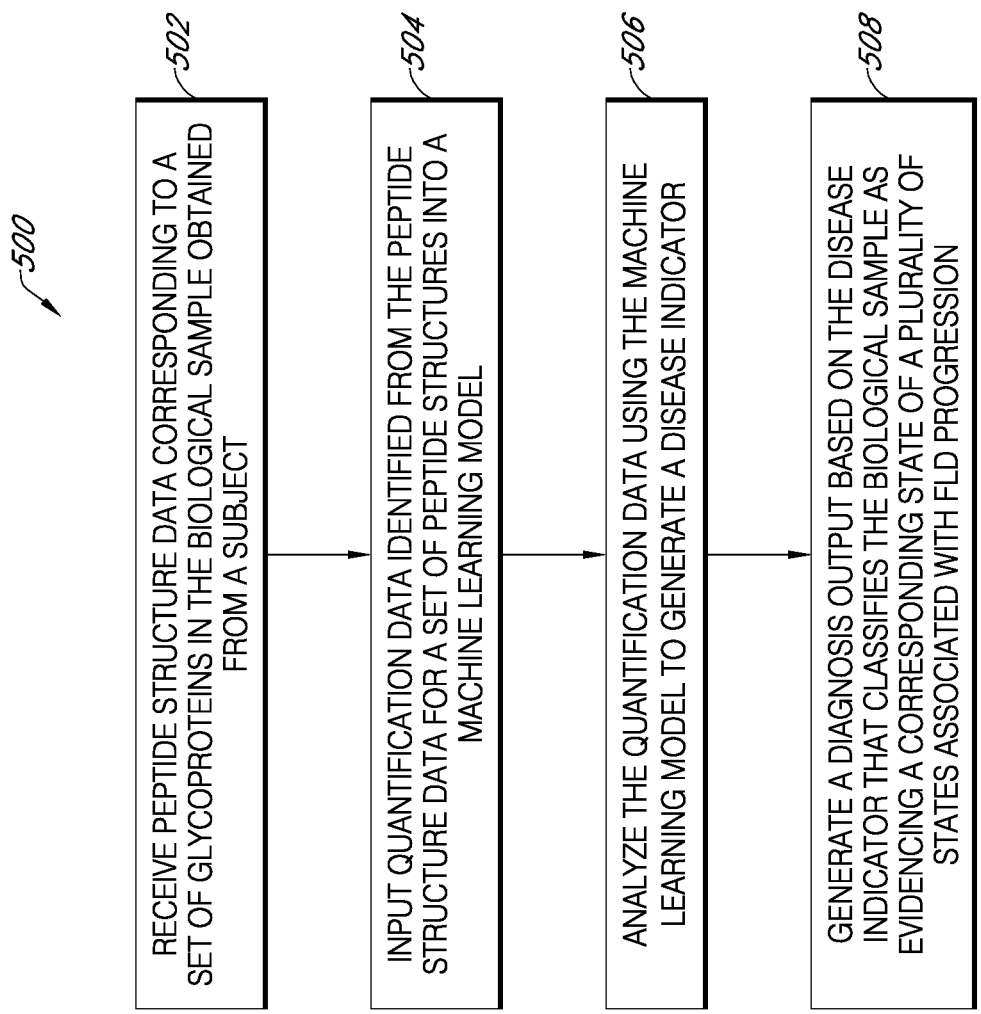
FIG. 5 is a flowchart of a process for evaluating a biological sample obtained from a subject with respect to an FLD progression in accordance with one or more embodiments.

FIG. 5 is a flowchart of a process for classifying a biological sample obtained from a subject with respect to a plurality of states associated with fatty liver (FLD) progression. Process 500 may be implemented using, for example, at least a portion of workflow 100 as described in FIGS. 1, 2A, and 2B and/or analysis system 300 as described in FIG. 3. Process 500 may be used to generate a diagnosis output such as, for example, diagnosis output 324 in FIG. 3.

Step 502 includes receiving peptide structure data corresponding to a set of glycoproteins in the biological sample obtained from a subject. The peptide structure data may be, for example, one example of an implementation of peptide structure data 310 in FIG. 3. The peptide structure data may include quantification data for each peptide structure of a plurality of peptide structures. The peptide structure data may have been generated using for example, without limitation, multiple reaction monitoring mass spectrometry (MRM-MS). In one or more embodiments, the peptide structure data includes quantification data for the plurality of peptide structures. This quantification data for a peptide structure may include, for example, without limitation, at least one of an abundance, a relative abundance, a normalized abundance, a relative quantity, an adjusted quantity, a normalized quantity, a relative concentration, an adjusted concentration, or a normalized concentration for the peptide structure. In one or more embodiments, the quantification data comprises normalized abundances for the peptide structures.

In one or more embodiments, the peptide structure data is generated for a sample created from the biological sample. For example, the biological sample may be prepared using reduction, alkylation, and enzymatic digestion to form a prepared sample. The prepared sample includes the plurality of peptide structures for which the peptide structure data is generated and then received in step 502.

Step 504 includes inputting quantification data identified from the peptide structure data for a set of peptide structures into a machine learning model. In some embodiments, the set of peptide structures includes at least one peptide structure identified from a plurality of peptide structures in Table 1 above. In various embodiments, at least one peptide structure comprises a glycopeptide structure defined by a peptide sequence and a glycan structure linked to the peptide sequence at a linking site of the peptide sequence, as identified in Table 1.

The quantification data may include, for example, one or more quantification metrics for each peptide structure of the plurality of peptide structures. A quantification metric for a peptide structure may be, for example, but is not limited to, a relative quantity, an adjusted quantity, a normalized quantity, a relative concentration, an adjusted concentration, or a normalized concentration. In this manner, the quantification data for a given peptide structure provides an indication of the abundance of the peptide structure in the biological sample. In one or more embodiments, the quantification data comprises normalized abundances for the peptide structures. The machine learning model may be, for example, a supervised machine learning model.

Step 506 includes analyzing the quantification data using the machine learning model to generate a disease indicator. In various embodiments, the disease indicator that is generated may include an indication of whether the biological sample evidences a state associated with FLD progression. For example, the disease indicator may indicate whether the biological sample is likely positive for NASH or HCC or is likely healthy or non-NASH/HCC (e.g., may be indicative of a benign hepatic mass). In various embodiments, the disease indicator comprises a probability that the biological sample evidences a NASH state or a probability that the biological sample evidences an HCC state. In one or more embodiments, the machine learning model may generate an output that classifies the biological sample as positive for the NASH state, positive for the HCC state, or positive for a healthy (or non-NASH/HCC) state. In various embodiments, the disease indicator can be a score.

Step 508 includes generating a diagnosis output based on the disease indicator that classifies the biological sample as evidencing a corresponding state of a plurality of states associated with the FLD progression. In various embodiments, the plurality of states can include a NASH state and a hepatocellular carcinoma (HCC) state. In some embodiments, the plurality of states can include a non-NASH/HCC state that comprises at least one of a healthy state, a benign hepatic mass state, a liver disease-free state, or some other type non-NASH/HCC state.

When the disease indicator is a score, step 508 may include determining that the score falls within a selected range associated with the corresponding state of the plurality of states (e.g., between 0.0 and 0.05 for the non-NASH/HCC state, between 0.05 and 0.4 for the NASH state, and between 0.4 and 1.0 for the HCC state). In some embodiments, step 506 may include determining that the biological sample evidences the corresponding state based on a determination that the score falls within the selected range associated with corresponding state.

In one or more embodiments, generating the diagnosis output in step 508 includes generating the diagnosis output as part of a report that identifies the corresponding state. In some embodiments, step 508 may also include generating a treatment output based on at least one of the diagnosis output or the disease indicator. In some embodiments, the treatment output comprises at least one of an identification of a treatment to treat the subject, a design for the treatment, a manufacturing plan for the treatment, or a treatment plan for administering the treatment.

For a subject that has been diagnosed with NASH, the treatment may include, for example, a therapeutic dosage of at least one of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02. For a subject that has been diagnosed with NASH, the treatment may include, for example, a therapeutic dosage of at least one of Atezolizumab, Bevacizumab, Sorafenib, Lenvatinib, Nivolumab, Regorafenib, Cabozantinib, Pemigatinib, Ramucirumab, or Pembrolizumab.

Figure 6:
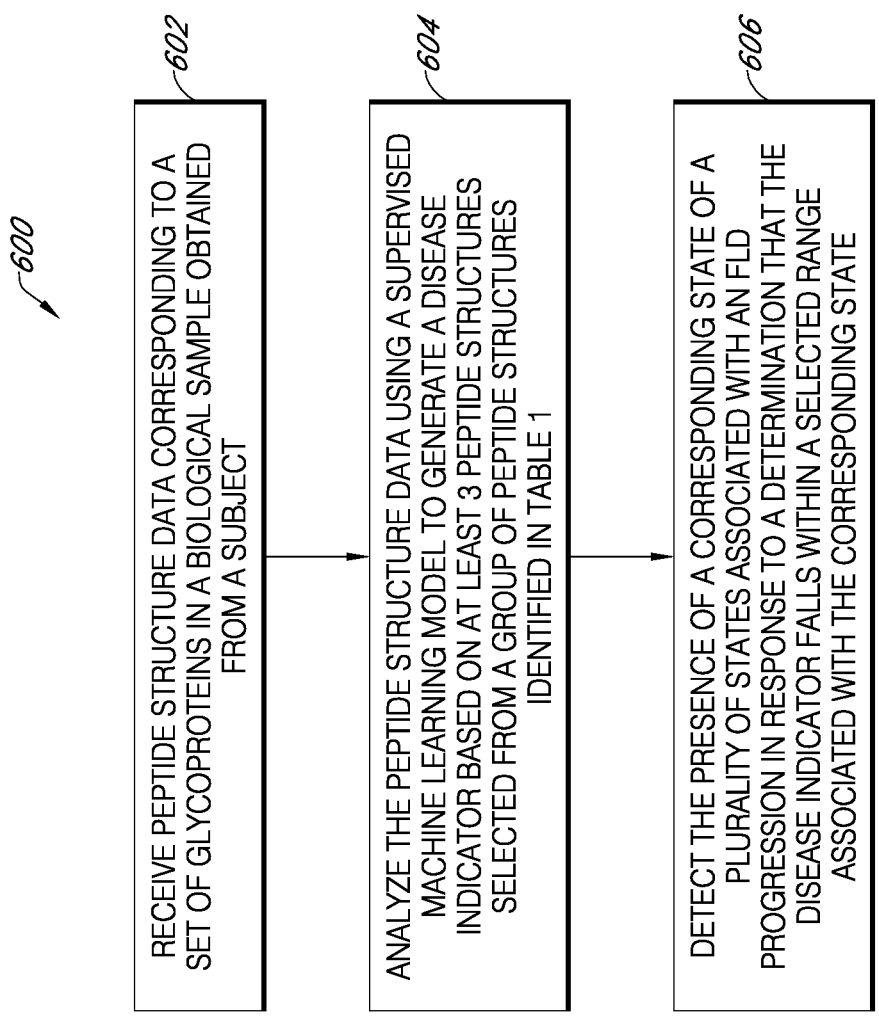
FIG. 6 is a flowchart of a process for detecting the presence of a disease state associated with an FLD progression in accordance with one or more embodiments.

FIG. 6 is a flowchart of a process for detecting a presence of one of a plurality of states associated with fatty liver disease (FLD) progression in a biological sample. Process 600 may be implemented using, for example, at least a portion of workflow 100 as described in FIGS. 1, 2A, and 2B and/or analysis system 300 as described in FIG. 3.

Step 602 includes receiving peptide structure data corresponding to a set of glycoproteins in the biological sample obtained from a subject. The peptide structure data may have been generated from a prepared sample using, for example, multiple reaction monitoring mass spectrometry (MRM-MS). The peptide structure data may include quantification data for each peptide structure of a panel of peptide structures. The quantification data for a peptide structure of the plurality of peptide structures may include at least one of a relative quantity, an adjusted quantity, a normalized quantity, a relative concentration, an adjusted concentration, a normalized concentration, or another quantification metric.

Step 604 includes analyzing the peptide structure data using a supervised machine learning model to generate a disease indicator based on at least 3 peptide structures selected from a group of peptide structures identified in Table 1. In one or more embodiments, the supervised machine learning model comprises a logistic regression model.

In various embodiments, the at least 3 peptide structures include a glycopeptide structure defined by a peptide sequence and a glycan structure linked to the peptide sequence at a linking site of the peptide sequence, as identified in Table 1, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, 51, or 52 as defined in Table 1.

In one or more embodiments, the at least 3 peptide structures include only peptide structures fragmented from alpha-2-macroglobulin (A2MG). In one or more embodiments, the at least 3 peptide structures include only peptide structures fragmented from the alpha-1-acid glycoprotein 1 (AGP1). In one or more embodiments, the at least 3 peptide structures include only peptide structures fragmented from haptoglobin (HPT). In one or more embodiments, the at least 3 peptide structures include only peptide structures fragmented from Complement Factor H (CFAH). In one or more embodiments, the at least 3 peptide structures include only peptide structures fragmented from alpha-1-antitrypsin (A1 AT).

In various embodiments, step 604 may include computing a peptide structure profile for the biological sample that identifies a weighted value for each peptide structure of the at least 3 peptide structures. In some embodiments, the weighted value for a peptide structure of the at least 3 peptide structures can be a product of a quantification metric for the peptide structure identified from the peptide structure data and a weight coefficient for the peptide structure. The weight coefficient of a corresponding peptide structure of the at least 3 peptide structures may indicate the relative significance of the corresponding peptide structure to the disease indicator. In one or more embodiments, analyzing the peptide structure data comprises computing the disease indicator using the peptide structure profile. The disease indicator may be, for example, a score that that indicates which state of a plurality of states is evidenced by the biological sample.

In one or more embodiments, the supervised machine learning model employs 3 different models in generating the final disease indicator. These three models may each be, for example, a regression model that is used to analyze the peptide structure quantification data for a particular state versus the other states. For example, each of these 3 regression models may be used to distinguish between a given state of the plurality of states and the other states of the plurality of states.

In one or more embodiments, the at least 3 peptide structures of step 604 may be selected from those peptide structures identified in Table 2 below, where Table 2 includes a subset of the peptide structures identified in Table 1. Table 2 further identifies the weight coefficients associated with distinguishing between the NASH state versus the other states (e.g., HCC state and control state), between the HCC state versus the other states (e.g., the NASH state and the control state), and between the control state versus the other states (e.g., the NASH state and the HCC state).

In Table 2, "PS-ID No." identifies the label or index for the peptide structure; "Peptide Structure (PS) Name" identifies the name for the peptide structure; "Prot. SEQ ID NO." identifies the sequence ID of the protein associated with the peptide structure (e.g., from which the peptide structure is derived); "Pep. SEQ ID No. identifies the peptide SEQ ID NO. for the peptide sequence of the peptide structure; "Coeff. (Control v. Rest)" identifies the weight coefficients between the control state versus the other states; "Coeff. (NASH v. Rest)" identifies the weight coefficients between NASH versus the other states; and "Coeff. (HCC v. Rest)" identifies the weight coefficients between HCC versus the other states.

TABLE 2

Peptide Structures and Associated Coefficients

| PS-ID NO. | Peptide Structure (PS) NAME | Prot. SEQ ID NO. | Pep. SEQ ID NO. | Coeff. (Control v. Rest) | Coeff. (NASH v. Rest) | Coeff. (HCC v. Rest) |
|---|---|---|---|---|---|---|
| PS-1 | A1AT (271)-5401 | 1 | 23 | 0.514 | 0.013 | 0.412 |
| PS-2 | A1AT (271)-5402 | 1 | 23 | 0.416 | 0.099 | 0.369 |
| PS-3 | A1BG (179)-5402 | 2 | 24 | 0.105 | 0.17 | 0.056 |
| PS-9 | A2MG (247)-5402 | 3 | 28 | 0.021 | 0.045 | 0.235 |
| PS-10 | A2MG (55)-5402 | 3 | 28 | 0.209 | 0.108 | 0.327 |
| PS-14 | A2MG (869)-6200 | 3 | 30 | 0.111 | 0.576 | 0.435 |
| PS-17 | AACT (106)-7604 | 4 | 32 | 0.353 | 0.287 | 0.0507 |
| PS-19 | AGP1 (33)-5402 | 6 | 33 | 0.113 | 0.138 | 0.11 |
| PS-20 | AGP1 (93)-6502 | 6 | 35 | 0.378 | 0.119 | 0.701 |
| PS-21 | APOC3 (74)-1102 | 7 | 36 | 0.551 | 0.312 | 0.123 |
| PS-22 | APOC3 (74)-1202 | 7 | 36 | 0.39 | 0.31 | 0.071 |
| PS-23 | APOC3 (74)-1300 | 7 | 36 | 0.293 | −1.44 | 0.588 |
| PS-24 | APOC3 (74)-2110 | 7 | 36 | 0.798 | 0.55 | 0.391 |
| PS-25 | APOM (135)-5421 | 8 | 37 | 0.707 | 0.14 | 0.624 |
| PS-26 | CFAI (70)-5401 | 9 | 38 | 0.389 | 0.68 | 0.075 |
| PS-27 | CLUS (374)-6501 | 10 | 39 | 0.669 | 1.119 | 0.644 |
| PS-28 | CO4A (1328)-5402 | 11 | 40 | 0.535 | 0.398 | 0.45 |
| PS-29 | CO6 (324)-5200 | 13 | 41 | 0.037 | 0.295 | 0.082 |
| PS-30 | CO6 (324)-5400 | 12 | 41 | 0.025 | 0.186 | 0.101 |
| PS-31 | CO8A (437)-5200 | 13 | 42 | 0.443 | 0.277 | 0.974 |
| PS-32 | CO8A (437)-5410 | 13 | 42 | 0.884 | 0.274 | 0.122 |
| PS-34 | HPT (207)-11904 | 14 | 43 | 0.265 | 0.769 | −1.036 |
| PS-35 | HPT (207)-121005 | 14 | 43 | 0.304 | 0.335 | 0.606 |
| PS-36 | HPT (241)-5401 | 14 | 44 | 0.417 | 0.104 | 0.743 |
| PS-37 | HPT (241)-5402 | 14 | 44 | 0.051 | 0.907 | 0.131 |
| PS-38 | HPT (241)-5511 | 14 | 44 | 0.428 | 0.318 | 0.249 |
| PS-39 | HPT (241)-6502 | 14 | 44 | 0.986 | 0.417 | 0.508 |
| PS-40 | IGA2 (205)-5510 | 15 | 45 | 1.463 | 0.592 | 0.558 |
| PS-42 | IGG2 (297)-4400 | 17 | 47 | 0.975 | 0.906 | 0.847 |
| PS-43 | IGG2 (297)-4411 | 17 | 47 | 0.272 | 0.371 | 0.181 |
| PS-44 | IGM (209)-5401 | 18 | 48 | 0.682 | 0.17 | 0.266 |
| PS-45 | KLKB1 (494)-5401 | 19 | 49 | 0.459 | 0.017 | 0.086 |
| PS-46 | KLKB1 (494)-5402 | 19 | 49 | 0.068 | 0.223 | 0.331 |
| PS-47 | KLKB1 (494)-5410 | 19 | 49 | 1.11 | 0.037 | 0.829 |
| PS-48 | KLKB1 (494)-6503 | 19 | 49 | 0.231 | 0.707 | 0.646 |
| PS-49 | TRFE (432)-5402 | 20 | 50 | 0.311 | 0.938 | 1.004 |
| PS-50 | TRFE (432)-6501 | 20 | 50 | 0.337 | 0.204 | 0.146 |
| PS-51 | TRFE (432)-6502 | 20 | 50 | 0.107 | 0.539 | 0.2 |
| PS-52 | VTNC (169)-5401 | 21 | 51 | 0.551 | 0.28 | 0.238 |
| PS-53 | ZA2G (112)-5402 | 22 | 52 | 0.177 | 0.308 | 0.171 |

Step 606 includes detecting the presence of a corresponding state of the plurality of states associated with the FLD progression in response to a determination that the disease indicator falls within a selected range associated with the corresponding state. In some embodiments, the plurality of states includes at least two selected from a group consisting of a non-alcoholic steatohepatitis (NASH) state, a hepatocellular carcinoma (HCC) state, or a non-NASH/HCC state (e.g., a non-alcoholic fatty liver disease state, a control state, a healthy state, a benign hepatic mass state, a liver disease-free state).

In one or more embodiments, the corresponding state is a non-NASH/HCC state and the selected range for the disease indicator associated with the non-NASH/HCC state is between 0.00 and about 0.05. In some embodiments, the corresponding state is a NASH state and the selected range for the disease indicator associated with the NASH state is between 0.05 and 0.4. In some embodiments, the corresponding state is an HCC state and the selected range for the disease indicator associated with the HCC state is between 0.4 and 1.0.

In one or more embodiments, process 600 may further include generating a report that includes a diagnosis based on the corresponding state detected for the subject. The report may include, for example, the disease indicator.

VI. B. Training a Model

Figure 7:
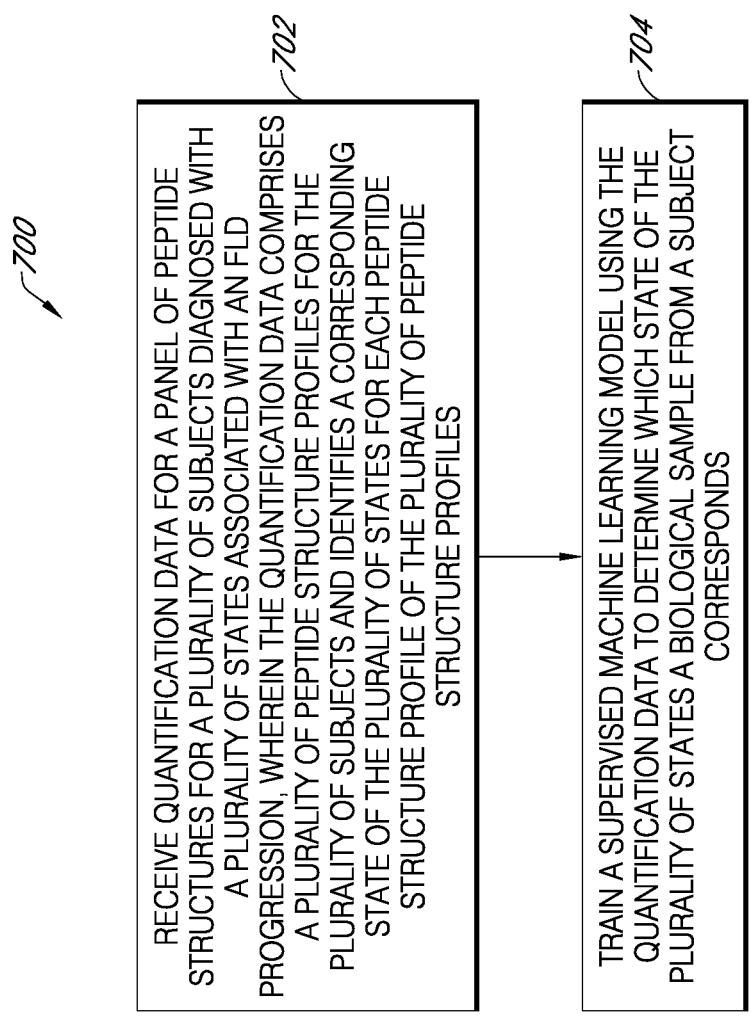
FIG. 7 is a flowchart of a process for training a supervised machine learning model for determining which state of a plurality of states a biological sample corresponds in accordance with various embodiments.

FIG. 7 is a flowchart of a process for training a model to generate a classify a biological sample as belonging to or evidencing one of a plurality of states associated with FLD progression. Process 700 may be implemented using, for example, analysis system 300 as described in FIG. 3. In one or more embodiments, process 700 may be performed to train model 314 in FIG. 3.

Step 702 includes receiving quantification data for a panel of peptide structures for a plurality of subjects diagnosed with the plurality of states associated with the FLD progression, wherein the quantification data comprises a plurality of peptide structure profiles for the plurality of subjects and identifies a corresponding state of the plurality of states for each peptide structure profile of the plurality of peptide structure profiles.

In one or more embodiments, the plurality of peptide structure profiles comprises normalized abundance data for a first number of peptide structures. In one or more embodiments, the quantification data for the panel of peptide structures for the plurality of subjects diagnosed with the plurality of states comprises at least one of an abundance, a relative abundance, a normalized abundance, a relative quantity, an adjusted quantity, a normalized quantity, a relative concentration, an adjusted concentration, or a normalized concentration.

Step 704 includes training a supervised machine learning model using the quantification data to determine which state of the plurality of states a biological sample from a subject corresponds. In various embodiments, the supervised machine learning model comprises a logistic regression model. In one or more embodiments, the logistic regression model may be a LASSO regularization model. The plurality of states may include, for example, at least one of a NASH state, an HCC state, or a non-NASH/HCC state.

In one or more embodiments, step 704 may include, for example, training the supervised machine learning model to make the determination of state based on the quantification data for at least 3 peptide structures from the list of peptide structures identified in Table 1 or in Table 2 above.

The peptide structures selected for training may be peptide structures identified from, for example, a differential expression analysis performed using initial training data to compare the quantification data for peptide structures for a first portion of the plurality of subjects diagnosed with NASH, a second portion of the plurality of subjects diagnosed with HCC, and a third portion of the plurality of subjects diagnosed with a non-NASH/HCC condition (e.g., a healthy state, a benign hepatic mass, liver disease-free state, etc.).

For example, comparisons may be performed to compare peptide structure quantification data between the first portion of subjects with NASH versus the third portion of subjects with the non-NASH/HCC condition (e.g., the control state), to compare the second portion of subjects with HCC versus the first portion of subjects with NASH, and/or to compare the first portion of subjects with NASH versus the second portion of subjects with HCC. In some embodiments, the comparisons may be normalized and compared to one another.

Tables 3A-3C below indicates the fold changes (FC), false discovery rates (FDR), and p-values computed based on such comparisons.

TABLE 3A

Differential Expression Analysis for NASH v. Control

| PS-ID NO. | PS NAME | NASH/ Control (fold change) | NASH/ Control (FDR) | NASH/ Control (p-value) |
|---|---|---|---|---|
| PS-1 | A1AT (271)-5401 | 0.85 | 0.005 | <0.001 |
| PS-2 | A1AT (271)-5402 | 0.87 | <0.001 | <0.001 |
| PS-3 | A1BG (179)-5402 | 1.17 | 0.003 | <0.001 |
| PS-9 | A2MG (247)-5402 | 1.23 | 0.002 | <0.001 |
| PS-10 | A2MG (55)-5402 | 1.17 | 0.016 | 0.003 |
| PS-14 | A2MG (869)-6200 | 0.87 | 0.049 | 0.013 |
| PS-17 | AACT (106)-7604 | 0.45 | 0.001 | <0.001 |
| PS-19 | AGP1 (33)-5402 | 0.72 | 0.003 | <0.001 |
| PS-20 | AGP1 (93)-6502 | 0.82 | 0.038 | 0.009 |
| PS-21 | APOC3 (74)-1102 | 1.53 | <0.001 | <0.001 |
| PS-22 | APOC3 (74)-1202 | 1.73 | 0.008 | 0.001 |
| PS-23 | APOC3 (74)-1300 | 2.01 | 0.005 | <0.001 |
| PS-24 | APOC3 (74)-2110 | 1.93 | <0.001 | <0.001 |
| PS-25 | APOM (135)-5421 | 1.62 | 0.049 | 0.014 |
| PS-26 | CFAI (70)-5401 | 0.76 | 0.024 | 0.004 |
| PS-27 | CLUS (374)-6501 | 1.46 | 0.005 | <0.001 |
| PS-28 | CO4A (1328)-5402 | 1.17 | <0.001 | <0.001 |
| PS-29 | CO6 (324)-5200 | 1.57 | 0.025 | 0.005 |
| PS-30 | CO6 (324)-5400 | 1.76 | 0.01 | 0.002 |
| PS-31 | CO8A (437)-5200 | 0.72 | 0.043 | 0.011 |
| PS-32 | CO8A (437)-5410 | 1.43 | 0.035 | 0.008 |
| PS-34 | HPT (207)-11904 | 0.82 | 0.031 | 0.006 |
| PS-35 | HPT (207)-121005 | 0.72 | 0.025 | 0.005 |
| PS-36 | HPT (241)-5401 | 0.76 | 0.033 | 0.007 |
| PS-37 | HPT (241)-5402 | 0.8 | <0.001 | <0.001 |
| PS-38 | HPT (241)-5511 | 0.88 | 0.027 | 0.005 |
| PS-39 | HPT (241)-6502 | 1.25 | 0.021 | 0.004 |
| PS-40 | IGA2 (205)-5510 | 0.42 | 0.016 | 0.003 |
| PS-42 | IGG2 (297)-4400 | 0.69 | 0.022 | 0.004 |
| PS-43 | IGG2 (297)-4411 | 1.24 | 0.035 | 0.008 |
| PS-44 | IGM (209)-5401 | 1.5 | 0.016 | 0.003 |
| PS-45 | KLKB1 (494)-5401 | 1.7 | 0.001 | <0.001 |
| PS-46 | KLKB1 (494)-5402 | 1.84 | 0.017 | 0.003 |
| PS-47 | KLKB1 (494)-5410 | 1.27 | 0.041 | 0.01 |
| PS-48 | KLKB1 (494)-6503 | 1.51 | 0.002 | <0.001 |
| PS-49 | TRFE (432)-5402 | 1.19 | 0.008 | 0.001 |
| PS-50 | TRFE (432)-6501 | 1.24 | 0.001 | <0.001 |
| PS-51 | TRFE (432)-6502 | 1.13 | 0.049 | 0.013 |
| PS-52 | VTNC (169)-5401 | 0.71 | 0.002 | <0.001 |
| PS-53 | ZA2G (112)-5402 | 1.49 | 0.034 | 0.008 |

TABLE 3B

Differential Expression Analysis for HCC v. Control

| PS-ID NO. | PS-NAME | HCC/ control (fold change) | HCC/ Control (FDR) | HCC/ Control (p-value) |
|---|---|---|---|---|
| PS-1 | A1AT (271)-5401 | 0.79 | <0.001 | <0.001 |
| PS-2 | A1AT (271)-5402 | 0.82 | <0.001 | <0.001 |
| PS-3 | A1BG (179)-5402 | 1.28 | <0.001 | <0.001 |
| PS-9 | A2MG (247)-5402 | 1.47 | <0.001 | <0.001 |
| PS-10 | A2MG (55)-5402 | 1.34 | <0.001 | <0.001 |
| PS-14 | A2MG (869)-6200 | 0.68 | <0.001 | <0.001 |
| PS-17 | AACT (106)-7604 | 0.63 | 0.009 | 0.003 |
| PS-19 | AGP1 (33)-5402 | 0.75 | 0.008 | 0.002 |
| PS-20 | AGP1 (93)-6502 | 0.69 | <0.001 | <0.001 |
| PS-21 | APOC3 (74)-1102 | 1.77 | <0.001 | <0.001 |
| PS-22 | APOC3 (74)-1202 | 2.55 | <0.001 | <0.001 |
| PS-23 | APOC3 (74)-1300 | 7.53 | <0.001 | <0.001 |
| PS-24 | APOC3 (74)-2110 | 2.98 | <0.001 | <0.001 |
| PS-25 | APOM (135)-5421 | 2.3 | 0.002 | <0.001 |
| PS-26 | CFAI (70)-5401 | 0.74 | 0.0124 | 0.004 |
| PS-27 | CLUS (374)-6501 | 1.53 | 0.003 | <0.001 |
| PS-28 | CO4A (1328)-5402 | 1.39 | <0.001 | <0.001 |
| PS-29 | CO6 (324)-5200 | 2.42 | <0.001 | <0.001 |
| PS-30 | CO6 (324)-5400 | 1.9 | 0.023 | 0.008 |
| PS-31 | CO8A (437)-5200 | 0.57 | <0.001 | <0.001 |
| PS-32 | CO8A (437)-5410 | 1.75 | 0.006 | 0.002 |
| PS-34 | HPT (207)-11904 | 0.54 | <0.001 | <0.001 |
| PS-35 | HPT (207)-121005 | 0.56 | <0.001 | <0.001 |
| PS-36 | HPT (241)-5401 | 0.55 | <0.001 | <0.001 |
| PS-37 | HPT (241)-5402 | 0.75 | <0.001 | <0.001 |
| PS-38 | HPT (241)-5511 | 0.85 | 0.008 | 0.002 |
| PS-39 | HPT (241)-6502 | 1.68 | <0.001 | <0.001 |
| PS-40 | IGA2 (205)-5510 | 0.08 | <0.001 | <0.001 |
| PS-42 | IGG2 (297)-4400 | 0.52 | <0.001 | <0.001 |
| PS-43 | IGG2 (297)-4411 | 1.59 | <0.001 | <0.001 |
| PS-44 | IGM (209)-5401 | 1.47 | 0.031 | 0.011 |
| PS-45 | KLKB1 (494)-5401 | 2.87 | <0.001 | <0.001 |
| PS-46 | KLKB1 (494)-5402 | 2.99 | <0.001 | <0.001 |
| PS-47 | KLKB1 (494)-5410 | 1.79 | <0.001 | <0.001 |
| PS-48 | KLKB1 (494)-6503 | 1.6 | <0.001 | <0.001 |
| PS-49 | TRFE (432)-5402 | 1.66 | <0.001 | <0.001 |
| PS-50 | TRFE (432)-6501 | 1.47 | <0.001 | <0.001 |
| PS-51 | TRFE (432)-6502 | 1.42 | <0.001 | <0.001 |
| PS-52 | VTNC (169)-5401 | 0.54 | <0.001 | <0.001 |
| PS-53 | ZA2G (112)-5402 | 2.06 | <0.001 | <0.001 |

TABLE 3C

Differential Expression Analysis for NASH v. HCC

| PS-ID NO. | PS-NAME | NASH/ HCC (fold change) | NASH/ HCC (FDR) | NASH/ HCC (p-value) |
|---|---|---|---|---|
| PS-1 | A1AT (271)-5401 | 0.94 | 0.499 | 0.323 |
| PS-2 | A1AT (271)-5402 | 0.95 | 0.499 | 0.319 |
| PS-3 | A1BG (179)-5402 | 1.12 | 0.29 | 0.134 |
| PS-9 | A2MG (247)-5402 | 1.134 | 0.153 | 0.051 |
| PS-10 | A2MG (55)-5402 | 1.1 | 0.371 | 0.186 |
| PS-14 | A2MG (869)-6200 | 0.85 | 0.23 | 0.095 |
| PS-17 | AACT (106)-7604 | 1.43 | 0.466 | 0.281 |
| PS-19 | AGP1 (33)-5402 | 1 | 0.989 | 0.979 |
| PS-20 | AGP1 (93)-6502 | 0.88 | 0.464 | 0.2767 |
| PS-21 | APOC3 (74)-1102 | 1.11 | 0.576 | 0.412 |
| PS-22 | APOC3 (74)-1202 | 1.22 | 0.499 | 0.319 |
| PS-23 | APOC3 (74)-1300 | 2.51 | 0.013 | 0.0003 |
| PS-24 | APOC3 (74)-2110 | 1.43 | 0.228 | 0.094 |
| PS-25 | APOM (135)-5421 | 1.29 | 0.23 | 0.097 |
| PS-26 | CFAI (70)-5401 | 1.06 | 0.733 | 0.597 |
| PS-27 | CLUS (374)-6501 | 1.045 | 0.844 | 0.792 |
| PS-28 | CO4A (1328)-5402 | 1.19 | 0.013 | 0.0004 |
| PS-29 | CO6 (324)-5200 | 1.41 | 0.135 | 0.04 |
| PS-30 | CO6 (324)-5400 | 0.97 | 0.923 | 0.899888442 |
| PS-31 | CO8A (437)-5200 | 0.88 | 0.614 | 0.449 |

TABLE 3C-continued

Differential Expression Analysis for NASH v. HCC

| PS-ID NO. | PS-NAME | NASH/ HCC (fold change) | NASH/ HCC (FDR) | NASH/ HCC (p-value) |
|---|---|---|---|---|
| PS-32 | CO8A (437)-5410 | 1.22 | 0.55 | 0.377 |
| PS-34 | HPT (207)-11904 | 0.63 | 0.013 | 0.0004 |
| PS-35 | HPT (207)-121005 | 0.78 | 0.341 | 0.164 |
| PS-36 | HPT (241)-5401 | 0.77 | 0.152 | 0.051 |
| PS-37 | HPT (241)-5402 | 0.93 | 0.356 | 0.175 |
| PS-38 | HPT (241)-5511 | 0.94 | 0.341 | 0.165 |
| PS-39 | HPT (241)-6502 | 1.37 | 0.102 | 0.024 |
| PS-40 | IGA2 (205)-5510 | 0.25 | 0.222 | 0.09 |
| PS-42 | IGG2 (297)-4400 | 0.89 | 0.385 | 0.203 |
| PS-43 | IGG2 (297)-4411 | 1.29 | 0.102 | 0.024 |
| PS-44 | IGM (209)-5401 | 1.11 | 0.689 | 0.55 |
| PS-45 | KLKB1 (494)-5401 | 1.51 | 0.141 | 0.045 |
| PS-46 | KLKB1 (494)-5402 | 1.52 | 0.371 | 0.186 |
| PS-47 | KLKB1 (494)-5410 | 1.42 | 0.072 | 0.013 |
| PS-48 | KLKB1 (494)-6503 | 1.02 | 0.923 | 0.902 |
| PS-49 | TRFE (432)-5402 | 1.38 | 0.046 | 0.006 |
| PS-50 | TRFE (432)-6501 | 1.17 | 0.23 | 0.095 |
| PS-51 | TRFE (432)-6502 | 1.25 | 0.07 | 0.012 |
| PS-52 | VTNC (169)-5401 | 0.82 | 0.425 | 0.243 |
| PS-53 | ZA2G (112)-5402 | 1.11 | 0.76 | 0.657 |

VI.C. Combined Training and Diagnosis

The exemplary methodologies described in Section VI. may be used to diagnose a subject who may be suffering from FLD. This diagnosis may be used to determine a method of treatment for a subject. The embodiments described herein may enable faster and more accurate diagnosis of a state of NASH versus HCC. Being able to more quickly and accurately diagnose a subject (or patient) that has advanced from NASH to HCC in the FLD progression may enable treating the subject more quickly, which may lead to a more desirable treatment outcome for the subject. Further, being able to more quickly and accurately determine when a subject has advanced from NASH to HCC may be particularly useful reducing the need for hospitalization and avoidance of death.

Figure 8:
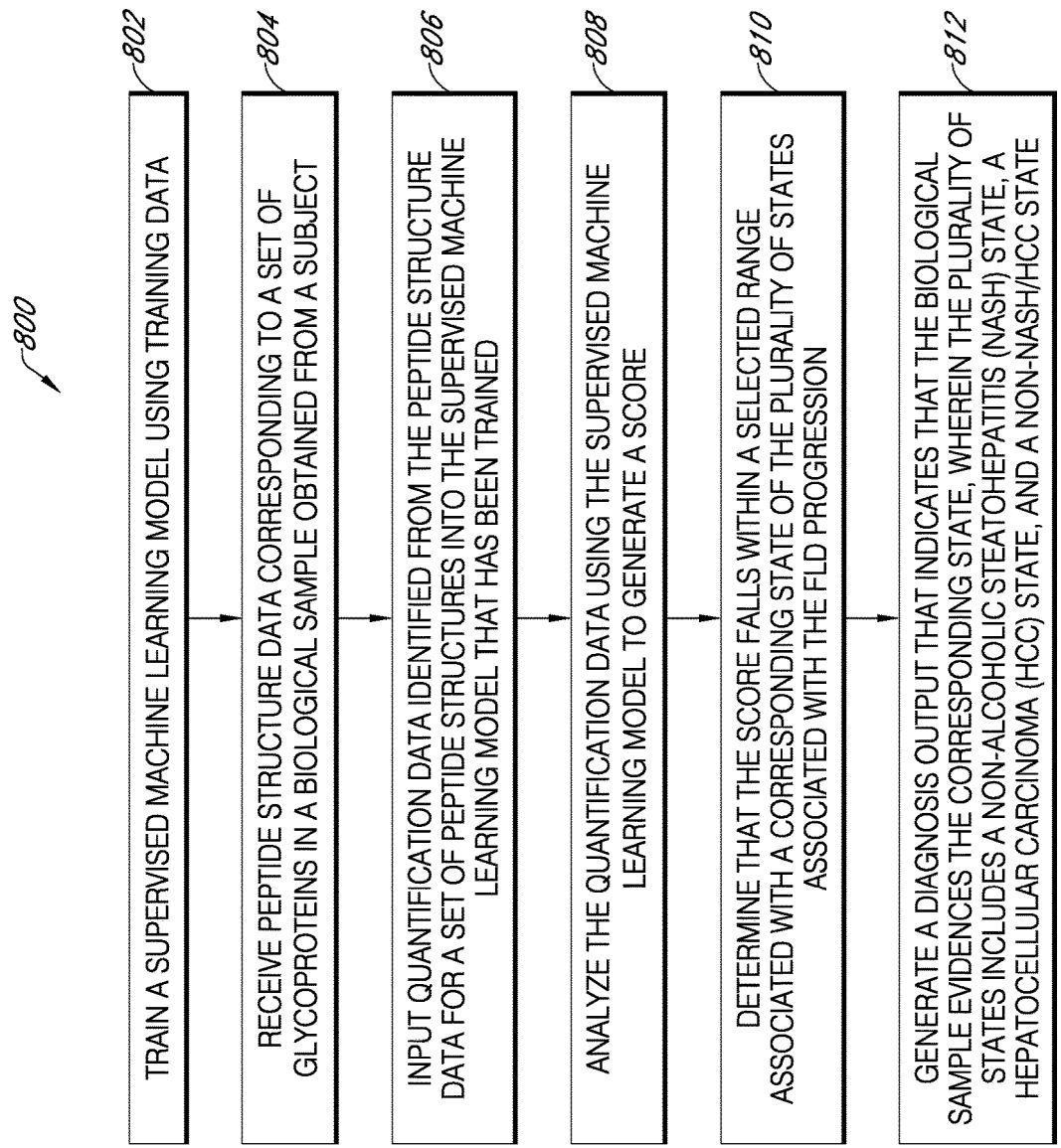
FIG. 8 is a flow chart of a process for classifying a biological sample as corresponding to one of a plurality of states associated with fatty liver disease (FLD) progression in accordance with one or more embodiments.

FIG. 8 is a flow chart of a process for classifying a biological sample as corresponding to one of a plurality of states associated with fatty liver disease (FLD) progression in accordance with one or more embodiments. Process 800 may be implemented using at least a portion of workflow 100 as described FIGS. 1, 2A, and/or 2B and/or analysis system 300 as described in FIG. 3.

Step 802 includes training a supervised machine learning model using training data. In one or more embodiments, the training data comprises a plurality of peptide structure profiles for a plurality of training subjects and identifies a corresponding state of the plurality of states for each peptide structure profile of the plurality of peptide structure profiles.

Step 804 includes receiving peptide structure data corresponding to a set of glycoproteins in the biological sample obtained from a subject.

Step 806 includes inputting quantification data identified from the peptide structure data for a set of peptide structures into the supervised machine learning model that has been trained. In some embodiments, the set of peptide structures includes at least one peptide structure identified in Table 1.

Step 808 includes analyzing the quantification data using the supervised machine learning model to generate a score.

Step 810 includes determining that the score falls within a selected range associated with a corresponding state of the plurality of states associated with the FLD progression.

Step 812 includes generating a diagnosis output that indicates that the biological sample evidences the corresponding state. In some embodiments, the plurality of states includes a non-alcoholic steatohepatitis (NASH) state, a hepatocellular carcinoma (HCC) state, and a non-NASH/HCC (e.g., control or healthy) state.

VII. Exemplary Methodologies for Treatment

VII.A. Treating NASH

Figure 9:
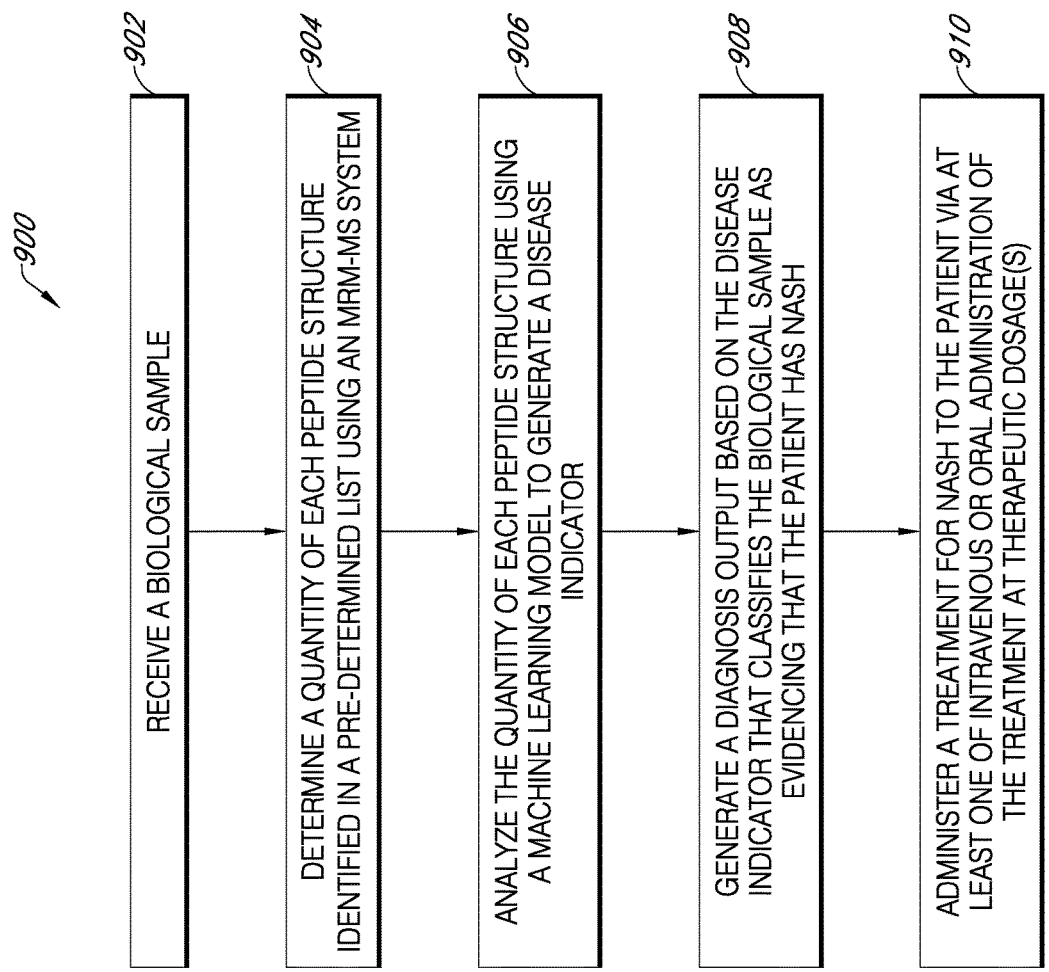
FIG. 9 is a flowchart of a process for treating a subject for NASH in accordance with one or more embodiments.

FIG. 9 is a flowchart of a process for treating a subject for NASH in accordance with one or more embodiments. Process 900 may be at least partially implemented using at least a portion of workflow 100 as described FIGS. 1, 2A, and/or 2B and/or analysis system 300 as described in FIG. 3.

Step 902 includes receiving a biological sample. The biological sample may be one that is obtained from a patient.

Step 904 includes determining a quantity of each peptide structure identified in a predetermined list using an MRM-MS system. The predetermined list may be, for example, the list identified in Table 1 or the list identified in Table 2.

Step 906 includes analyzing the quantity of each peptide structure using a machine learning model to generate a disease indicator.

Step 908 includes generating a diagnosis output based on the disease indicator that classifies the biological sample as evidencing that the patient has NASH (or the NASH disorder).

Step 910 includes administering a treatment for NASH to the patient via at least one of intravenous or oral administration of the treatment at therapeutic dosage(s). The treatment may be comprised of one or more therapeutics or derivatives thereof.

The treatment may include, for example, without limitation, at least one compound or derivative thereof selected from the group consisting of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02. In one or more embodiments, a therapeutic dosage for Obeticholic acid (OCA) may include a dosage within a range of 10-25 mg daily.

Process 900 may include one or more additional steps. For example, process 900 may further include de signing the therapeutic for treating the subject in re Spon seto determining that the biological sample obtained from the subject evidences NASH. Process 900 may include generating a treatment plan for treating the subject in response to determining that the biological sample obtained from the subject evidences NASH.

VII.B. Treating HCC

Figure 10:
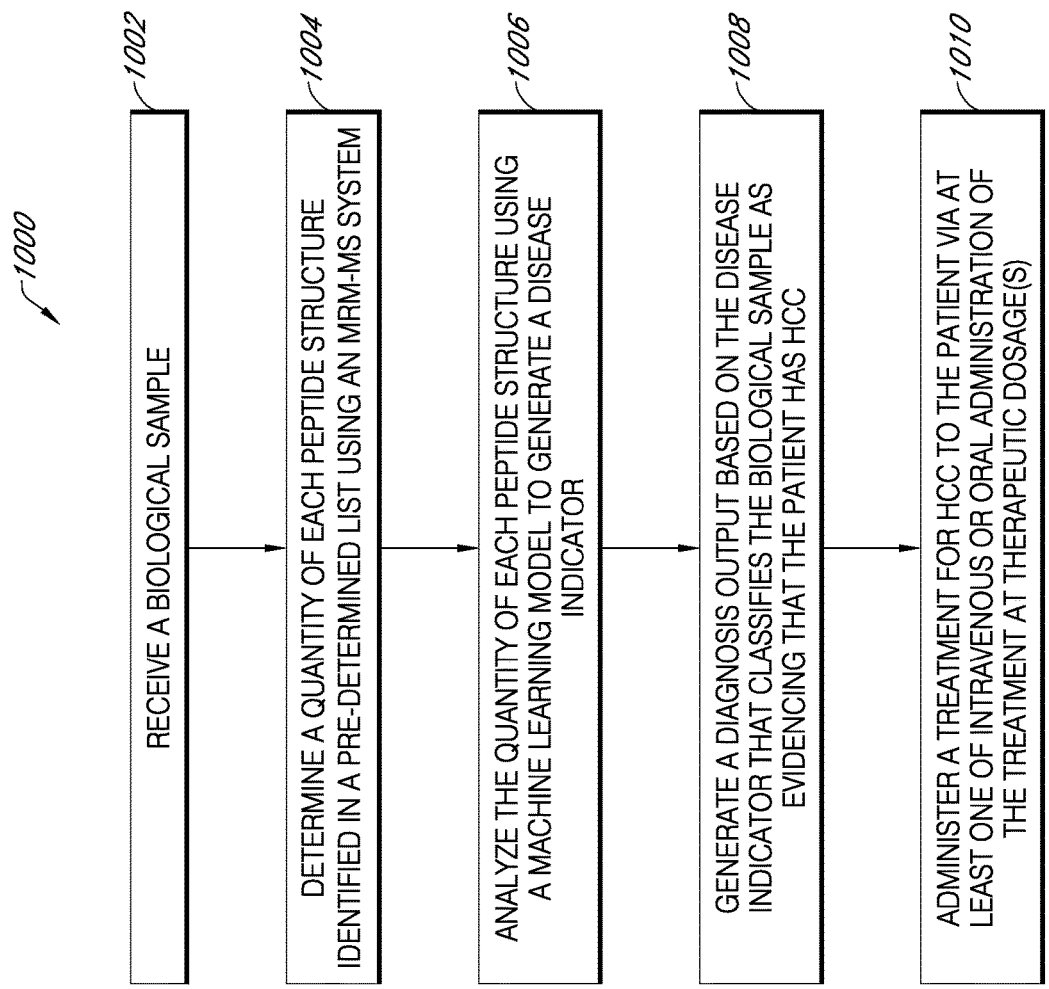
FIG. 10 is a flowchart of a process for treating a subject for NASH in accordance with one or more embodiments.

FIG. 10 is a flowchart of a process for treating a subject for HCC in accordance with one or more embodiments. Process 1000 may be at least partially implemented using at least a portion of workflow 100 as described FIGS. 1, 2A, and/or 2B and/or analysis system 300 as described in FIG. 3.

Step 1002 includes receiving a biological sample. The biological sample may be one that is obtained from a patient.

Step 1004 includes determining a quantity of each peptide structure identified in a predetermined list using an MRM-MS system. The predetermined list may be, for example, the list identified in Table 1 or the list identified in Table 2.

Step 1006 includes analyzing the quantity of each peptide structure using a machine learning model to generate a disease indicator.

Step 1008 includes generating a diagnosis output based on the disease indicator that classifies the biological sample as evidencing that the patient has the HCC disorder.

Step 1010 includes administering a treatment for HCC to the patient via at least one of intravenous or oral administration of the treatment at therapeutic dosage(s). The treatment may be comprised of one or more therapeutics or derivatives thereof.

The treatment may include, for example, without limitation, at least one compound or derivative thereof selected from the group consisting of Atezolizumab, Bevacizumab, Sorafenib (e.g., Sorafenib Tosylate), Lenvatinib (e.g., Lenvatinib Mesylate), Nivolumab, Regorafenib, Cabozantinib (e.g., Cabozantinib-S-Malate), Pemigatinib, Ramucirumab, or Pembrolizumab. In one or more embodiments, step 1010 includes administering Sorafenib or a derivative thereof to the patient via at least one of intravenous or oral administration in a range of 775-825 mg daily. In one or more embodiments, step 1010 includes administering Lenvatinib or a derivative thereof to the patient via at least one of intravenous or oral administration in a range of 7.5-8.5 mg/day when the patient weighs <60 kg and 11.5-12.5 mg/day when the patient weighs >60 kg. In one or more embodiments, step 1010 includes administering Nivolumab or a derivative thereof to the patient via at least one of intravenous or oral administration in a range of 0.75-1.25 mg/kg. In one or more embodiments, step 1010 includes administering Regorafenib or a derivative thereofto the patient via oral administration in a range of 150-170 mg/day. In one or more embodiments, step 1010 includes administering Cabozantinib or a derivative thereof to the patient via at least one of intravenous or oral administration in a range of 50-70 mg/day. In one or more embodiments, step 1010 includes administering Ramucirumab or a derivative thereofto the patient via at least one of intravenous or oral administration in a range of 8-12 mg/kg.

Process 1000 may include one or more additional steps. For example, process 1000 may further include designing the therapeutic for treating the subject in response to determining that the biological sample obtained from the subject evidences HCC. Process 900 may include generating a treatment plan for treating the subject in response to determining that the biological sample obtained from the subject evidences HCC.

VIII. Peptide Structure and Product Ion Compositions, Kits, and Reagents

Aspects of the disclosure include compositions comprising one or more of the peptide structures listed in Table 1. In some embodiments, a composition comprises a plurality of the peptide structures listed in Table 1. In some embodiments, a composition comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or all 53 of the peptide structures listed in Table 1. In some embodiments, a composition comprises a peptide structure having an amino acid sequence with at least 80% sequence identity, such as, for example, at least 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 23-52, listed in Table 1.

Aspects of the disclosure include compositions comprising one or more precursor ions having a defined charge and/or defined mass-to-charge (m/z) ratio, as listed in Table 4 below. Aspects of the disclosure include compositions comprising one or more product ions having a defined mass-to-charge (m/z) ratio, which product ions are produced by converting a peptide structure described herein (e.g., a peptide structure listed in Table 1) into a gas phase ion in a mass spectrometry system. Conversion of the peptide structure into a gas phase ion can take place using any of a variety of techniques, including, but not limited to, matrix assisted laser desorption ionization (MALDI); electron ionization (EI); electrospray ionization (ESI); atmospheric pressure chemical ionization (APCI); and/or atmospheric pressure photo ionization (APPI).

Aspects of the disclosure include compositions comprising one or more product ions produced from one or more of the peptide structures described herein (e.g., a peptide structure listed in Table 1). In some embodiments, a composition comprises a set of the product ions listed in Table 4, having an m/z ratio selected from the list provided for each peptide structure in Table 4.

In some embodiments, a composition comprises at least one of peptide structures PS-1 to PS-53 identified in Table 1.

In some embodiments, a composition comprises a peptide structure or a product ion. The peptide structure or product ion comprises an amino acid sequence having at least 90% sequence identity to any one of SEQ ID NOS: 23-52, as identified in Table 5 below, corresponding to peptide structures PS-1 to PS-53 in Table 1.

In some embodiments, the product ion is selected as one from a group consisting of product ions identified in Table 4, including product ions falling within an identified m/z range of the m/z ratio identified in Table 4 and characterized as having a precursor ion having an m/z ratio within an identified m/z range of the m/z ratio identified in Table 4. A first range for the product ion m/z ratio may be ±0.5. A second range for the product ion m/z ratio may be ±0.8. A third range for the product ion m/z ratio may be ±1.0. A first range for the precursor ion m/z ratio may be ±1.0; a second range for the precursor ion m/z ratio may be (±1.5). Thus, a composition may include a product ion having an m/z ratio that falls within at least one of the first range (±0.5), the second range (±0.8), or the third range (±1.0) of the product ion m/z ratio identified in Table 4, and may be characterized as having a precursor ion having an m/z ratio that falls within at least one of the first range (±0.5), the second range (±1.0), or the third range (±1.0 of the precursor ion m/z ratio identified in Table 4.

In Table 4, "PS-ID No." identifies the label or index for the peptide structure; "R; "RT (min)" identifies the minimum retention time; "Coll. Energy" identifies the collision energy; "Precur. m/z" identifies the precursor ion m/z ratio; "Precur. Charge" identifies the precursor ion charge; "1$^{st}$ Prod. m/z" identifies the first product ion m/z ratio; "1$^{st}$ Prod. Charge" identifies the first product ion charge; "2$^{nd}$ Prod. m/z" identifies the second product ion m/z ratio; "2$^{nd}$ Prod. Charge" identifies the second product ion charge.

TABLE 4

Peptide Structures and Mass Spectrometry-Related Characteristics

| PS-ID NO. | RT (min) | Coll. Energy | Precur. m/z | Precur. Charge | 1st Prod. m/z | 1st Prod. Charge | 2nd Prod. m/z | 2nd Prod. Charge |
|---|---|---|---|---|---|---|---|---|
| PS-1 | 37.5 | 30 | 1224.5 | 3 | 366.1 | 1 | 980 | 2 |
| PS-2 | 38.3 | 24 | 991.2 | 4 | 366.1 | 1 | 980.5 | 2 |
| PS-3 | 33.15 | 15 | 1209.7 | 5 | 1347.9 | 3 | 366.1 | 1 |
| PS-4 | 18.54 | 20 | 628.3 | 2 | 1071.5 | 1 | 738.4 | 1 |
| PS-5 | 32.56 | 30 | 836.9 | 2 | 721.9 | 2 | 1305.7 | 1 |
| PS-6 | 44.1 | 22 | 1093.2 | 4 | 366.1 | 1 | 1183.6 | 2 |
| PS-7 | 38.9 | 25 | 1239.1 | 4 | 1314.2 | 3 | N/A | N/A |
| PS-8 | 39.3 | 30 | 1413.6 | 4 | 366.1 | 1 | 1313.3 | 3 |
| PS-9 | 39.9 | 26 | 1189.2 | 5 | 366.1 | 1 | N/A | N/A |
| PS-10 | 42.1 | 25 | 1151.7 | 4 | 366.1 | 1 | 1300.7 | 2 |
| PS-11 | 41.5 | 22 | 1115.4 | 4 | 366.1 | 1 | N/A | N/A |
| PS-12 | 42 | 25 | 1188.2 | 4 | 366.1 | 1 | N/A | N/A |
| PS-13 | 34.6 | 23 | 1158.8 | 4 | 1206.9 | 3 | 366.1 | 1 |
| PS-14 | 34.5 | 30 | 1199.3 | 4 | 1206.9 | 3 | 366.1 | 1 |
| PS-15 | 34.4 | 24 | 1249.6 | 4 | 366.1 | 1 | 1206.9 | 3 |
| PS-16 | 41.4 | 20 | 1206.3 | 7 | 366.1 | 1 | N/A | N/A |
| PS-17 | 38.4 | 30 | 1184.9 | 5 | 274.1 | 1 | N/A | N/A |
| PS-18 | 11.4 | 20 | 851.1 | 4 | 366.1 | 1 | 1398.6 | 1 |
| PS-19 | 38.1 | 30 | 1196.5 | 4 | 366.1 | 1 | N/A | N/A |
| PS-20 | 23 | 28 | 1122.5 | 4 | 366.1 | 1 | 1060 | 2 |
| PS-21 | 38.2 | 20 | 1028.8 | 3 | 274.1 | 1 | 1069 | 2 |
| PS-22 | 38.1 | 27 | 1096.5 | 3 | 274.1 | 1 | N/A | N/A |
| PS-23 | 37.5 | 23 | 970.1 | 3 | 366.1 | 1 | N/A | N/A |
| PS-24 | 37 | 22 | 937.4 | 3 | 366.1 | 1 | N/A | N/A |
| PS-25 | 34.7 | 36 | 1185.3 | 4 | 366.1 | 1 | N/A | N/A |
| PS-26 | 6.2 | 25 | 993.1 | 3 | 366.1 | 1 | N/A | N/A |
| PS-27 | 23.3 | 33 | 991.4 | 4 | 366.1 | 1 | N/A | N/A |
| PS-28 | 17.5 | 34 | 1103.8 | 3 | 366.1 | 1 | 1307.7 | 1 |
| PS-29 | 15 | 32 | 1020 | 2 | 366.1 | 1 | N/A | N/A |
| PS-30 | 15 | 27 | 815.7 | 3 | 366.1 | 1 | N/A | N/A |
| PS-31 | 14.1 | 45 | 850.7 | 3 | 366.1 | 1 | N/A | N/A |
| PS-32 | 13.5 | 32 | 1034.8 | 3 | 366.1 | 1 | N/A | N/A |
| PS-33 | 13.1 | 27 | 1116.4 | 5 | 366.1 | 1 | N/A | N/A |
| PS-34 | 13.2 | 31 | 1247.7 | 5 | 366.1 | 1 | N/A | N/A |
| PS-35 | 13.3 | 35 | 1378.9 | 5 | 366.1 | 1 | N/A | N/A |
| PS-36 | 29.3 | 31 | 1237.3 | 3 | 366.1 | 1 | 999.5 | 2 |
| PS-37 | 30.5 | 24 | 1001.2 | 4 | 366.1 | 1 | 999.5 | 2 |
| PS-38 | 29.2 | 30 | 1015.5 | 4 | 366.1 | 1 | 999.5 | 2 |
| PS-39 | 30.3 | 20 | 1092.3 | 4 | 366.1 | 1 | N/A | N/A |
| PS-40 | 12.4 | 24 | 977.8 | 3 | 366.1 | 1 | N/A | N/A |
| PS-41 | 8.3 | 27 | 1084.1 | 4 | 366.1 | 1 | 1392.6 | 1 |
| PS-42 | 13.2 | 21 | 873.4 | 3 | 204.1 | 1 | 1360.6 | 1 |
| PS-43 | 14 | 30 | 1019.4 | 3 | 204.1 | 1 | 1360.6 | 1 |
| PS-44 | 25.5 | 30 | 1064.4 | 4 | 366.1 | 1 | 1271.6 | 2 |
| PS-45 | 31.9 | 25 | 1041.5 | 4 | 366.1 | 1 | N/A | N/A |
| PS-46 | 33.1 | 35 | 1114.2 | 4 | 204.1 | 1 | 1225.6 | 2 |
| PS-47 | 30.4 | 20 | 1004.7 | 4 | 366.1 | 1 | N/A | N/A |
| PS-48 | 33.7 | 38 | 1277.8 | 4 | 366.1 | 1 | N/A | N/A |
| PS-49 | 27.3 | 22 | 921.4 | 4 | 366.1 | 1 | N/A | N/A |
| PS-50 | 25.9 | 20 | 1252.5 | 3 | 366.1 | 1 | 840.4 | 2 |
| PS-51 | 26.9 | 25 | 1012.7 | 4 | 366.1 | 1 | 840.4 | 2 |
| PS-52 | 24 | 23 | 942.4 | 3 | 366.1 | 1 | 1114.6 | 1 |
| PS-53 | 27.5 | 30 | 1068.7 | 4 | 366.1 | 1 | N/A | N/A |

Table 5 defines the peptide sequences for SEQ ID NOS: 23-52 from Table 1. Table 5 further identifies a corresponding protein SEQ ID NO for each peptide sequence. The corresponding protein SEQ ID NO identifies the protein from which the peptide sequence may be derived.

TABLE 5

Peptide SEQ ID NOS

| SEQ ID NO: | Peptide Sequence | Corresponding Protein SEQ ID NO: |
|---|---|---|
| 23 | YLGNATAIFFLPDEGK | 1 |
| 24 | EGDHEFLEVPEAQEDVEATFPVHQPGNYSCSYR | 2 |

TABLE 5-continued

Peptide SEQ ID NOS

| SEQ ID NO: | Peptide Sequence | Corresponding Protein SEQ ID NO: |
|---|---|---|
| 25 | AIGYLNTGYQR | 3 |
| 26 | TEHPFTVEEFVLPK | 3 |
| 27 | VSNQTLSLFFTVLQDVPVR | 3 |
| 28 | IITILEEEMNVSVCGLYTYGKPVPGHVTVSICR | 3 |
| 29 | GCVLLSYLNETVTVSASLESVR | 3 |
| 30 | SLGNVNFTVSAEALESQELCGTEVPSVPEHGR | 3 |
| 31 | ASVSVLGDILGSAMQNTQNLLQMPYGCGEQNMVLFAPNIYVLDYLNETQQLTPEIK | 3 |
| 32 | FNLTETSEAEIHQSFQHLLR | 4 |
| 33 | DIENFNSTQK | 5 |
| 34 | QIPLCANLVPVPITNATLDQITGK | 6 |
| 35 | QDQCIYNTTYLNVQR | 6 |
| 36 | FSEFWDLDPEVRPTSAVAA | 7 |
| 37 | TELESSSCPGGIMLNETGQGYQR | 8 |
| 38 | NGTAVCATNR | 9 |
| 39 | LANLTQGEDQYYLR | 10 |
| 40 | GLNVTLSSTGR | 11 |
| 41 | VLNFTTK | 12 |
| 42 | GGSSGWSGGLAQNR | 13 |
| 43 | NLFLNHSENATAK | 14 |
| 44 | VVLHPNYSQVDIGLIK | 14 |
| 45 | TPLTANITK | 15 |
| 46 | EEQYNSTYR | 16 |
| 47 | EEQFNSTFR | 17 |
| 48 | GLTFQQNASSMCVPDQDTAIR | 18 |
| 49 | LQAPLNYTEFQKPICLPSK | 19 |
| 50 | CGLVPVLAENYNK | 20 |
| 51 | NGSLFAFR | 21 |
| 52 | DIVEYYNDSNGSHVLQGR | 22 |

Table 6 identifies the proteins of SEQ ID NOS: 1-22 from Table 1. Table 6 identifies a corresponding protein abbreviation and protein name for each of protein SEQ ID NOS: 1-22. Further, Table 6 identifies a corresponding Uniprot ID for each of protein SEQ ID NOS: 1-22.

TABLE 6

Protein SEQ ID NOS

| SEQ ID NO. | Protein Abbreviation | Protein Name | Uniprot ID |
|---|---|---|---|
| 1 | A1AT | Alpha-1 Antitrypsin | P01009 |
| 2 | A1BG | Alpha-1-B Glycoprotein | P04217 |
| 3 | A2MG | Alpha-2-Macroglobulin | P01023 |
| 4 | AACT | Alpha 1-Antichymotrypsin | P01011 |
| 5 | AFAM | Afamin | P43652 |
| 6 | AGP1 | Alpha-1-acid glycoprotein 1 | P02763 |
| 7 | APOC3 | Apolipoprotein C-III | P02656 |
| 8 | APOM | Apolipoprotein M | O95445 |
| 9 | CFAI | Complement Factor I | P05156 |
| 10 | CLUS | Clusterin | P10909 |
| 11 | CO4A | Complement C4-alpha | P0C0L4 |
| 12 | CO6 | Complement component C6 | P13671 |
| 13 | CO8A | Complement C8-alpha | P07357 |
| 14 | HPT | Haptoglobin | P00738 |
| 15 | IGA2 | Immunoglobulin alpha-2 | P01877 |
| 16 | IGG1 | Immunoglobulin gamma-1 | P01857 |
| 17 | IGG2 | Immunoglobulin gamma-2 | P01859 |
| 18 | IGM | Immunoglobulin M | P01871 |
| 19 | KLKB1 | Prekallikrein | P03952 |
| 20 | TRFE | Transferrin | P02787 |
| 21 | VTNC | Vitronectin | P04004 |
| 22 | ZA2G | Zinc-alpha-2-glycoprotein | P25311 |

Table 7 identifies and defines the glycan structures included in Table 1. Table 7 identifies a graphical representation of the one or more glycan structures associated with a particular glycan and a coded representation of the composition for each glycan structure included in Table 1. As used herein, the 4-digit GL NO. is a designation that represents the number of hexoses, the number of HexNAcs, the number of Fucoses, and the number of Neuraminic Acids.

TABLE 7

Glycan Structure GL NOS: Structure and Composition

| Glycan Structure GL | Structure NO. | Composition |
|---|---|---|
| 1102 | | Hex(1)HexNAc(1)Fuc(0)NeuAc(2) |
| 1202 | | Hex(1)HexNAc(2)Fuc(0)NeuAc(2) |
| 1300 | | Hex(1)HexNAc(3)Fuc(0)NeuAc(0) |
| 2110 | | Hex(2)HexNAc(1)Fuc(1)NeuAc(0) |
| 4400 | | Hex(4)HexNAc(4)Fuc(0)NeuAc(0) |
| 4411 | | Hex(4)HexNAc(4)Fuc(1)NeuAc(1) |
| 5200 | | Hex(5)HexNAc(2)Fuc(0)NeuAc(0) |
| 5400 | | Hex(5)HexNAc(4)Fuc(0)NeuAc(0) |
| 5401 | | Hex(5)HexNAc(4)Fuc(0)NeuAc(1) |
| 5402 | | Hex(5)HexNAc(4)Fuc(0)NeuAc(2) |
| 5410 | | Hex(5)HexNAc(4)Fuc(1)NeuAc(0) |
| 5411 | | Hex(5)HexNAc(4)Fuc(1)NeuAc(1) |
| 5412 | | Hex(5)HexNAc(4)Fuc(1)NeuAc(2) |

TABLE 7-continued

Glycan Structure GL NOS: Structure and Composition

| Glycan Structure GL | Structure NO. | Composition |
|---|---|---|
| 5421 | | Hex(5)HexNAc(4)Fuc(2)NeuAc(1) |
| 5431 | | Hex(5)HexNAc(4)Fuc(3)NeuAc(1) |
| 5510 | | Hex(5)HexNAc(5)Fuc(1)NeuAc(0) |
| 5511 | | Hex(5)HexNAc(5)Fuc(1)NeuAc(1) |
| 6200 | | Hex(6)HexNAc(2)Fuc(0)NeuAc(0) |
| 6300 | | Hex(6)HexNAc(3)Fuc(0)NeuAc(0) |
| 6501 | | Hex(6)HexNAc(5)Fuc(0)NeuAc(1) |
| 6502 | | Hex(6)HexNAc(5)Fuc(0)NeuAc(2) |
| 6503 | | Hex(6)HexNAc(5)Fuc(0)NeuAc(3) |
| 6512 | | Hex(6)HexNAc(5)Fuc(1)NeuAc(2) |
| 6513 | | Hex(6)HexNAc(5)Fuc(1)NeuAc(3) |
| 7601 | | Hex(7)HexNAc(6)Fuc(0)NeuAc(1) |
| 7604 | | Hex(7)HexNAc(6)Fuc(0)NeuAc(4) |
| 7613 | | Hex(7)HexNAc(6)Fuc(1)NeuAc(3) |
| 7614 | | Hex(7)HexNAc(6)Fuc(1)NeuAc(4) |
| 10803 | | Hex(5)HexNAc(4)Fuc(0)NeuAc(1) + Hex(5)HexNAc(4)Fuc(0)NeuAc(2) |
| 11904 | | Hex(5)HexNAc(4)Fuc(0)NeuAc(2) + Hex(6)HexNAc(5)Fuc(0)NeuAc(2) |
| 121005 | | Hex(6)HexNAc(5)Fuc(0)NeuAc(2) + Hex(6)HexNAc(5)Fuc(0)NeuAc(3) |
| 121015 | | Hex(6)HexNAc(5)Fuc(0)NeuAc(2) + Hex(7)HexNAc(6)Fuc(1)NeuAc(3) |

Legend for Table 7

| ● | ○ | ◉ | ▲ | ◆ |
|---|---|---|---|---|
| Glc | Gal | Man | Fuc | Neu5Ac |
| ■ | □ | ▨ | ★ | ◆ |
| GlcNAc | GalNAc | ManNAc | Xyl | Neu5Gc |
| ◤ | ◨ | ▨ | | ◇ |
| GlcN | GalN | ManN | | Kdn |
| ◆ | ◇ | ◈ | ◆ | |
| GlcA | GalA | ManA | IdoA | |

Aspects of the disclosure include kits comprising one or more compositions, each comprising one or more peptide structures of the disclosure that can be used as assay standards, and instructions for use. Kits in accordance with one or more embodiments described herein may include a label indicating the intended use of the contents of the kit. The term "label" as used herein with respect to a kit includes any writing, or recorded material supplied on or with a kit, or that otherwise accompanies a kit.

The peptide structures and the transitions produced therefrom, as described herein, may be useful for diagnosing and treating various disease states within FLD, including, without limitation, NASH and HCC. A transition includes a precursor ion and at least one product ion grouping. As described herein, the peptide structures in Table 1, as well as their corresponding precursor ion and production groupings (these ions having defined m/z ratios or m/z ratios that fall within the m/z ranges identified herein), can be used in mass spectrometry-based analyses to diagnose and facilitate treatment of diseases, such as, for example, NASH and HCC.

Aspects of the disclosure include methods for analyzing one or more peptide structures, as described herein. In some embodiments, the methods involve processing a sample from a patient to generate a prepared sample that can be inputted into a mass spectrometry system (e.g., a reaction monitoring mass spectrometry system) using, for example, a liquid chromatography system (e.g., a high-performance liquid chromatography system (HPLC)). In certain embodiments, processing the sample can comprise performing one or more of: a denaturation procedure, a reduction procedure, an alkylation procedure, and a digestion procedure. The denaturation and reduction procedures may be implemented in a manner similar to, for example, denaturation and reduction 202 in FIG. 2. The alkylation procedure may be implemented in a manner similar to, for example, alkylation procedure 204 in FIG. 2. The digestion procedure may be implemented in a manner similar to, for example, digestion procedure 206 in FIG. 2.

In some embodiments, the methods for analyzing one or more peptide structures involve detecting a set of productions generated by a mass spectrometry system (e.g., a reaction monitoring mass spectrometry system) in which one or more product ions may correspond to each of the one or more peptide structures that have been inputted into the mass spectrometry system. As described herein, each peptide structure can be converted into a set of product ions having a defined m/z ratio, as provided in Table 4, or an m/z ratio within an identified range of the m/z ratio provided in Table 4. In some embodiments, the methods involve generating quantification (e.g., abundance) data for the one or more product ions detected using the mass spectrometry system.

In some embodiments, the methods further comprise generating a diagnosis output using the quantification data and a model that has been trained using supervised and/or unsupervised machine learning. In certain embodiments, the reaction monitoring mass spectrometry system may include multiple/selected reaction monitoring mass spectrometry (MRM/SRM-MS) to detect the one or more product ions and generate the quantification data.

IX. Representative Experimental Results

IXA. Sample Preparation and Mass Spectrometry Data Production

FIG. 11 is a table of the sample population used for the experiments in accordance with one or more embodiments. The samples used to generate the experimental results included serum samples from 23 patients with a biopsy-proven diagnosis of NASH (10 male, 13 female; Indivumed AG, Hamburg, Germany), 20 patients with a diagnosis of HCC (16 male, 4 female; 6 stage I, 8 stage II, 6 stage III, 2 stage IV; Indivumed AG), and 56 healthy subjects with no history of liver disease (control, 26 male, 30 female) which were sourced from iSpecimen, Palleon Pharmaceuticals Inc. and Human Immune Monitoring Center (HIMC) of Stanford. Clinical diagnoses of patients with NASH and HCC were based on histopathological characterization of hepatic tissue obtained either via needle biopsy or at surgery.

FIG. 12 is a table of the sample population used for validation in accordance with one or more embodiments. The validation sample population consisted of serum samples from 28 control subjects diagnosed with a benign hepatic mass (16 male, 12 female) and 28 subjects (20 male, 8 female) diagnosed with HCC, all obtained from Indivumed AG. Clinical diagnoses of patients were based on histopathological characterization of hepatic tissue obtained either via needle biopsy or at surgery.

Prior to analysis, serum samples were reduced with DTT and alkylated with IAA followed by digestion with trypsin in a water bath at 37° C. for 18 hours. To quench the digestion, formic acid was added to each sample after incubation to a final concentration of 1%.

Digested serum samples were injected into a triple quadrupole mass spectrometer (MS) using a liquid chromatography system (e.g., a high-performance liquid chromatography (HPLC) system). Separation of the peptide structures (glycosylated and aglycosylated) was performed using a 70-min binary gradient. The triple quadrupole MS was operated in dynamic multiple reaction monitoring (dMRM) mode. Samples were injected in a randomized fashion with regard to underlying phenotype, and reference pooled serum digests were injected interspersed with study samples, at every 10th sample position throughout the run.

An MRM analysis was performed on the peptide structures, representing a total of 73 high-abundance serum glycoproteins. A transition list consisted of glycopeptide structures as well as aglycosylated peptide structures from each glycoprotein. The python library Scikit-learn (http s://scikit-learn org/stable/) was used for statistical analyses and for building machine learning models.

Normalized abundance data was generated for the peptide structures using the following formula:

Normalized abundance=(raw abundance of a peptide structure in sample/raw abundance of the corresponding aglycosylatedpeptide from the same glycoprotein)/average relative abundance of the same glycopeptides or peptides in the flanking pooled reference serum samples Relative abundance was calculated as the ratio of the raw abundance of any given glycopeptide to the sum of raw abundances of all glycopeptides.

Figure 13:
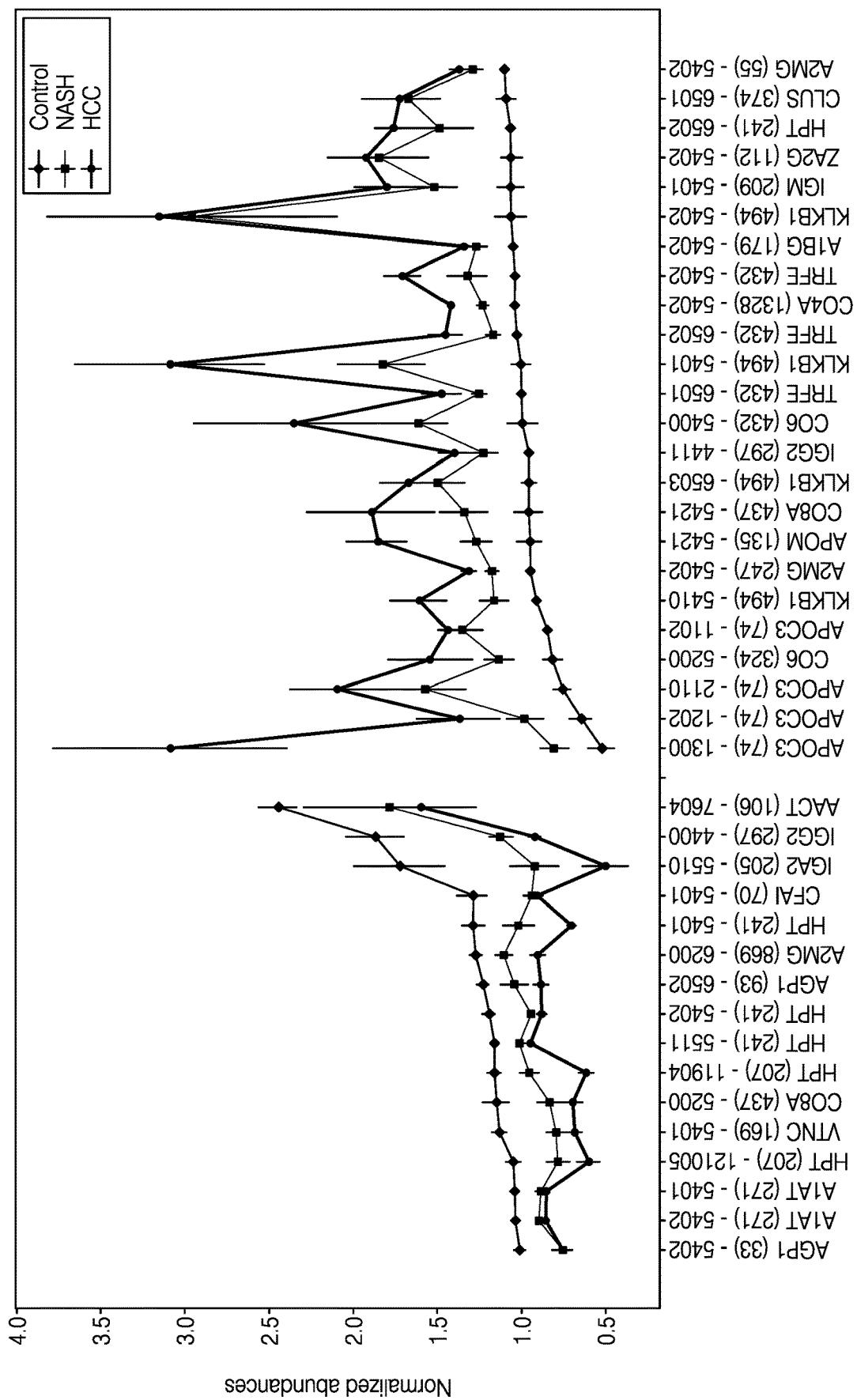
FIG. 13 is an illustration of a plot of the mean normalized abundance for selected peptide structures identified and quantified via mass spectrometry depicted in accordance with one or more embodiments.

IX.B. Analysis of Peptide Structure Data (e.g., Abundance Data) and Confirming their Diagnostic Power FIG. 13 is an illustration of a plot of the mean normalized abundance for selected peptide structures identified and quantified via mass spectrometry depicted in accordance with one or more embodiments. As depicted, changes in the mean normalized abundances for the peptide structures increased or decreased in a single direction for the progression from the control state to the NASH state to the HCC state. This abundance data shows that such peptide structures can be used to distinguish between the control state, the NASH state, and the HCC state.

Figure 14:
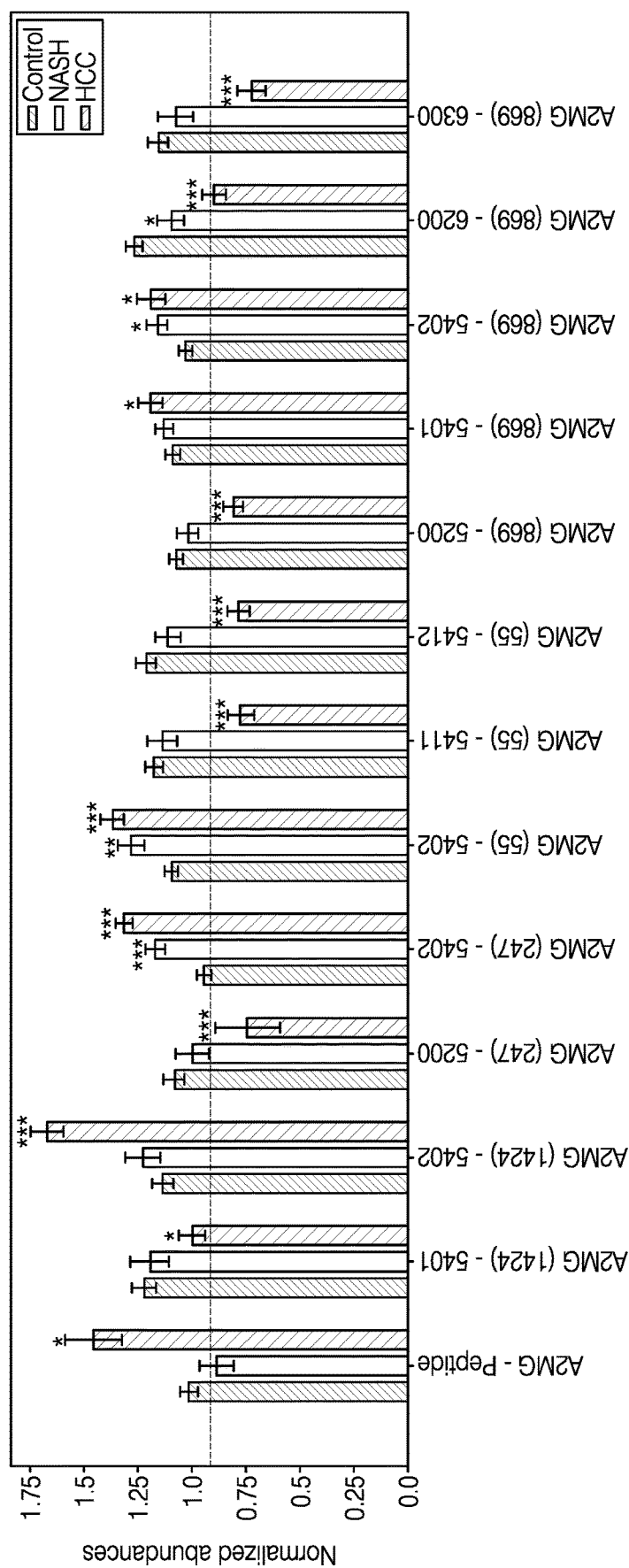
FIG. 14 is an illustration of a plot of the normalized abundances for selected peptide structures of A2MG in accordance with one or more embodiments.

FIG. 14 is an illustration of a plot of the normalized abundances for selected peptide structures of A2MG in accordance with one or more embodiments.

Figure 15:
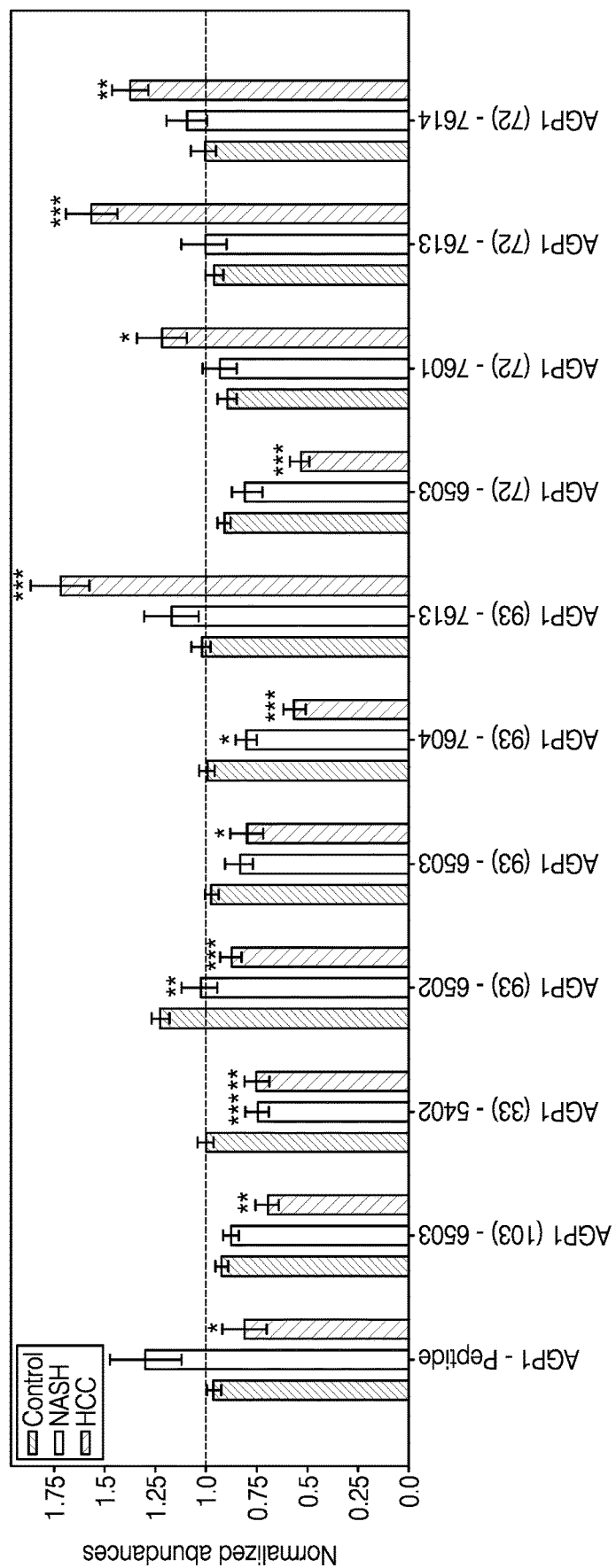
FIG. 15 is an illustration of a plot of the normalized abundances for selected peptide structures of AGP1 in accordance with one or more embodiments.

FIG. 15 is an illustration of a plot of the normalized abundances for selected peptide structures of AGP1 in accordance with one or more embodiments.

Figure 16:
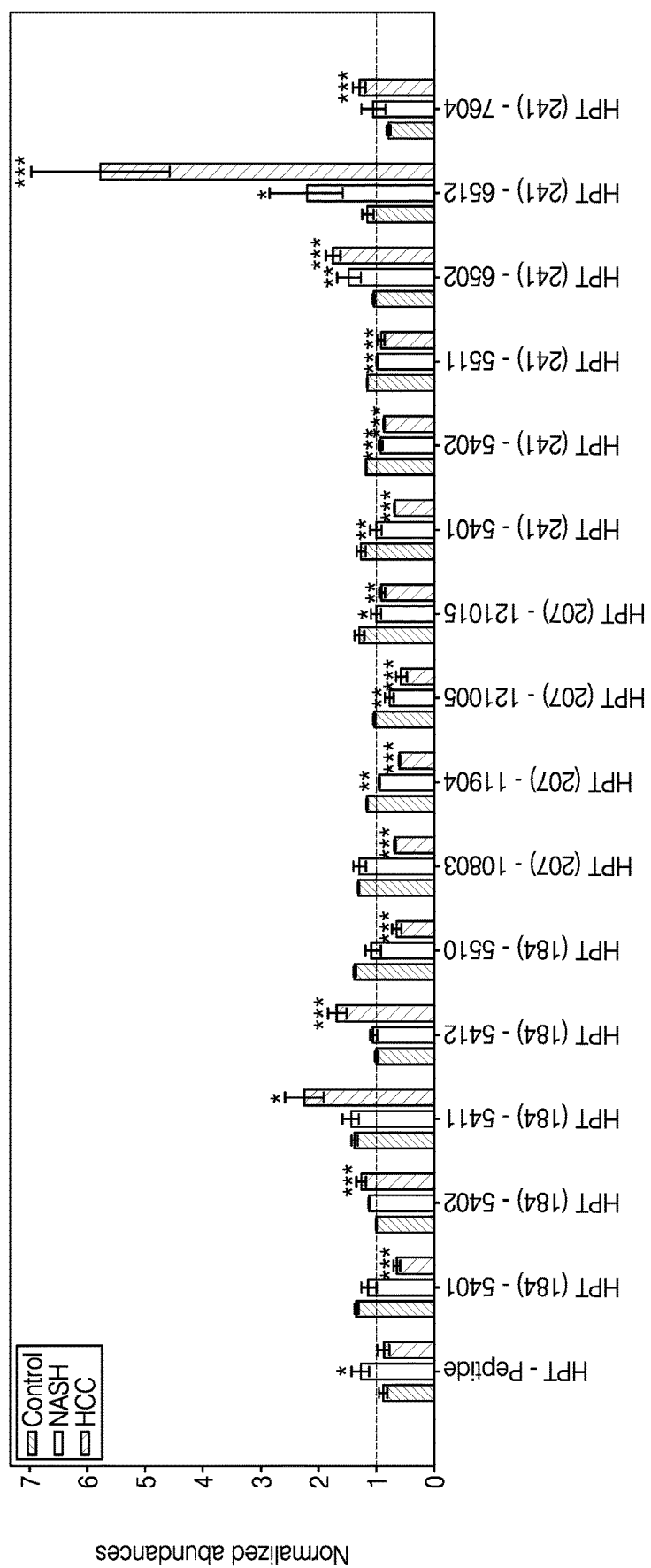
FIG. 16 is an illustration of a plot of the normalized abundances for selected peptide structures of HPT in accordance with one or more embodiments.

FIG. 16 is an illustration of a plot of the normalized abundances for selected peptide structures of HPT in accordance with one or more embodiments.

Figure 17:
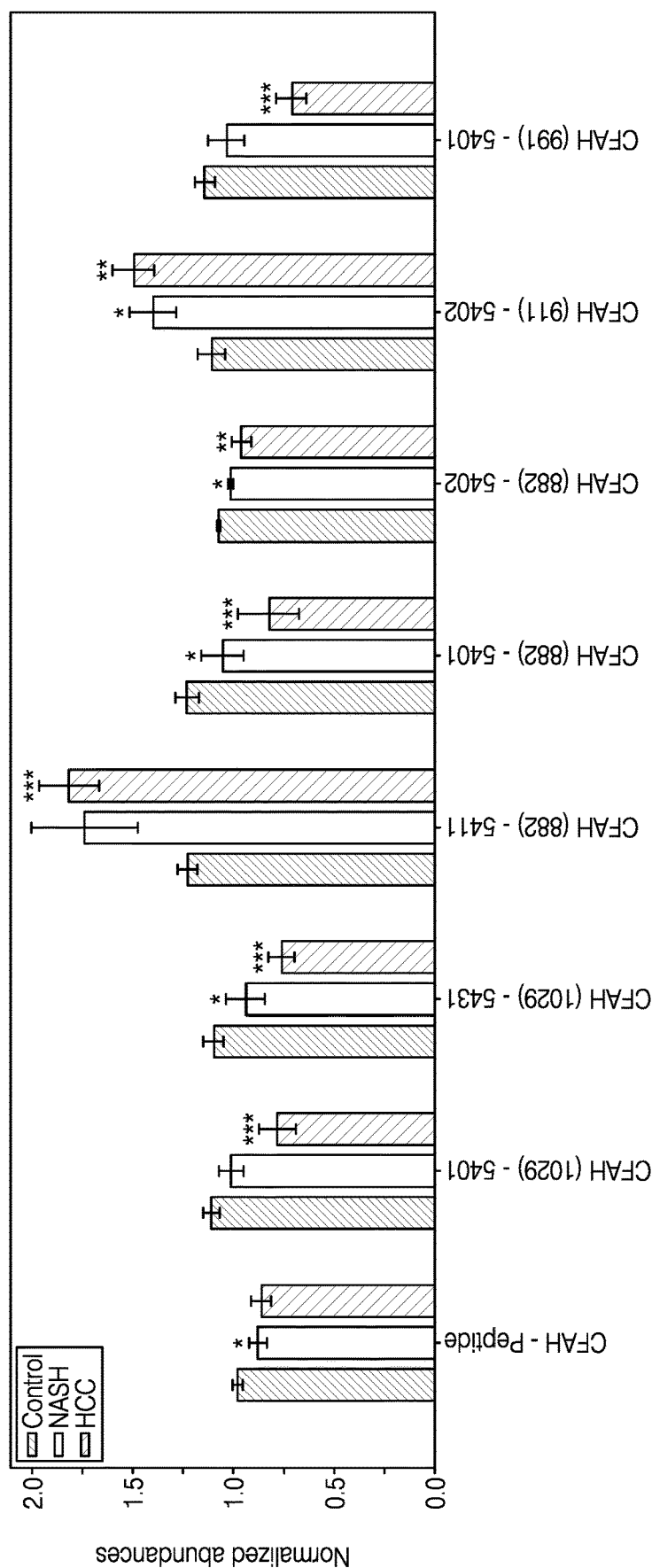
FIG. 17 is an illustration of a plot of the normalized abundances for selected peptide structures of CFAH in accordance with one or more embodiments.

FIG. 17 is an illustration of a plot of the normalized abundances for selected peptide structures of CFAH in accordance with one or more embodiments.

Figure 18:
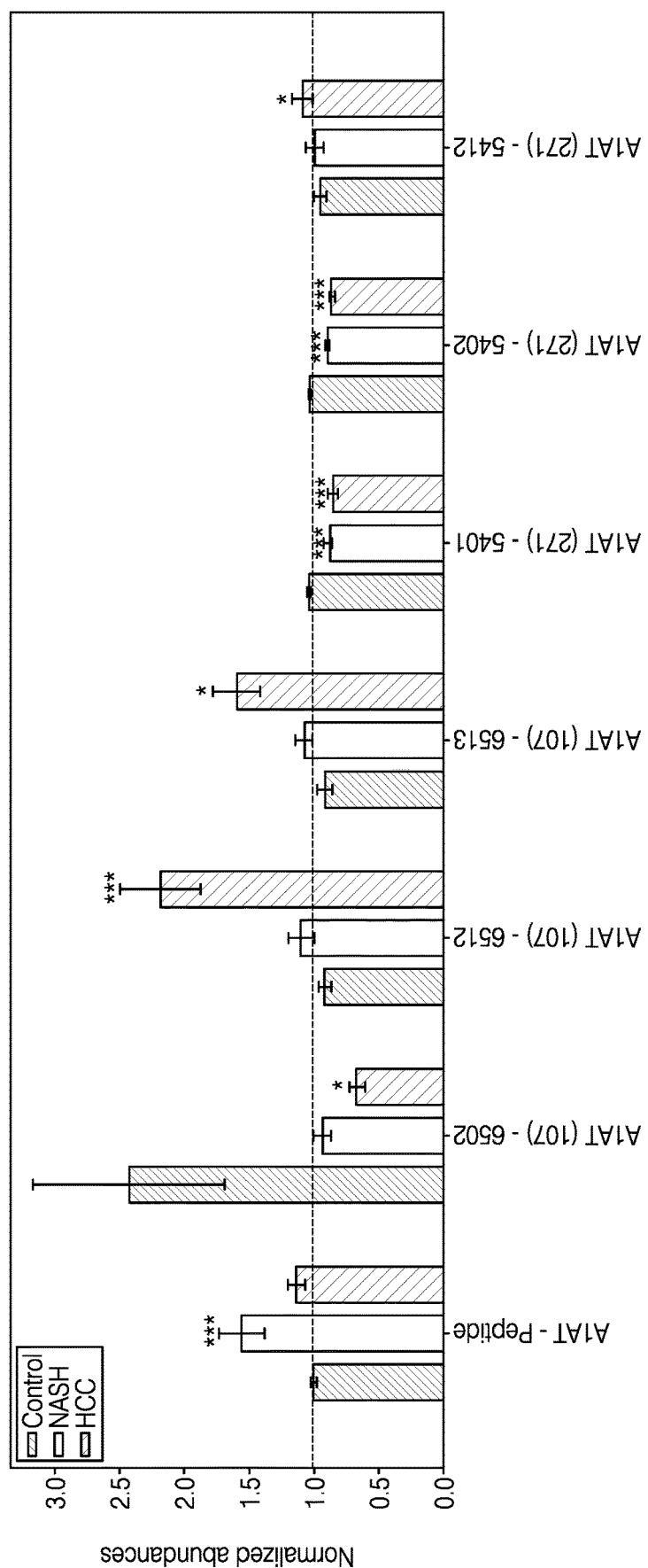
FIG. 18 is an illustration of a plot of the normalized abundances for selected peptide structures of A1AT in accordance with one or more embodiments.

FIG. 18 is an illustration of a plot of the normalized abundances for selected peptide structures of A1AT in accordance with one or more embodiments.

FIGS. 14-18 illustrate that peptide structures for a single glycoprotein (e.g., A2MG, AGP1, HPT, CFAH, A1AT) as well as peptide structures for a combination of such glycoproteins may be useful in diagnosing when a subject has progressed from a non-NASH/HCC (e.g., healthy state) to NASH or from NASH to HCC.

The normalized abundances of various peptide structures (e.g., those peptide structures identified in Table 2) were used to train a first regression model (e.g., Model 1) to generate a disease indicator for a subject. The disease indicator was generated as a score (e.g., probability score) in which the range in which the score falls enables diagnosis or classification as a non-NASH/HCC state (e.g., a control state), a NASH state, or an HCC state.

IX.C. Validation

Figure 19:
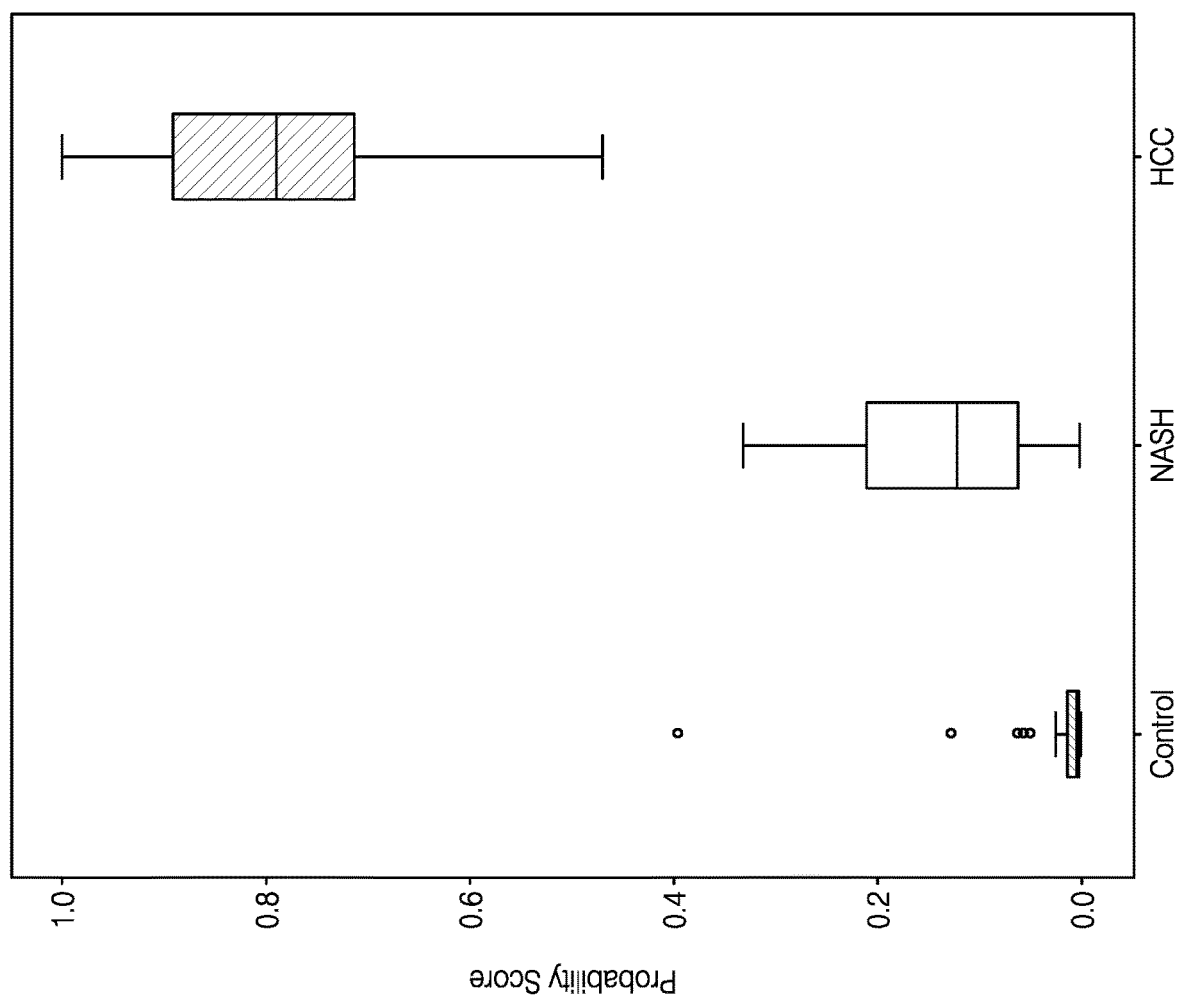
FIG. 19 is a plot diagram illustrating validation of the disease indicator's ability to distinguish between the control state, the NASH state, and the HCC state in accordance with one or more embodiments.

FIG. 19 is a plot diagram illustrating validation of the disease indicator's ability to distinguish between the control state, the NASH state, and the HCC state in accordance with one or more embodiments. As depicted, a disease indicator of about 0.0 to about 0.05 was generally accurate in classifying as a control state; a disease indicator of about 0.05 to about 0.4 was generally accurate in classifying as a NASH state; and a disease indicator of about 0.5 to about 1.00 was generally accurate in classifying as an HCC state.

Figure 20:
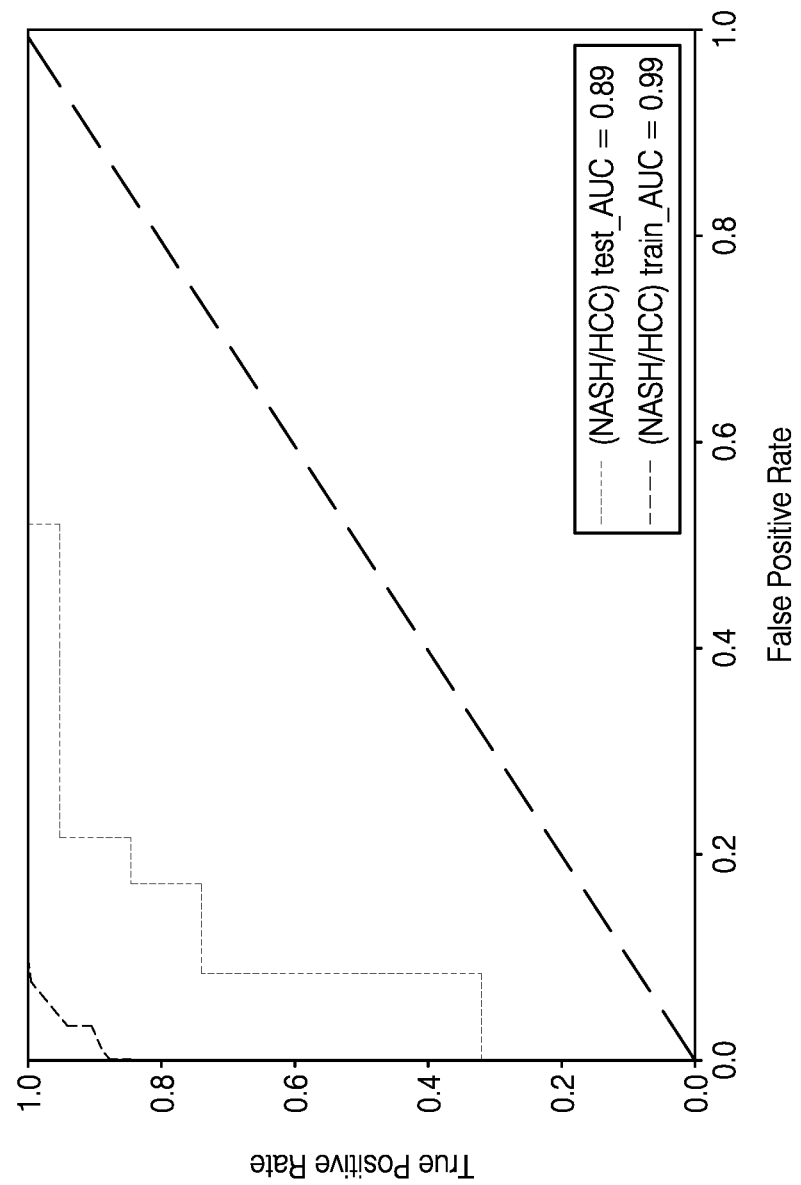
FIG. 20 is a plot diagram of the receiver-operating-characteristic (ROC) curve for distinguishing between the NASH state and the HCC state for both the training and testing sets in accordance with one or more embodiments.

FIG. 20 is a plot diagram of the receiver-operating-characteristic (ROC) curve for distinguishing between the NASH state and the HCC state for both the training and testing sets in accordance with one or more embodiments. Leave one out cross validation (LOOCV) was performed on normalized abundances of the samples from both NASH and HCC patients. A logistic regression model with (LASSO) regularization was iteratively trained on all samples except for one sample that was left out in that iteration. The trained model was then used to predict on the sample that was left out. As shown in FIG. 20, the area under the ROC curve (AUROC) for the training set was found to be 0.99, while the AUROC for the testing set was found to be 0.89.

IX.C.1. Validation Using the Second Sample Population

To validate the ability of peptide structures in distinguishing between HCC and other states, a second sample population (see FIG. 12) was analyzed using a second regression model (Model 2). Model 2 was trained using a smaller set of peptide structures to distinguish between HCC and benign hepatic mass. For example, the subjects used as controls were individuals with a diagnosis of a benign hepatic mass. This enabled directly assessing the discriminant power of differential peptide structure abundance for HCC.

Analysis was conducted for 10 peptide structures (8 glycopeptide structures and 2 peptide structures). The 10 peptide structures were all associated with A2MG. Model 2 was built using least absolute shrinkage and selection operator (LASSO) regularization and LOOCV.

Figure 21:
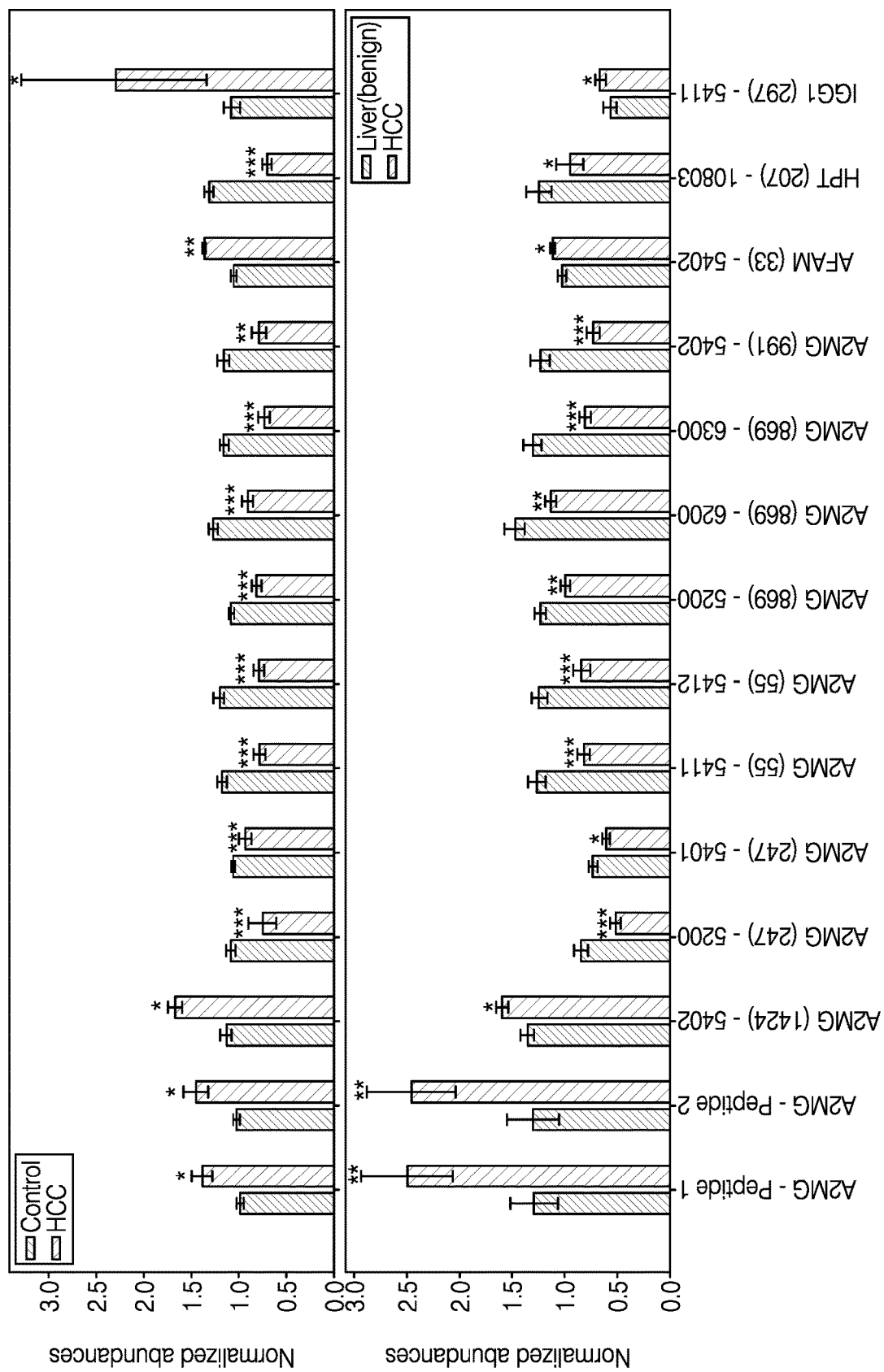
FIG. 21 is a plot of normalized abundances for these 10 peptide structures with respect to a control (e.g., healthy) state versus HCC and benign hepatic mass versus HCC in accordance with one or more embodiments.

FIG. 21 is a plot of normalized abundances for these 10 peptide structures with respect to a control (e.g., healthy) state versus HCC and benign hepatic mass versus HCC in accordance with one or more embodiments.

Figure 22:
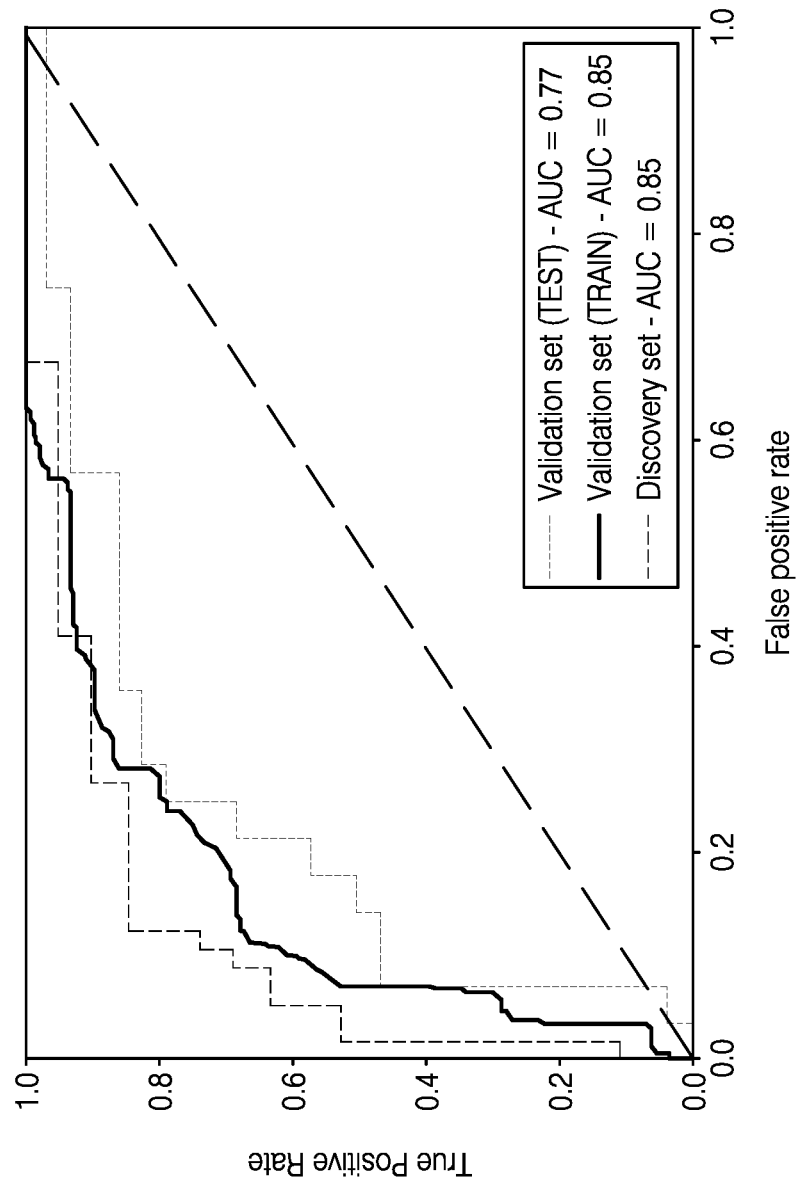
FIG. 22 is a plot of the receiver-operating-characteristic (ROC) curve for distinguishing between HCC and benign hepatic mass for both the training and testing sets in accordance with one or more embodiments.

FIG. 22 is a plot of the receiver-operating-characteristic (ROC) curve for distinguishing between HCC and benign hepatic mass for both the training and testing sets in accordance with one or more embodiments. The area under the ROC curve (AUROC) for the training set was found to be 0.85, while the AUROC for the testing set was found to be 0.77. The AUROC for the discovery set (e.g., the same set used for Model 1) was found to be 0.85.

Table 8 provides the weighted coefficients of the trained Model 2 and the AUC for each of the 10 peptide structures.

TABLE 8

Model 2 Analysis for AM2G-Derived Peptide Structures

| PS-ID NO. | Peptide Structure Name | Model 2 Coefficients (HCC v. Benign Hepatic Mass) | Area Under Curve (AUC) |
|---|---|---|---|
| PS-14 | A2MG (869)-6300 | −0.569 | 0.823 |
| PS-6 | A2MG (247)-5200 | −0.421 | 0.827 |
| PS-15 | A2MG (991)-5402 | −0.261 | 0.806 |
| PS-10 | A2MG (55)-5411 | 0.000 | 0.816 |
| PS-11 | A2MG (55)-5412 | 0.000 | 0.825 |
| PS-13 | A2MG (869)-6200 | 0.000 | 0.733 |
| PS-4 | A2MG-TEHPFTVEEFVLPK ("TEHPFTVEEFVLPK" disclosed as SEQ ID NO: 26) | 0.000 | 0.676 |
| PS-12 | A2MG (869)-5200 | 0.000 | 0.76 |
| PS-16 | A2MG-AIGYLNTGYQR ("AIGYLNTGYQR" disclosed as SEQ ID NO: 25) | 0.088 | 0.668 |
| PS-5 | A2MG (1424)-5402 | 0.167 | 0.673 |

IX.C.2. Validation Using 3 Representative Patients

Three representative patients were tested using a trained regression model trained to distinguish between HCC and one or more other states. Table 9 provides the normalized abundances determined for each patient for various peptide structures. At the bottom of Table 9, the disease indicators computed for these patients based on the normalized abundances are provided. The disease indicator is a probability score that indicates the likelihood that the subject has HCC. The disease indicator was used to classify only patient 3 as having HCC, which was a correct diagnosis.

TABLE 9

Patient Examples

| Peptide Structure Name | Normalized abundance (patient 1) | Normalized abundance (patient 2) | Normalized abundance (patient 3) |
|---|---|---|---|
| TRFE (432)-6502 | 1.28 | 1.12 | 1.20 |
| KLKB1 (494)-5410 | 0.60 | 1.02 | 1.49 |
| KLKB1 (494)-5402 | 0.51 | 1.41 | 3.91 |
| ZA2G (112)-5402 | 0.45 | 1.07 | 1.39 |
| APOC3 (74)-2110 | 2.19 | 1.71 | 2.02 |
| A2MG (55)-5402 | 1.22 | 1.47 | 1.69 |
| A2MG (247)-5402 | 0.82 | 1.38 | 1.42 |
| CO6 (324)-5400 | 1.15 | 1.49 | 0.90 |
| TRFE (432)-6501 | 1.18 | 1.36 | 1.03 |
| CO4A (1328)-5402 | 1.02 | 0.98 | 1.68 |
| TRFE (432)-5402 | 0.93 | 0.91 | 1.65 |
| APOC3 (74)-1102 | 1.33 | 1.08 | 1.82 |
| IGM (209)-5401 | 1.05 | 0.93 | 2.49 |
| CO8A (437)-5410 | 3.05 | 1.28 | 6.00 |
| APOC3 (74)-1202 | 1.42 | 0.41 | 0.65 |
| KLKB1 (494)-6503 | 0.95 | 0.71 | 2.69 |
| APOC3 (74)-1300 | 0.87 | 0.99 | 4.52 |
| KLKB1 (494)-5401 | 1.03 | 1.71 | 4.30 |
| HPT (241)-6502 | 1.34 | 1.03 | 1.58 |
| CLUS (374)-6501 | 1.17 | 1.83 | 1.12 |
| APOM (135)-5421 | 1.30 | 1.19 | 2.03 |
| A1BG (179)-5402 | 1.07 | 1.07 | 1.47 |
| IGG2 (297)-4411 | 1.21 | 0.96 | 1.24 |
| CO6 (324)-5200 | 2.27 | 0.81 | 1.02 |
| HPT (207)-11904 | 1.20 | 0.92 | 0.57 |
| HPT (241)-5401 | 0.92 | 0.75 | 0.47 |
| AGP1 (93)-6502 | 1.34 | 0.87 | 1.16 |
| HPT (241)-5511 | 1.37 | 1.06 | 0.80 |

TABLE 9-continued

Patient Examples

| Peptide Structure Name | Normalized abundance (patient 1) | Normalized abundance (patient 2) | Normalized abundance (patient 3) |
|---|---|---|---|
| CFAI (70)-5401 | 0.86 | 1.03 | 0.53 |
| HPT (241)-5402 | 1.49 | 0.98 | 0.83 |
| A2MG (869)-6200 | 0.81 | 0.98 | 0.97 |
| VTNC (169)-5401 | 1.44 | 0.89 | 0.97 |
| AACT (106)-7604 | 2.35 | 2.77 | 0.78 |
| IGG2 (297)-4400 | 1.16 | 0.79 | 0.78 |
| CO8A (437)-5200 | 1.54 | 0.72 | 0.50 |
| A1AT (271)-5402 | 1.01 | 0.98 | 0.79 |
| AGP1 (33)-5402 | 1.11 | 0.87 | 0.59 |
| IGA2 (205)-5510 | 3.00 | 0.41 | 0.09 |
| A1AT (271)-5401 | 0.90 | 0.95 | 0.76 |
| HPT (207)-121005 | 1.17 | 0.69 | 0.30 |
| Probability of HCC vs rest | 0.01 | 0.23 | 0.90 |

X. Recitation of Embodiments

Embodiment 1. A method of classifying a biological sample with respect to a plurality of states associated with fatty liver disease (FLD) progression, the method comprising receiving peptide structure data corresponding to a set of glycoproteins in the biological sample obtained from a subject; inputting quantification data identified from the peptide structure data for a set of peptide structures into a machine learning model, wherein the set of peptide structures includes at least one peptide structure identified from a plurality of peptide structures in Table 1; analyzing the quantification data using the machine learning model to generate a disease indicator; and generating a diagnosis output based on the disease indicator that classifies the biological sample as evidencing a corresponding state of the plurality of states associated with the FLD progression.

Embodiment 2. The method of embodiment 1, wherein the disease indicator comprises a score and wherein generating the diagnosis output comprises: determining that the score falls within a selected range associated with the corresponding state of the plurality of states; and determining that the biological sample evidences the corresponding state in response to a determination that the score falls within the selected range associated with corresponding state.

Embodiment 3. The method of embodiment 1 or embodiment 2, wherein the plurality of states includes a non-alcoholic steatohepatitis (NASH) state and a hepatocellular carcinoma (HCC) state.

Embodiment 4. The method of any one of embodiments 1-3, wherein the plurality of states includes a non-NASH/HCC state that comprises at least one of a healthy state, a liver disease-free state, or a benign hepatic mass state.

Embodiment 5. The method of any one of embodiments 1-4, wherein the at least one peptide structure comprises a glycopeptide structure defined by a peptide sequence and a glycan structure linked to the peptide sequence at a linking site of the peptide sequence, as identified in Table 1, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, 51, or 52 as defined in Table 1.

Embodiment 6. The method of any one of embodiments 1-5, further comprising training the machine learning model using training data, wherein the training data comprises a plurality of peptide structure profiles for a plurality of subjects and identifies a diagnosed state of the plurality of states for each peptide structure profile of the plurality of peptide structure profiles.

Embodiment 7. The method of embodiment 6, further comprising: (1) performing a differential expression analysis using initial training data to compare at least one of: a first portion of the plurality of subjects diagnosed with NASH versus a second portion of the plurality of subjects diagnosed with HCC; the first portion of the plurality of subjects diagnosed with NASH versus a third portion of the plurality of subjects assigned to a control state; or the second portion of the plurality of subjects diagnosed with HCC versus the third portion of the plurality of subjects assigned to the control state; and (2) identifying a group of peptide structures based on the differential expression analysis for use as prognostic markers for the FLD progression, wherein the group of peptide structures is identified in Table 1; and (3) forming the training data based on the group of peptide structures identified.

Embodiment 8. The method of embodiment 7, wherein the control state comprises at least one of a healthy state, a liver disease-free state, or a benign hepatic mass state.

Embodiment 9. The method of any one of embodiments 1-8, wherein the machine learning model comprises a logistic regression model.

Embodiment 10. The method of any one of embodiments 1-9, wherein the quantification data for a peptide structure of the set of peptide structures comprises at least one of an abundance, a relative abundance, a normalized abundance, a relative quantity, an adjusted quantity, a normalized quantity, a relative concentration, an adjusted concentration, or a normalized concentration.

Embodiment 11. The method of any one of embodiments 1-9, wherein the quantification data for the set of peptide structures comprises a normalized abundance for each peptide structure of the set of peptide structures.

Embodiment 12. The method of any one of embodiments 1-11, wherein the peptide structure data is generated using multiple reaction monitoring mass spectrometry (MRM-MS).

Embodiment 13. The method of any one of embodiments 1-11, wherein the peptide structure data is generated using a liquid chromatography/mass spectrometry (LC/MS) system.

Embodiment 14. The method of any one of embodiments 1-13, further comprising: creating a sample from the biological sample; and preparing the sample using reduction, alkylation, and enzymatic digestion to form a prepared sample that includes the set of peptide structures.

Embodiment 15. The method of embodiment 14, further comprising: generating the peptide structure data from the prepared sample using multiple reaction monitoring mass spectrometry (MRM-MS).

Embodiment 16. The method of any one of embodiments 1-15, wherein the biological sample comprises at least one of blood, serum, or plasma.

Embodiment 17. The method of any one of embodiments 1-16, wherein generating the diagnosis output comprises: generating a report that identifies the corresponding state.

Embodiment 18. The method of any one of embodiments 1-17, further comprising: generating a treatment output based on at least one of the diagnosis output or the disease indicator.

Embodiment 19. The method of embodiment 18, wherein the treatment output comprises at least one of an identification of a treatment to treat the subject, a design for the treatment, a manufacturing plan for the treatment, or a treatment plan for administering the treatment.

Embodiment 20. The method of embodiment 19, wherein the corresponding state is a NASH state and wherein the treatment comprises at least one of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, or GR-MD-02.

Embodiment 21. The method of embodiment 19, wherein the corresponding state is an HCC state and wherein the treatment comprises at least one of Atezolizumab, Bevacizumab, Sorafenib, Lenvatinib, Nivolumab, Regorafenib, Cabozantinib, Pemigatinib, Ramucirumab, or Pembrolizumab.

Embodiment 22. The method of any one of embodiments 1-18, wherein the corresponding state is non-alcoholic steatohepatitis (NASH) and further comprising generating a treatment plan for the subject, wherein the treatment plan identifies at least one of a set of lifestyle modifications, a set of dietary modifications, coffee, vitamin E, calorie reduction, reduced salt intake, reduced sugar intake, or a set of cholesterol-reducing medications.

Embodiment 23. The method of any one of embodiments 1-18, wherein the corresponding state is a NASH state and wherein the diagnosis output identifies that the biological sample is positive for the corresponding state and further comprising: administering a therapeutic dosage of a therapeutic to the subject, the therapeutic being selected from the group consisting of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02.

Embodiment 24. The method of any one of embodiments 1-18, wherein the corresponding state is an HCC state and wherein the diagnosis output identifies that the biological sample is positive for the corresponding state and further comprising: administering a therapeutic dosage of a therapeutic to the subject, the therapeutic being selected from the group consisting of Atezolizumab, Bevacizumab, Sorafenib, Lenvatinib, Nivolumab, Regorafenib, Cabozantinib, Pemigatinib, Ramucirumab, or Pembrolizumab.

Embodiment 25. A method of training a model to diagnose a subject with one of a plurality of states associated with fatty liver disease (FLD) progression, the method comprising: receiving quantification data for a panel of peptide structures for a plurality of subjects diagnosed with the plurality of states associated with the FLD progression, wherein the quantification data comprises a plurality of peptide structure profiles for the plurality of subjects and identifies a corresponding state of the plurality of states for each peptide structure profile of the plurality of peptide structure profiles; and training a machine learning model using the quantification data to determine which state of the plurality of states a biological sample from the subject corresponds.

Embodiment 26. The method of embodiment 25, wherein the machine learning model comprises a logistic regression model.

Embodiment 27. The method of embodiment 26, wherein the logistic regression model comprises a LASSO regression model.

Embodiment 28. The method of any one of embodiments 25-27, wherein training the machine learning model comprises: training the machine learning model using a portion of the quantification data corresponding to a set of peptide structures that is a subset of the panel of peptide structures to determine which state of the plurality of states the biological sample from the subject corresponds.

Embodiment 29. The method of embodiment 28, further comprising: performing a differential expression analysis using the quantification data for the plurality of subjects.

Embodiment 30. The method of embodiment 29, further comprising: identifying the set of peptide structures as the subset of the plurality of peptide structures relevant to the determining which state of the plurality of states the biological sample from the subject corresponds based on at least one of fold-changes, false discovery rates, or p-values computed as part of the differential expression analysis.

Embodiment 31. The method of any one of embodiments 25-30, wherein the plurality of states further includes at least one of a non-alcoholic steatohepatitis (NASH) state, a hepatocellular carcinoma (HCC) state, or a healthy state.

Embodiment 32. The method of any one of embodiments 25-31, wherein the quantification data for the panel of peptide structures for the plurality of subjects diagnosed with the plurality of states comprises at least one of an abundance, a relative abundance, a normalized abundance, a relative quantity, an adjusted quantity, a normalized quantity, a relative concentration, an adjusted concentration, or a normalized concentration.

Embodiment 33. The method of any one of embodiments 25-31, wherein the quantification data for the panel of peptide structures for the plurality of subjects diagnosed with the plurality of states comprises normalized abundances.

Embodiment 34. The method of any one of embodiments 25-33, wherein the biological sample comprises at least one of blood, serum, or plasma.

Embodiment 35. The method of any one of embodiments 25-34, wherein the quantification data is generated using a liquid chromatography/mass spectrometry (LC/MS) system.

Embodiment 36. The method of any one of embodiments 25-35, wherein the quantification data is generated using multiple reaction monitoring mass spectrometry (MRM-MS).

Embodiment 37. A method of detecting a presence of one of a plurality of states associated with fatty liver disease (FLD) progression in a biological sample, the method comprising: receiving peptide structure data corresponding to a set of glycoproteins in the biological sample obtained from a subject; analyzing the peptide structure data using a supervised machine learning model to generate a disease indicator based on at least 3 peptide structures selected from a group of peptide structures identified in Table 1; and detecting the presence of a corresponding state of the plurality of states associated with the FLD progression in response to a determination that the disease indicator falls within a selected range associated with the corresponding state.

Embodiment 38. The method of embodiment 37, wherein a peptide structure of the at least 3 peptide structures comprises a glycopeptide structure defined by a peptide sequence and a glycan structure linked to the peptide sequence at a linking site of the peptide sequence, as identified in Table 1, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, 52, or 52 as defined in Table 1.

Embodiment 39. The method of embodiment 37 or embodiment 38, wherein the supervised machine learning model comprises a logistic regression model.

Embodiment 40. The method of any one of embodiments 37-39, wherein the supervised machine learning model comprises a penalized multivariable logistic regression model.

Embodiment 41. The method of any one of embodiments 37-40, wherein the peptide structure data comprises quantification data.

Embodiment 42. The method of embodiment 41, wherein the quantification data for a peptide structure of the group of peptide structures comprises at least one of an abundance, a relative abundance, a normalized abundance, a relative quantity, an adjusted quantity, a normalized quantity, a relative concentration, an adjusted concentration, or a normalized concentration.

Embodiment 43. The method of embodiment 41, wherein the quantification data comprises normalized abundances.

Embodiment 44. The method of any one of embodiments 37-43, wherein the disease indicator is a probability score.

Embodiment 45. The method of any one of embodiments 37-44, further comprising: generating a report that includes a diagnosis based on the corresponding state detected for the subject.

Embodiment 46. The method of any one of embodiments 37-45, wherein the plurality of states includes at least two selected from a group consisting of a non-alcoholic steatohepatitis (NASH) state, a hepatocellular carcinoma (HCC) state, and a non-NASH/HCC state.

Embodiment 47. The method of any one of embodiments 37-46, wherein analyzing the peptide structure data comprises: computing the disease indicator using a weight coefficient associated with each peptide structure of the at least 3 peptide structures, the weight coefficient of a corresponding peptide structure of the at least 3 peptide structures indicating a relative significance of the corresponding peptide structure to the disease indicator.

Embodiment 48. The method of any one of embodiments 37-46, wherein analyzing the peptide structure data comprises: computing a peptide structure profile for the biological sample that identifies a weighted value for each peptide structure of the at least 3 peptide structures, wherein the weighted value for a peptide structure of the at least 3 peptide structures is a product of a quantification metric for the peptide structure identified from the peptide structure data and a weight coefficient for the peptide structure; and computing the disease indicator using the peptide structure profile.

Embodiment 49. The method of any one of embodiments 37-48, wherein the corresponding state is a non-NASH/HCC state and wherein the selected range associated with the non-NASH/HCC state is between 0.00 and 0.05.

Embodiment 50. The method of any one of embodiments 37-48, wherein the corresponding state is non-alcoholic steatohepatitis (NASH) state and the selected range associated with the NASH state is between 0.05 and 0.4.

Embodiment 51. The method of any one of embodiments 37-48, wherein the corresponding state is a hepatocellular carcinoma (HCC) state and the selected range associated with the HCC state is between 0.4 and 1.0.

Embodiment 52. The method of any one of embodiments 37-51, further comprising: creating a sample from the biological sample; and preparing the sample using reduction, alkylation, and enzymatic digestion to form a prepared sample that includes a set of peptide structures.

Embodiment 53. The method of embodiment 52, further comprising: generating the peptide structure data from the prepared sample using multiple reaction monitoring mass spectrometry (MRM-MS).

Embodiment 54. The method of any one of embodiments 37-52, wherein the peptide structure data is generated using a liquid chromatography/mass spectrometry (LC/MS) system.

Embodiment 55. The method of any one of embodiments 37-52, wherein the peptide structure data is generated using multiple reaction monitoring mass spectrometry (MRM-MS).

Embodiment 56. The method of any one of embodiments 37-55, wherein the biological sample comprises at least one of blood, serum, or plasma.

Embodiment 57. The method of any one of embodiments 37-56, further comprising: generating a treatment output based on the disease indicator.

Embodiment 58. The method of embodiment 57, wherein the treatment output comprises at least one of an identification of a treatment to treat the subject, a design for the treatment, a manufacturing plan for the treatment, or a treatment plan for administering the treatment.

Embodiment 59. The method of embodiment 58, wherein the corresponding state is a NASH state and wherein the treatment comprises at least one of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02.

Embodiment 60. The method of embodiment 58, wherein the corresponding state is an HCC state and wherein the treatment comprises at least one of Atezolizumab, Bevacizumab, Sorafenib, Lenvatinib, Nivolumab, Regorafenib, Cabozantinib, Pemigatinib, Ramucirumab, or Pembrolizumab.

Embodiment 61. The method of any one of embodiments 37-57, wherein the corresponding state is a NASH state and further comprising: administering a therapeutic dosage of a therapeutic to the subject, the therapeutic being selected from the group consisting of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02.

Embodiment 62. The method of any one of embodiments 37-57, wherein the corresponding state is an HCC state and further comprising: administering a therapeutic dosage of a therapeutic to the subject, the therapeutic being selected from the group consisting of Atezolizumab, Bevacizumab, Sorafenib, Lenvatinib, Nivolumab, Regorafenib, Cabozantinib, Pemigatinib, Ramucirumab, or Pembrolizumab.

Embodiment 63. A method of classifying a biological sample as corresponding to one of a plurality of states associated with fatty liver disease (FLD) progression, the method comprising: training a supervised machine learning model using training data, wherein the training data comprises a plurality of peptide structure profiles for a plurality of training subjects and identifies a state of the plurality of states for each peptide structure profile of the plurality of peptide structure profiles; receiving peptide structure data corresponding to a set of glycoproteins in the biological sample obtained from a subject; inputting quantification data identified from the peptide structure data for a set of peptide structures into the supervised machine learning model that has been trained, wherein the set of peptide structures includes at least one peptide structure identified in Table 1; analyzing the quantification data using the supervised machine learning model to generate a score; determining that the score falls within a selected range associated with a corresponding state of the plurality of states associated with the FLD progression; and generating a diagnosis output that indicates that the biological sample evidences the corresponding state, wherein the plurality of states includes a non-alcoholic steatohepatitis (NASH) state, a hepatocellular carcinoma (HCC) state, and a non-NASH/HCC state.

Embodiment 64. A method of treating a non-alcoholic steatohepatitis (NASH) disorder in a patient to at least one of reduce, stall, or reverse a progression of the NASH disorder into hepatocellular carcinoma, the method comprising: receiving a biological sample from the patient; determining a quantity of each peptide structure identified in Table 1 in the biological sample using a multiple reaction monitoring mass spectrometry (MRM-MS) system; analyzing the quantity of each peptide structure using a machine learning model to generate a disease indicator; generating a diagnosis output based on the disease indicator that classifies the biological sample as evidencing that the patient has the NASH disorder; and administering Obeticholic acid (OCA) or a derivative thereof to the patient, the administering comprising at least one of intravenous or oral administration in a range of 10-25 mg daily.

Embodiment 65. The method of embodiment 64, further comprising: preparing the biological sample to form a prepared sample comprising a set of peptide structures; and inputting the prepared sample into the MRM-MS system using a liquid chromatography system.

Embodiment 66. A method of treating a hepatocellular carcinoma (HCC) disorder in a patient, the method comprising: receiving a biological sample from the patient; determining a quantity of each peptide structure identified in Table 1 in the biological sample using a multiple reaction monitoring mass spectrometry (MRM-MS) system; analyzing the quantity of each peptide structure using a machine learning model to generate a disease indicator; generating a diagnosis output based on the disease indicator that classifies the biological sample as evidencing that the patient has the HCC disorder; and administering at least one of:
  Sorafenib or a derivative thereof to the patient, the administering comprising at least one of intravenous or oral administration in a range of 775-825 mg daily;
  Lenvatinib or a derivative thereof to the patient, the administering comprising at least one of intravenous or oral administration in a range of 7.5-8.5 mg/day when the patient weighs <60 kg and 11.5-12.5 mg/day when the patient weighs >60 kg;
  Nivolumab or a derivative thereof to the patient, the administering comprising at least one of intravenous or oral administration in a range of 0.75-1.25 mg/kg;
  Regorafenib or a derivative thereof to the patient, the administering comprising oral administration in a range of 150-170 mg/day;
  Cabozantinib or a derivative thereof to the patient, the administering comprising at least one of intravenous or oral administration in a range of 50-70 mg/day; or
  Ramucirumab or a derivative thereof to the patient, the administering comprising at least one of intravenous or oral administration in a range of 8-12 mg/kg.

Embodiment 67. The method of embodiment 66, further comprising: preparing the biological sample to form a prepared sample comprising a set of peptide structures; and inputting the prepared sample into the MRM-MS system for analysis using a liquid chromatography system.

Embodiment 68. A method of designing a treatment for a subject diagnosed with a disease state associated with a fatty liver disease (FLD) progression, the method comprising designing a therapeutic for treating the subject in response to determining that a biological sample obtained from the subject evidences the disease state using part or all of the method of any one of embodiments 1-63.

Embodiment 69. A method of planning a treatment for a subject diagnosed with a disease state associated with a fatty liver disease (FLD) progression, the method comprising generating a treatment plan for treating the subject in response to determining that a biological sample obtained from the subject evidences the disease state using part or all of the method of any one of embodiments 1-63.

Embodiment 70. A method of treating a subject diagnosed with a disease state associated with a fatty liver disease (FLD) progression, the method comprising: administering to the subject a therapeutic to treat the subject based on determining that a biological sample obtained from the subject evidences the disease state using part or all of the method of any one of embodiments 1-63.

Embodiment 71. A method of treating a subject diagnosed with a disease state associated with a fatty liver disease (FLD) progression, the method comprising: selecting a therapeutic to treat the subject based on determining that the subject is responsive to the therapeutic using the method of any of embodiments 1-63.

Embodiment 72. A method for analyzing a set of peptide structures in a sample from a patient, the method comprising:
  (a) obtaining the sample from the patient;
  (b) preparing the sample to form a prepared sample comprising the set of peptide structures;
  (c) inputting the prepared sample into a mass spectrometry system using a liquid chromatography system;
  (d) detecting a set of product ions associated with each peptide structure of the set of peptide structures using the mass spectrometry system,
    wherein the set of peptide structures includes at least one peptide structure selected from peptide structures PS-1 to PS-53 identified in Table 4;
    wherein the set of peptide structures includes a peptide structure that is characterized as having:
      (i) a precursor ion with a mass-charge (m/z) ratio within ±1.5 of the m/z ratio listed for the precursor ion in Table 4 as corresponding to the peptide structure; and
      (ii) a product ion having an m/z ratio within ±1.0 of the m/z ratio listed for a first product ion in Table 4 as corresponding to the peptide structure; and
  (e) generating quantification data for the set of product ions using the mass spectrometry system.

Embodiment 73. The method of embodiment 72, wherein the mass-charge (m/z) ratio of the precursor ion is within ±1.0 of the m/z ratio listed for the precursor ion in Table 4 as corresponding to the peptide structure.

Embodiment 74. The method of embodiment 72, wherein the mass-charge (m/z) ratio of the precursor ion is within ±0.5 of the m/z ratio listed for the precursor ion in Table 4 as corresponding to the peptide structure.

Embodiment 75. The method of embodiment 72, wherein the mass-charge (m/z) ratio of the product ion is within ±0.8 of the m/z ratio listed for the precursor ion in Table 4 as corresponding to the peptide structure.

Embodiment 76. The method of embodiment 72, wherein the mass-charge (m/z) ratio of the product ion is within ±0.5 of the m/z ratio listed for the precursor ion in Table 4 as corresponding to the peptide structure.

Embodiment 77. The method of any one of embodiments 72-76, further comprising: generating a diagnosis output using the quantification data and a machine learning model that has been trained to detect a presence of a disease state associated with a fatty liver disease (FLD) progression.

Embodiment 78. The method of any one of embodiments 72-77, wherein the mass spectrometry system comprises a reaction monitoring mass spectrometry system that uses at least one of multiple reaction monitoring mass spectrometry (MRM-MS), or selected reaction monitoring mass spectrometry (SRM-MS) to detect the set of product ions and generate the quantification data.

Embodiment 79. The method of any one of embodiments 72-78, wherein the liquid chromatography system is a high-performance liquid chromatography system.

Embodiment 80. The method of any one of embodiments 72-79, wherein the sample comprises a plasma sample.

Embodiment 81. The method of any one of embodiments 72-80, wherein the sample comprises a serum sample.

Embodiment 82. The method of any one of embodiments 72-81, wherein the sample comprises a blood sample.

Embodiment 83. The method of any one of embodiments 72-82, wherein preparing the sample comprises at least one of: denaturing one or more proteins in the sample to form one or more denatured proteins; reducing the one or more denatured proteins in the sample to form one or more reduced proteins; alkylating the one or more proteins in the sample using an alkylating agent to prevent reformation of disulfide bonds in the one or more reduced proteins to form one or more alkylated proteins; or digesting the one or more alkylated proteins in the sample using a proteolysis catalyst to form the prepared sample comprising the set of peptide structures.

Embodiment 84. A composition comprising at least one of peptide structures PS-1 to PS-53 identified in Table 1.

Embodiment 85. A composition comprising a peptide structure or a product ion, wherein: the peptide structure or product ion comprises an amino acid sequence having at least 90% sequence identity to any one of SEQ ID NOS: 23-52, corresponding to peptide structures PS-1 to PS-53 in Table 1; and the product ion is selected as one from a group consisting of product ions identified in Table 4 including product ions falling within an identified m/z range.

Embodiment 86. A composition comprising a glycopeptide structure selected as one from a group consisting of peptide structures PS-1 to PS-53 identified in Table 4, wherein the glycopeptide structure comprises: an amino acid peptide sequence identified in Table 5 as corresponding to the glycopeptide structure; and a glycan structure identified in Table 1 as corresponding to the glycopeptide structure in which the glycan structure is linked to a residue of the amino acid peptide sequence at a corresponding position identified in Table 1, wherein the glycan structure has a glycan composition.

Embodiment 87. The composition of embodiment 86, wherein the glycan composition is identified in Table 7.

Embodiment 88. The composition of embodiment 86 or embodiment 87, wherein the glycopeptide structure has a precursor ion having a charge identified in Table 4 as corresponding to the glycopeptide structure.

Embodiment 89. The composition of any one of embodiments 86-88, wherein the glycopeptide structure has a precursor ion with an m/z ratio within ±1.5 of the m/z ratio listed for the precursor ion in Table 4 as corresponding to the glycopeptide structure.

Embodiment 90. The composition of any one of embodiments 86-88, wherein the glycopeptide structure has a precursor ion with an m/z ratio within ±1.0 of the m/z ratio listed for the precursor ion in Table 4 as corresponding to the glycopeptide structure.

Embodiment 91. The composition of any one of embodiments 86-88, wherein the glycopeptide structure has a precursor ion with an m/z ratio within ±0.5 of the m/z ratio listed for the precursor ion in Table 4 as corresponding to the glycopeptide structure.

Embodiment 92. The composition of any one of embodiments 86-91, wherein the glycopeptide structure has a product ion with an m/z ratio within ±1.0 of the m/z ratio listed for the first product ion in Table 4 as corresponding to the glycopeptide structure.

Embodiment 93. The composition of any one of embodiments 86-91, wherein the glycopeptide structure has a product ion with an m/z ratio within ±0.8 of the m/z ratio listed for the first product ion in Table 4 as corresponding to the glycopeptide structure.

Embodiment 94. The composition of any one of embodiments 86-91, wherein the glycopeptide structure has a product ion with an m/z ratio within ±0.5 of the m/z ratio listed for the first product ion in Table 4 as corresponding to the glycopeptide structure.

Embodiment 95. The composition of any one of embodiments 86-94, wherein the glycopeptide structure has a monoisotopic mass identified in Table 1 as corresponding to the glycopeptide structure.

Embodiment 96. A composition comprising a peptide structure selected as one from a plurality of peptide structures identified in Table 1, wherein: the peptide structure has a monoisotopic mass identified as corresponding to the peptide structure in Table 1; and the peptide structure comprises the amino acid sequence of SEQ ID NOs: 23-52 identified in Table 1 as corresponding to the peptide structure.

Embodiment 97. The composition of embodiment 96, wherein the peptide structure has a precursor ion having a charge identified in Table 4 as corresponding to the peptide structure.

Embodiment 98. The composition of embodiment 96 or embodiment 97, wherein the peptide structure has a precursor ion with an m/z ratio within ±1.5 of the m/z ratio listed for the precursor ion in Table 4 as corresponding to the peptide structure.

Embodiment 99. The composition of embodiment 96 or embodiment 97, wherein the peptide structure has a precursor ion with an m/z ratio within ±1.0 of the m/z ratio listed for the precursor ion in Table 4 as corresponding to the peptide structure.

Embodiment 100. The composition of embodiment 96 or embodiment 97, wherein the peptide structure has a precursor ion with an m/z ratio within ±0.5 of the m/z ratio listed for the precursor ion in Table 4 as corresponding to the peptide structure.

Embodiment 101. The composition of any one of embodiments 96-100, wherein the peptide structure has a product ion with an m/z ratio within ±1.0 of the m/z ratio listed for the first product ion in Table 4 as corresponding to the peptide structure.

Embodiment 102. The composition of any one of embodiments 96-100, wherein the peptide structure has a product ion with an m/z ratio within ±0.8 of the m/z ratio listed for the first product ion in Table 4 as corresponding to the peptide structure.

Embodiment 103. The composition of any one of embodiments 96-100, wherein the peptide structure has a product ion with an m/z ratio within ±0.5 of the m/z ratio listed for the first product ion in Table 4 as corresponding to the peptide structure.

Embodiment 104. A kit comprising at least one agent for quantifying at least one peptide structure identified in Table 1 to carry out part or all of the method of any one of embodiments 1-83.

Embodiment 105. A kit comprising at least one of a glycopeptide standard, a buffer, or a set of peptide sequences to carry out part or all of the method of any one of embodiments 1-83, a peptide sequence of the set of peptide sequences identified by a corresponding one of SEQ ID NOS: 23-52, defined in Table 1.

Embodiment 106. A system comprising: one or more data processors; and a non-transitory computer readable storage medium containing instructions which, when executed on the one or more data processors, cause the one or more data processors to perform part or all of any one of embodiments 1-83.

Embodiment 107. A computer-program product tangibly embodied in a non-transitory machine-readable storage medium, including instructions configured to cause one or more data processors to perform part or all of any one of embodiments 1-83.

Further, an embodiment may include part or all of any one or more of embodiments 1-107 described above. For example, an embodiment may include one or more features from any one or more of embodiments 1-107 used in any combination.

XI. Additional Considerations

Any headers and/or subheaders between sections and subsections of this document are included solely for the purpose of improving readability and do not imply that features cannot be combined across sections and subsection. Accordingly, sections and subsections do not describe separate embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art. The present description provides preferred exemplary embodiments, and is not intended to limit the scope, applicability, or configuration of the disclosure. Rather, the present description of the preferred exemplary embodiments will provide those skilled in the art with an enabling description for implementing various embodiments.

It is understood that various changes may be made in the function and arrangement of elements without departing from the spirit and scope as set forth in the appended claims. Thus, such modifications and variations are considered to be within the scope set forth in the appended claims. Further, the terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

Specific details are given in the present description to provide an understanding of the embodiments. However, it is understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method of classifying a biological sample with respect to a plurality of states associated with fatty liver disease (FLD) progression, the method comprising:
   receiving peptide structure data corresponding to a set of glycoproteins in the biological sample obtained from a subject;
   inputting quantification data identified from the peptide structure data for a set of peptide structures into a machine learning model, wherein the set of peptide structures includes at least one peptide structure identified from a plurality of peptide structures in Table 5;
   analyzing the quantification data using the machine learning model to generate a disease indicator; and
   generating a diagnosis output based on the disease indicator that classifies the biological sample as evidencing a corresponding state of the plurality of states associated with the FLD progression.

2. The method of claim 1, wherein the disease indicator comprises a score and wherein generating the diagnosis output comprises:
   determining that the score falls within a selected range associated with the corresponding state of the plurality of states; and
   determining that the biological sample evidences the corresponding state in response to a determination that the score falls within the selected range associated with the corresponding state.

3. The method of claim 1, wherein the plurality of states includes a non-alcoholic steatohepatitis (NASH) state and a hepatocellular carcinoma (HCC) state.

4. The method of claim 1, wherein the plurality of states includes a non-NASH/HCC state that comprises at least one of a healthy state, a liver disease-free state, or a benign hepatic mass state.

5. The method of claim 1, wherein the at least one peptide structure comprises a glycopeptide structure defined by a peptide sequence and a glycan structure linked to the peptide sequence at a linking site of the peptide sequence with the peptide sequence being one of SEQ ID NOS: 23, 24, 29, 30, 31, 33, 35, 36, 37, 38, 39, 40, 41, 42, 43, 44, 45, 46, 47, 48, 49, 50, 51, or 52 as defined in Table 5, wherein the glycan structure corresponds to a glycan GL NO of Table 1 and the linking site of the peptide sequence for the glycan structure is listed in Table 1.

6. The method of claim 1, wherein the quantification data for a peptide structure of the set of peptide structures comprises at least one of an abundance, a relative abundance, a normalized abundance, a relative quantity, an adjusted quantity, a normalized quantity, a relative concentration, an adjusted concentration, or a normalized concentration.

7. The method of claim 1, wherein the peptide structure data is generated using multiple reaction monitoring mass spectrometry (MRM-MS).

8. A method of detecting a presence of one of a plurality of states associated with fatty liver disease (FLD) progression in a biological sample, the method comprising:
receiving peptide structure data corresponding to a set of glycoproteins in the biological sample obtained from a subject;
analyzing the peptide structure data using a supervised machine learning model to generate a disease indicator based on at least 3 peptide structures selected from a group of peptide structures identified in Table 5; and
detecting the presence of a corresponding state of the plurality of states associated with the FLD progression in response to a determination that the disease indicator falls within a selected range associated with the corresponding state.

9. The method of claim 8, wherein a peptide structure of the at least 3 peptide structures comprises a glycopeptide structure defined by a peptide sequence and a glycan structure linked to the peptide sequence at a linking site of the peptide sequence with the peptide sequence being one of SEQ ID NOS: 23, 24, 29, 30, 31, 33, 35, 36, 37, 38, 39, 40, 41, 42, 43, 44, 45, 46, 47, 48, 49, 50, 52, or 52 as defined in Table 5, wherein the glycan structure corresponds to a glycan GL NO of Table 1 and the linking site of the peptide sequence for the glycan structure is listed in Table 1.

10. The method of claim 8, wherein the supervised machine learning model comprises a logistic regression model.

11. The method of claim 8, wherein the supervised machine learning model comprises a penalized multivariable logistic regression model.

12. The method of claim 8, wherein the peptide structure data comprises quantification data, the quantification data for a peptide structure of the group of peptide structures comprising at least one of an abundance, a relative abundance, a normalized abundance, a relative quantity, an adjusted quantity, a normalized quantity, a relative concentration, an adjusted concentration, or a normalized concentration.

13. The method of claim 8, wherein the disease indicator is a probability score.

14. The method of claim 8, further comprising:
generating a report that includes a diagnosis based on the corresponding state detected for the subject.

15. The method of claim 8, wherein the plurality of states includes at least two selected from a group consisting of a non-alcoholic steatohepatitis (NASH) state, a hepatocellular carcinoma (HCC) state, and a non-NASH/HCC state.

16. The method of claim 1, wherein the at least one peptide structure comprises a glycopeptide structure defined by a peptide sequence and a glycan structure linked to the peptide sequence at a linking site of the peptide sequence as defined in Table 5, wherein the glycan structure corresponds to a glycan GL NO of Table 1 and the linking site of the peptide sequence for the glycan structure is listed in Table 1.

17. The method of claim 8, wherein the peptide structure of the at least 3 peptide structure comprises a glycopeptide structure defined by a peptide sequence and a glycan structure linked to the peptide sequence at a linking site of the peptide sequence as defined in Table 5, wherein the glycan structure corresponds to a glycan GL NO of Table 1 and the linking site of the peptide sequence for the glycan structure is listed in Table 1.

18. The method of claim 5, wherein the glycan structure comprises a glycan composition of Table 7.

19. The method of claim 9, wherein the glycan structure comprises a glycan composition of Table 7.

20. The method of claim 16, wherein the glycan structure comprises a glycan composition of Table 7.

21. The method of claim 17, wherein the glycan structure comprises a glycan composition of Table 7.

* * * * *

SEQUENCE LISTING

```
<160> NUMBER OF SEQ ID NOS: 54

<210> SEQ ID NO 1
<211> LENGTH: 418
<212> TYPE: PRT
<213> ORGANISM: Homo sapiens

<400> SEQUENCE: 1

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45
```

```
Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 2
<211> LENGTH: 495
<212> TYPE: PRT
<213> ORGANISM: Homo sapiens

<400> SEQUENCE: 2
```

```
Met Ser Met Leu Val Phe Leu Leu Leu Trp Gly Val Thr Trp Gly
1               5                   10                  15

Pro Val Thr Glu Ala Ala Ile Phe Tyr Glu Thr Gln Pro Ser Leu Trp
            20                  25                  30

Ala Glu Ser Glu Ser Leu Leu Lys Pro Leu Ala Asn Val Thr Leu Thr
                35                  40                  45

Cys Gln Ala His Leu Glu Thr Pro Asp Phe Gln Leu Phe Lys Asn Gly
    50                  55                  60

Val Ala Gln Glu Pro Val His Leu Asp Ser Pro Ala Ile Lys His Gln
65                  70                  75                  80

Phe Leu Leu Thr Gly Asp Thr Gln Gly Arg Tyr Arg Cys Arg Ser Gly
                85                  90                  95

Leu Ser Thr Gly Trp Thr Gln Leu Ser Lys Leu Leu Glu Leu Thr Gly
                100                 105                 110

Pro Lys Ser Leu Pro Ala Pro Trp Leu Ser Met Ala Pro Val Ser Trp
            115                 120                 125

Ile Thr Pro Gly Leu Lys Thr Thr Ala Val Cys Arg Gly Val Leu Arg
    130                 135                 140

Gly Val Thr Phe Leu Leu Arg Arg Glu Gly Asp His Glu Phe Leu Glu
145                 150                 155                 160

Val Pro Glu Ala Gln Glu Asp Val Glu Ala Thr Phe Pro Val His Gln
                165                 170                 175

Pro Gly Asn Tyr Ser Cys Ser Tyr Arg Thr Asp Gly Glu Gly Ala Leu
            180                 185                 190

Ser Glu Pro Ser Ala Thr Val Thr Ile Glu Glu Leu Ala Ala Pro Pro
    195                 200                 205

Pro Pro Val Leu Met His His Gly Glu Ser Ser Gln Val Leu His Pro
210                 215                 220

Gly Asn Lys Val Thr Leu Thr Cys Val Ala Pro Leu Ser Gly Val Asp
225                 230                 235                 240

Phe Gln Leu Arg Arg Gly Glu Lys Glu Leu Leu Val Pro Arg Ser Ser
                245                 250                 255

Thr Ser Pro Asp Arg Ile Phe Phe His Leu Asn Ala Val Ala Leu Gly
            260                 265                 270

Asp Gly Gly His Tyr Thr Cys Arg Tyr Arg Leu His Asp Asn Gln Asn
    275                 280                 285

Gly Trp Ser Gly Asp Ser Ala Pro Val Glu Leu Ile Leu Ser Asp Glu
    290                 295                 300

Thr Leu Pro Ala Pro Glu Phe Ser Pro Glu Pro Glu Ser Gly Arg Ala
305                 310                 315                 320

Leu Arg Leu Arg Cys Leu Ala Pro Leu Glu Gly Ala Arg Phe Ala Leu
                325                 330                 335

Val Arg Glu Asp Arg Gly Gly Arg Arg Val His Arg Phe Gln Ser Pro
                340                 345                 350

Ala Gly Thr Glu Ala Leu Phe Glu Leu His Asn Ile Ser Val Ala Asp
            355                 360                 365

Ser Ala Asn Tyr Ser Cys Val Tyr Val Asp Leu Lys Pro Pro Phe Gly
    370                 375                 380

Gly Ser Ala Pro Ser Glu Arg Leu Glu Leu His Val Asp Gly Pro Pro
385                 390                 395                 400

Pro Arg Pro Gln Leu Arg Ala Thr Trp Ser Gly Ala Val Leu Ala Gly
                405                 410                 415

Arg Asp Ala Val Leu Arg Cys Glu Gly Pro Ile Pro Asp Val Thr Phe
```

```
                420            425            430
Glu Leu Leu Arg Glu Gly Glu Thr Lys Ala Val Lys Thr Val Arg Thr
            435                440                445

Pro Gly Ala Ala Ala Asn Leu Glu Leu Ile Phe Val Gly Pro Gln His
    450                455                460

Ala Gly Asn Tyr Arg Cys Arg Tyr Arg Ser Trp Val Pro His Thr Phe
465                470                475                480

Glu Ser Glu Leu Ser Asp Pro Val Glu Leu Leu Val Ala Glu Ser
                485                490                495

<210> SEQ ID NO 3
<211> LENGTH: 1474
<212> TYPE: PRT
<213> ORGANISM: Homo sapiens

<400> SEQUENCE: 3

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300
```

```
Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
    370                 375                 380

Phe Ile Arg Gly Asn Glu Ala Asn Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
    530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
    610                 615                 620

Lys Asp Leu Thr Gly Phe Pro Gly Pro Leu Asn Asp Gln Asp Asn Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
```

-continued

```
                725                 730                 735
Glu Thr Trp Ile Trp Asp Leu Val Val Asn Ser Ala Gly Val Ala
                740                 745                 750
Glu Val Gly Val Thr Val Pro Asp Thr Ile Thr Glu Trp Lys Ala Gly
                755                 760                 765
Ala Phe Cys Leu Ser Glu Asp Ala Gly Leu Gly Ile Ser Ser Thr Ala
                770                 775                 780
Ser Leu Arg Ala Phe Gln Pro Phe Val Glu Leu Thr Met Pro Tyr
785                 790                 795                 800
Ser Val Ile Arg Gly Glu Ala Phe Thr Leu Lys Ala Thr Val Leu Asn
                805                 810                 815
Tyr Leu Pro Lys Cys Ile Arg Val Ser Val Gln Leu Glu Ala Ser Pro
                820                 825                 830
Ala Phe Leu Ala Val Pro Val Glu Lys Glu Gln Ala Pro His Cys Ile
                835                 840                 845
Cys Ala Asn Gly Arg Gln Thr Val Ser Trp Ala Val Thr Pro Lys Ser
                850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
                885                 890                 895
Asp Thr Val Ile Lys Pro Leu Leu Val Glu Pro Glu Gly Leu Glu Lys
                900                 905                 910
Glu Thr Thr Phe Asn Ser Leu Leu Cys Pro Ser Gly Gly Glu Val Ser
                915                 920                 925
Glu Glu Leu Ser Leu Lys Leu Pro Pro Asn Val Val Glu Glu Ser Ala
930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
                965                 970                 975
Met Val Leu Phe Ala Pro Asn Ile Tyr Val Leu Asp Tyr Leu Asn Glu
                980                 985                 990
Thr Gln Gln Leu Thr Pro Glu Ile Lys Ser Lys Ala Ile Gly Tyr Leu
                995                1000                1005
Asn Thr Gly Tyr Gln Arg Gln Leu Asn Tyr Lys His Tyr Asp Gly
                1010                1015                1020
Ser Tyr Ser Thr Phe Gly Glu Arg Tyr Gly Arg Asn Gln Gly Asn
                1025                1030                1035
Thr Trp Leu Thr Ala Phe Val Leu Lys Thr Phe Ala Gln Ala Arg
                1040                1045                1050
Ala Tyr Ile Phe Ile Asp Glu Ala His Ile Thr Gln Ala Leu Ile
                1055                1060                1065
Trp Leu Ser Gln Arg Gln Lys Asp Asn Gly Cys Phe Arg Ser Ser
                1070                1075                1080
Gly Ser Leu Leu Asn Asn Ala Ile Lys Gly Gly Val Glu Asp Glu
                1085                1090                1095
Val Thr Leu Ser Ala Tyr Ile Thr Ile Ala Leu Leu Glu Ile Pro
                1100                1105                1110
Leu Thr Val Thr His Pro Val Val Arg Asn Ala Leu Phe Cys Leu
                1115                1120                1125
Glu Ser Ala Trp Lys Thr Ala Gln Glu Gly Asp His Gly Ser His
                1130                1135                1140
```

Val Tyr Thr Lys Ala Leu Leu Ala Tyr Ala Phe Ala Leu Ala Gly
1145                1150                1155

Asn Gln Asp Lys Arg Lys Glu Val Leu Lys Ser Leu Asn Glu Glu
1160                1165                1170

Ala Val Lys Lys Asp Asn Ser Val His Trp Glu Arg Pro Gln Lys
1175                1180                1185

Pro Lys Ala Pro Val Gly His Phe Tyr Glu Pro Gln Ala Pro Ser
1190                1195                1200

Ala Glu Val Glu Met Thr Ser Tyr Val Leu Leu Ala Tyr Leu Thr
1205                1210                1215

Ala Gln Pro Ala Pro Thr Ser Glu Asp Leu Thr Ser Ala Thr Asn
1220                1225                1230

Ile Val Lys Trp Ile Thr Lys Gln Gln Asn Ala Gln Gly Gly Phe
1235                1240                1245

Ser Ser Thr Gln Asp Thr Val Val Ala Leu His Ala Leu Ser Lys
1250                1255                1260

Tyr Gly Ala Ala Thr Phe Thr Arg Thr Gly Lys Ala Ala Gln Val
1265                1270                1275

Thr Ile Gln Ser Ser Gly Thr Phe Ser Ser Lys Phe Gln Val Asp
1280                1285                1290

Asn Asn Asn Arg Leu Leu Leu Gln Gln Val Ser Leu Pro Glu Leu
1295                1300                1305

Pro Gly Glu Tyr Ser Met Lys Val Thr Gly Glu Gly Cys Val Tyr
1310                1315                1320

Leu Gln Thr Ser Leu Lys Tyr Asn Ile Leu Pro Glu Lys Glu Glu
1325                1330                1335

Phe Pro Phe Ala Leu Gly Val Gln Thr Leu Pro Gln Thr Cys Asp
1340                1345                1350

Glu Pro Lys Ala His Thr Ser Phe Gln Ile Ser Leu Ser Val Ser
1355                1360                1365

Tyr Thr Gly Ser Arg Ser Ala Ser Asn Met Ala Ile Val Asp Val
1370                1375                1380

Lys Met Val Ser Gly Phe Ile Pro Leu Lys Pro Thr Val Lys Met
1385                1390                1395

Leu Glu Arg Ser Asn His Val Ser Arg Thr Glu Val Ser Ser Asn
1400                1405                1410

His Val Leu Ile Tyr Leu Asp Lys Val Ser Asn Gln Thr Leu Ser
1415                1420                1425

Leu Phe Phe Thr Val Leu Gln Asp Val Pro Val Arg Asp Leu Lys
1430                1435                1440

Pro Ala Ile Val Lys Val Tyr Asp Tyr Tyr Glu Thr Asp Glu Phe
1445                1450                1455

Ala Ile Ala Glu Tyr Asn Ala Pro Cys Ser Lys Asp Leu Gly Asn
1460                1465                1470

Ala

<210> SEQ ID NO 4
<211> LENGTH: 423
<212> TYPE: PRT
<213> ORGANISM: Homo sapiens

<400> SEQUENCE: 4

Met Glu Arg Met Leu Pro Leu Leu Ala Leu Gly Leu Leu Ala Ala Gly
1               5                   10                  15

```
Phe Cys Pro Ala Val Leu Cys His Pro Asn Ser Pro Leu Asp Glu Glu
             20                  25                  30

Asn Leu Thr Gln Glu Asn Gln Asp Arg Gly Thr His Val Asp Leu Gly
         35                  40                  45

Leu Ala Ser Ala Asn Val Asp Phe Ala Phe Ser Leu Tyr Lys Gln Leu
 50                  55                  60

Val Leu Lys Ala Pro Asp Lys Asn Val Ile Phe Ser Pro Leu Ser Ile
 65                  70                  75                  80

Ser Thr Ala Leu Ala Phe Leu Ser Leu Gly Ala His Asn Thr Thr Leu
                 85                  90                  95

Thr Glu Ile Leu Lys Gly Leu Lys Phe Asn Leu Thr Glu Thr Ser Glu
            100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Leu Asp Ser Gln Thr Met Met Val Leu Val
        195                 200                 205

Asn Tyr Ile Phe Phe Lys Ala Lys Trp Glu Met Pro Phe Asp Pro Gln
210                 215                 220

Asp Thr His Gln Ser Arg Phe Tyr Leu Ser Lys Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Ala Val Leu Asp Val Phe Glu Glu
        355                 360                 365

Gly Thr Glu Ala Ser Ala Ala Thr Ala Val Lys Ile Thr Leu Leu Ser
370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
            420
```

```
<210> SEQ ID NO 5
<211> LENGTH: 599
<212> TYPE: PRT
<213> ORGANISM: Homo sapiens

<400> SEQUENCE: 5

Met Lys Leu Leu Lys Leu Thr Gly Phe Ile Phe Phe Leu Phe Phe Leu
1               5                   10                  15

Thr Glu Ser Leu Thr Leu Pro Thr Gln Pro Arg Asp Ile Glu Asn Phe
            20                  25                  30

Asn Ser Thr Gln Lys Phe Ile Glu Asp Asn Ile Glu Tyr Ile Thr Ile
        35                  40                  45

Ile Ala Phe Ala Gln Tyr Val Gln Glu Ala Thr Phe Glu Glu Met Glu
50                  55                  60

Lys Leu Val Lys Asp Met Val Glu Tyr Lys Asp Arg Cys Met Ala Asp
65                  70                  75                  80

Lys Thr Leu Pro Glu Cys Ser Lys Leu Pro Asn Asn Val Leu Gln Glu
                85                  90                  95

Lys Ile Cys Ala Met Glu Gly Leu Pro Gln Lys His Asn Phe Ser His
            100                 105                 110

Cys Cys Ser Lys Val Asp Ala Gln Arg Arg Leu Cys Phe Phe Tyr Asn
        115                 120                 125

Lys Lys Ser Asp Val Gly Phe Leu Pro Pro Phe Pro Thr Leu Asp Pro
130                 135                 140

Glu Glu Lys Cys Gln Ala Tyr Glu Ser Asn Arg Glu Ser Leu Leu Asn
145                 150                 155                 160

His Phe Leu Tyr Glu Val Ala Arg Arg Asn Pro Phe Val Phe Ala Pro
                165                 170                 175

Thr Leu Leu Thr Val Ala Val His Phe Glu Glu Val Ala Lys Ser Cys
            180                 185                 190

Cys Glu Glu Gln Asn Lys Val Asn Cys Leu Gln Thr Arg Ala Ile Pro
        195                 200                 205

Val Thr Gln Tyr Leu Lys Ala Phe Ser Ser Tyr Gln Lys His Val Cys
210                 215                 220

Gly Ala Leu Leu Lys Phe Gly Thr Lys Val Val His Phe Ile Tyr Ile
225                 230                 235                 240

Ala Ile Leu Ser Gln Lys Phe Pro Lys Ile Glu Phe Lys Glu Leu Ile
                245                 250                 255

Ser Leu Val Glu Asp Val Ser Ser Asn Tyr Asp Gly Cys Cys Glu Gly
            260                 265                 270

Asp Val Val Gln Cys Ile Arg Asp Thr Ser Lys Val Met Asn His Ile
        275                 280                 285

Cys Ser Lys Gln Asp Ser Ile Ser Ser Lys Ile Lys Glu Cys Cys Glu
290                 295                 300

Lys Lys Ile Pro Glu Arg Gly Gln Cys Ile Ile Asn Ser Asn Lys Asp
305                 310                 315                 320

Asp Arg Pro Lys Asp Leu Ser Leu Arg Glu Gly Lys Phe Thr Asp Ser
                325                 330                 335

Glu Asn Val Cys Gln Glu Arg Asp Ala Asp Pro Asp Thr Phe Phe Ala
            340                 345                 350

Lys Phe Thr Phe Glu Tyr Ser Arg Arg His Pro Asp Leu Ser Ile Pro
        355                 360                 365

Glu Leu Leu Arg Ile Val Gln Ile Tyr Lys Asp Leu Leu Arg Asn Cys
370                 375                 380
```

```
Cys Asn Thr Glu Asn Pro Pro Gly Cys Tyr Arg Tyr Ala Glu Asp Lys
385                 390                 395                 400

Phe Asn Glu Thr Thr Glu Lys Ser Leu Lys Met Val Gln Gln Glu Cys
            405                 410                 415

Lys His Phe Gln Asn Leu Gly Lys Asp Gly Leu Lys Tyr His Tyr Leu
        420                 425                 430

Ile Arg Leu Thr Lys Ile Ala Pro Gln Leu Ser Thr Glu Glu Leu Val
            435                 440                 445

Ser Leu Gly Glu Lys Met Val Thr Ala Phe Thr Thr Cys Cys Thr Leu
450                 455                 460

Ser Glu Glu Phe Ala Cys Val Asp Asn Leu Ala Asp Leu Val Phe Gly
465                 470                 475                 480

Glu Leu Cys Gly Val Asn Glu Asn Arg Thr Ile Asn Pro Ala Val Asp
                485                 490                 495

His Cys Cys Lys Thr Asn Phe Ala Phe Arg Arg Pro Cys Phe Glu Ser
                500                 505                 510

Leu Lys Ala Asp Lys Thr Tyr Val Pro Pro Phe Ser Gln Asp Leu
            515                 520                 525

Phe Thr Phe His Ala Asp Met Cys Gln Ser Gln Asn Glu Glu Leu Gln
530                 535                 540

Arg Lys Thr Asp Arg Phe Leu Val Asn Leu Val Lys Leu Lys His Glu
545                 550                 555                 560

Leu Thr Asp Glu Glu Leu Gln Ser Leu Phe Thr Asn Phe Ala Asn Val
                565                 570                 575

Val Asp Lys Cys Cys Lys Ala Glu Ser Pro Glu Val Cys Phe Asn Glu
                580                 585                 590

Glu Ser Pro Lys Ile Gly Asn
            595

<210> SEQ ID NO 6
<211> LENGTH: 201
<212> TYPE: PRT
<213> ORGANISM: Homo sapiens

<400> SEQUENCE: 6

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
```

```
                145                 150                 155                 160
        Glu Ala Leu Asp Cys Leu Arg Ile Pro Lys Ser Asp Val Val Tyr Thr
                        165                 170                 175

Asp Trp Lys Lys Asp Lys Cys Glu Pro Leu Glu Lys Gln His Glu Lys
                        180                 185                 190

Glu Arg Lys Gln Glu Gly Glu Ser
                        195                 200

<210> SEQ ID NO 7
<211> LENGTH: 99
<212> TYPE: PRT
<213> ORGANISM: Homo sapiens

<400> SEQUENCE: 7

Met Gln Pro Arg Val Leu Leu Val Val Ala Leu Leu Ala Leu Leu Ala
        1               5                   10                  15

Ser Ala Arg Ala Ser Glu Ala Glu Asp Ala Ser Leu Leu Ser Phe Met
                        20                  25                  30

Gln Gly Tyr Met Lys His Ala Thr Lys Thr Ala Lys Asp Ala Leu Ser
                        35                  40                  45

Ser Val Gln Glu Ser Gln Val Ala Gln Gln Ala Arg Gly Trp Val Thr
                50                  55                  60

Asp Gly Phe Ser Ser Leu Lys Asp Tyr Trp Ser Thr Val Lys Asp Lys
        65                  70                  75                  80

Phe Ser Glu Phe Trp Asp Leu Asp Pro Glu Val Arg Pro Thr Ser Ala
                        85                  90                  95

Val Ala Ala

<210> SEQ ID NO 8
<211> LENGTH: 188
<212> TYPE: PRT
<213> ORGANISM: Homo sapiens

<400> SEQUENCE: 8

Met Phe His Gln Ile Trp Ala Ala Leu Leu Tyr Phe Tyr Gly Ile Ile
        1               5                   10                  15

Leu Asn Ser Ile Tyr Gln Cys Pro Glu His Ser Gln Leu Thr Thr Leu
                        20                  25                  30

Gly Val Asp Gly Lys Glu Phe Pro Glu Val His Leu Gly Gln Trp Tyr
                        35                  40                  45

Phe Ile Ala Gly Ala Ala Pro Thr Lys Glu Glu Leu Ala Thr Phe Asp
                50                  55                  60

Pro Val Asp Asn Ile Val Phe Asn Met Ala Ala Gly Ser Ala Pro Met
        65                  70                  75                  80

Gln Leu His Leu Arg Ala Thr Ile Arg Met Lys Asp Gly Leu Cys Val
                        85                  90                  95

Pro Arg Lys Trp Ile Tyr His Leu Thr Glu Gly Ser Thr Asp Leu Arg
                        100                 105                 110

Thr Glu Gly Arg Pro Asp Met Lys Thr Glu Leu Phe Ser Ser Ser Cys
                        115                 120                 125

Pro Gly Gly Ile Met Leu Asn Glu Thr Gly Gln Gly Tyr Gln Arg Phe
                        130                 135                 140

Leu Leu Tyr Asn Arg Ser Pro His Pro Glu Lys Cys Val Glu Glu
        145                 150                 155                 160

Phe Lys Ser Leu Thr Ser Cys Leu Asp Ser Lys Ala Phe Leu Leu Thr
                        165                 170                 175
```

Pro Arg Asn Gln Glu Ala Cys Glu Leu Ser Asn Asn
            180                 185

<210> SEQ ID NO 9
<211> LENGTH: 583
<212> TYPE: PRT
<213> ORGANISM: Homo sapiens

<400> SEQUENCE: 9

Met Lys Leu Leu His Val Phe Leu Leu Phe Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
            35                  40                  45

Gln Pro Trp Gln Arg Cys Ile Glu Gly Thr Cys Val Cys Lys Leu Pro
        50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
            115                 120                 125

Val Lys Leu Val Asp Gln Asp Lys Thr Met Phe Ile Cys Lys Ser Ser
130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
            195                 200                 205

Phe Ala Asp Val Val Cys Tyr Thr Gln Lys Ala Asp Ser Pro Met Asp
        210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Thr Gln Glu Glu Thr
290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile

```
                355                 360                 365
Tyr Ile Gly Gly Cys Trp Ile Leu Thr Ala Ala His Cys Leu Arg Ala
370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
                420                 425                 430

Ile Glu Met Lys Lys Asp Gly Asn Lys Lys Asp Cys Glu Leu Pro Arg
                435                 440                 445

Ser Ile Pro Ala Cys Val Pro Trp Ser Pro Tyr Leu Phe Gln Pro Asn
                450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
                500                 505                 510

Thr Tyr Asp Gly Ser Ile Asp Ala Cys Lys Gly Asp Ser Gly Gly Pro
                515                 520                 525

Leu Val Cys Met Asp Ala Asn Asn Val Thr Tyr Val Trp Gly Val Val
                530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
                580

<210> SEQ ID NO 10
<211> LENGTH: 449
<212> TYPE: PRT
<213> ORGANISM: Homo sapiens

<400> SEQUENCE: 10

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
                35                  40                  45

Ala Val Asn Gly Val Lys Gln Ile Lys Thr Leu Ile Glu Lys Thr Asn
                50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
                100                 105                 110

Cys Lys Pro Cys Leu Lys Gln Thr Cys Met Lys Phe Tyr Ala Arg Val
                115                 120                 125

Cys Arg Ser Gly Ser Gly Leu Val Gly Arg Gln Leu Glu Glu Phe Leu
                130                 135                 140
```

```
Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
            165                 170                 175

Gln Asp His Phe Ser Arg Ala Ser Ser Ile Ile Asp Glu Leu Phe Gln
        180                 185                 190

Asp Arg Phe Phe Thr Arg Glu Pro Gln Asp Thr Tyr His Tyr Leu Pro
    195                 200                 205

Phe Ser Leu Pro His Arg Arg Pro His Phe Phe Pro Lys Ser Arg
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu

<210> SEQ ID NO 11
<211> LENGTH: 1744
<212> TYPE: PRT
<213> ORGANISM: Homo sapiens

<400> SEQUENCE: 11

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60
```

```
Asn Val Pro Cys Ser Pro Lys Val Asp Phe Thr Leu Ser Ser Glu Arg
 65                  70                  75                  80

Asp Phe Ala Leu Leu Ser Leu Gln Val Pro Leu Lys Asp Ala Lys Ser
                 85                  90                  95

Cys Gly Leu His Gln Leu Leu Arg Gly Pro Glu Val Gln Leu Val Ala
                100                 105                 110

His Ser Pro Trp Leu Lys Asp Ser Leu Ser Arg Thr Thr Asn Ile Gln
                115                 120                 125

Gly Ile Asn Leu Leu Phe Ser Arg Arg Gly His Leu Phe Leu Gln
130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
                180                 185                 190

Met Pro Ser Ser Ile Phe Gln Asp Asp Phe Val Ile Pro Asp Ile Ser
                195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
                260                 265                 270

Gly Lys Pro Val Gln Gly Val Ala Tyr Val Arg Phe Gly Leu Leu Asp
                275                 280                 285

Glu Asp Gly Lys Lys Thr Phe Phe Arg Gly Leu Glu Ser Gln Thr Lys
                290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
                340                 345                 350

Glu Glu Ala Glu Leu Thr Ser Trp Tyr Phe Val Ser Ser Pro Phe Ser
                355                 360                 365

Leu Asp Leu Ser Lys Thr Lys Arg His Leu Val Pro Gly Ala Pro Phe
                370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
                435                 440                 445

Ser Ala Gly Ser Pro His Pro Ala Ile Ala Arg Leu Thr Val Ala Ala
                450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
```

```
            485                 490                 495
Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
            530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
            565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
            610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
            645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
            805                 810                 815

Lys Gly Leu Cys Val Ala Thr Pro Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
            850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
            885                 890                 895

Val Ala Phe Ser Val Val Pro Thr Ala Ala Ala Val Ser Leu Lys
            900                 905                 910
```

-continued

```
Val Val Ala Arg Gly Ser Phe Glu Phe Pro Val Gly Asp Ala Val Ser
        915                 920                 925

Lys Val Leu Gln Ile Glu Lys Glu Gly Ala Ile His Arg Glu Glu Leu
    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
                980                 985                 990

Gly Ala Leu Ser Pro Gly Gly Val Ala Ser Leu Leu Arg Leu Pro Arg
            995                1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Asp Ser Ser Thr Trp Leu Thr Ala Phe Val Leu
    1070                1075                1080

Lys Val Leu Ser Leu Ala Gln Glu Gln Val Gly Ser Pro Glu
    1085                1090                1095

Lys Leu Gln Glu Thr Ser Asn Trp Leu Leu Ser Gln Gln Gln Ala
    1100                1105                1110

Asp Gly Ser Phe Gln Asp Pro Cys Pro Val Leu Asp Arg Ser Met
    1115                1120                1125

Gln Gly Gly Leu Val Gly Asn Asp Glu Thr Val Ala Leu Thr Ala
    1130                1135                1140

Phe Val Thr Ile Ala Leu His His Gly Leu Ala Val Phe Gln Asp
    1145                1150                1155

Glu Gly Ala Glu Pro Leu Lys Gln Arg Val Glu Ala Ser Ile Ser
    1160                1165                1170

Lys Ala Asn Ser Phe Leu Gly Glu Lys Ala Ser Ala Gly Leu Leu
    1175                1180                1185

Gly Ala His Ala Ala Ala Ile Thr Ala Tyr Ala Leu Thr Leu Thr
    1190                1195                1200

Lys Ala Pro Val Asp Leu Leu Gly Val Ala His Asn Asn Leu Met
    1205                1210                1215

Ala Met Ala Gln Glu Thr Gly Asp Asn Leu Tyr Trp Gly Ser Val
    1220                1225                1230

Thr Gly Ser Gln Ser Asn Ala Val Ser Pro Thr Pro Ala Pro Arg
    1235                1240                1245

Asn Pro Ser Asp Pro Met Pro Gln Ala Pro Ala Leu Trp Ile Glu
    1250                1255                1260

Thr Thr Ala Tyr Ala Leu Leu His Leu Leu Leu His Glu Gly Lys
    1265                1270                1275

Ala Glu Met Ala Asp Gln Ala Ser Ala Trp Leu Thr Arg Gln Gly
    1280                1285                1290

Ser Phe Gln Gly Gly Phe Arg Ser Thr Gln Asp Thr Val Ile Ala
    1295                1300                1305
```

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Asp Tyr Glu Tyr Asp Glu Leu Pro Ala Lys
1415                1420                1425

Asp Asp Pro Asp Ala Pro Leu Gln Pro Val Thr Pro Leu Gln Leu
1430                1435                1440

Phe Glu Gly Arg Arg Asn Arg Arg Arg Arg Glu Ala Pro Lys Val
1445                1450                1455

Val Glu Glu Gln Glu Ser Arg Val His Tyr Thr Val Cys Ile Trp
1460                1465                1470

Arg Asn Gly Lys Val Gly Leu Ser Gly Met Ala Ile Ala Asp Val
1475                1480                1485

Thr Leu Leu Ser Gly Phe His Ala Leu Arg Ala Asp Leu Glu Lys
1490                1495                1500

Leu Thr Ser Leu Ser Asp Arg Tyr Val Ser His Phe Glu Thr Glu
1505                1510                1515

Gly Pro His Val Leu Leu Tyr Phe Asp Ser Val Pro Thr Ser Arg
1520                1525                1530

Glu Cys Val Gly Phe Glu Ala Val Gln Glu Val Pro Val Gly Leu
1535                1540                1545

Val Gln Pro Ala Ser Ala Thr Leu Tyr Asp Tyr Tyr Asn Pro Glu
1550                1555                1560

Arg Arg Cys Ser Val Phe Tyr Gly Ala Pro Ser Lys Ser Arg Leu
1565                1570                1575

Leu Ala Thr Leu Cys Ser Ala Glu Val Cys Gln Cys Ala Glu Gly
1580                1585                1590

Lys Cys Pro Arg Gln Arg Arg Ala Leu Glu Arg Gly Leu Gln Asp
1595                1600                1605

Glu Asp Gly Tyr Arg Met Lys Phe Ala Cys Tyr Tyr Pro Arg Val
1610                1615                1620

Glu Tyr Gly Phe Gln Val Lys Val Leu Arg Glu Asp Ser Arg Ala
1625                1630                1635

Ala Phe Arg Leu Phe Glu Thr Lys Ile Thr Gln Val Leu His Phe
1640                1645                1650

Thr Lys Asp Val Lys Ala Ala Asn Gln Met Arg Asn Phe Leu
1655                1660                1665

Val Arg Ala Ser Cys Arg Leu Arg Leu Glu Pro Gly Lys Glu Tyr
1670                1675                1680

Leu Ile Met Gly Leu Asp Gly Ala Thr Tyr Asp Leu Glu Gly His
1685                1690                1695

Pro Gln Tyr Leu Leu Asp Ser Asn Ser Trp Ile Glu Glu Met Pro

-continued

```
                1700                1705                1710

Ser Glu Arg Leu Cys Arg Ser Thr Arg Gln Arg Ala Ala Cys Ala
        1715                1720                1725

Gln Leu Asn Asp Phe Leu Gln Glu Tyr Gly Thr Gln Gly Cys Gln
        1730                1735                1740

Val

<210> SEQ ID NO 12
<211> LENGTH: 934
<212> TYPE: PRT
<213> ORGANISM: Homo sapiens

<400> SEQUENCE: 12

Met Ala Arg Arg Ser Val Leu Tyr Phe Ile Leu Leu Asn Ala Leu Ile
1               5                   10                  15

Asn Lys Gly Gln Ala Cys Phe Cys Asp His Tyr Ala Trp Thr Gln Trp
            20                  25                  30

Thr Ser Cys Ser Lys Thr Cys Asn Ser Gly Thr Gln Ser Arg His Arg
        35                  40                  45

Gln Ile Val Val Asp Lys Tyr Tyr Gln Glu Asn Phe Cys Glu Gln Ile
    50                  55                  60

Cys Ser Lys Gln Glu Thr Arg Glu Cys Asn Trp Gln Arg Cys Pro Ile
65                  70                  75                  80

Asn Cys Leu Leu Gly Asp Phe Gly Pro Trp Ser Asp Cys Asp Pro Cys
                85                  90                  95

Ile Glu Lys Gln Ser Lys Val Arg Ser Val Leu Arg Pro Ser Gln Phe
            100                 105                 110

Gly Gly Gln Pro Cys Thr Ala Pro Leu Val Ala Phe Gln Pro Cys Ile
        115                 120                 125

Pro Ser Lys Leu Cys Lys Ile Glu Glu Ala Asp Cys Lys Asn Lys Phe
    130                 135                 140

Arg Cys Asp Ser Gly Arg Cys Ile Ala Arg Lys Leu Glu Cys Asn Gly
145                 150                 155                 160

Glu Asn Asp Cys Gly Asp Asn Ser Asp Glu Arg Asp Cys Gly Arg Thr
                165                 170                 175

Lys Ala Val Cys Thr Arg Lys Tyr Asn Pro Ile Pro Ser Val Gln Leu
            180                 185                 190

Met Gly Asn Gly Phe His Phe Leu Ala Gly Glu Pro Arg Gly Glu Val
        195                 200                 205

Leu Asp Asn Ser Phe Thr Gly Gly Ile Cys Lys Thr Val Lys Ser Ser
    210                 215                 220

Arg Thr Ser Asn Pro Tyr Arg Val Pro Ala Asn Leu Glu Asn Val Gly
225                 230                 235                 240

Phe Glu Val Gln Thr Ala Glu Asp Asp Leu Lys Thr Asp Phe Tyr Lys
                245                 250                 255

Asp Leu Thr Ser Leu Gly His Asn Glu Asn Gln Gln Gly Ser Phe Ser
            260                 265                 270

Ser Gln Gly Gly Ser Ser Phe Ser Val Pro Ile Phe Tyr Ser Ser Lys
        275                 280                 285

Arg Ser Glu Asn Ile Asn His Asn Ser Ala Phe Lys Gln Ala Ile Gln
    290                 295                 300

Ala Ser His Lys Lys Asp Ser Ser Phe Ile Arg Ile His Lys Val Met
305                 310                 315                 320

Lys Val Leu Asn Phe Thr Thr Lys Ala Lys Asp Leu His Leu Ser Asp
```

```
                    325                 330                 335
Val Phe Leu Lys Ala Leu Asn His Leu Pro Leu Glu Tyr Asn Ser Ala
                340                 345                 350
Leu Tyr Ser Arg Ile Phe Asp Asp Phe Gly Thr His Tyr Phe Thr Ser
                355                 360                 365
Gly Ser Leu Gly Gly Val Tyr Asp Leu Leu Tyr Gln Phe Ser Ser Glu
            370                 375                 380
Glu Leu Lys Asn Ser Gly Leu Thr Glu Glu Ala Lys His Cys Val
385                 390                 395                 400
Arg Ile Glu Thr Lys Lys Arg Val Leu Phe Ala Lys Lys Thr Lys Val
                405                 410                 415
Glu His Arg Cys Thr Thr Asn Lys Leu Ser Glu Lys His Glu Gly Ser
                420                 425                 430
Phe Ile Gln Gly Ala Glu Lys Ser Ile Ser Leu Ile Arg Gly Gly Arg
                435                 440                 445
Ser Glu Tyr Gly Ala Ala Leu Ala Trp Glu Lys Gly Ser Ser Gly Leu
            450                 455                 460
Glu Glu Lys Thr Phe Ser Glu Trp Leu Glu Ser Val Lys Glu Asn Pro
465                 470                 475                 480
Ala Val Ile Asp Phe Glu Leu Ala Pro Ile Val Asp Leu Val Arg Asn
                485                 490                 495
Ile Pro Cys Ala Val Thr Lys Arg Asn Asn Leu Arg Lys Ala Leu Gln
                500                 505                 510
Glu Tyr Ala Ala Lys Phe Asp Pro Cys Gln Cys Ala Pro Cys Pro Asn
                515                 520                 525
Asn Gly Arg Pro Thr Leu Ser Gly Thr Glu Cys Leu Cys Val Cys Gln
            530                 535                 540
Ser Gly Thr Tyr Gly Glu Asn Cys Glu Lys Gln Ser Pro Asp Tyr Lys
545                 550                 555                 560
Ser Asn Ala Val Asp Gly Gln Trp Gly Cys Trp Ser Ser Trp Ser Thr
                565                 570                 575
Cys Asp Ala Thr Tyr Lys Arg Ser Arg Thr Arg Glu Cys Asn Asn Pro
                580                 585                 590
Ala Pro Gln Arg Gly Gly Lys Arg Cys Glu Gly Glu Lys Arg Gln Glu
            595                 600                 605
Glu Asp Cys Thr Phe Ser Ile Met Glu Asn Asn Gly Gln Pro Cys Ile
            610                 615                 620
Asn Asp Asp Glu Glu Met Lys Glu Val Asp Leu Pro Glu Ile Glu Ala
625                 630                 635                 640
Asp Ser Gly Cys Pro Gln Pro Val Pro Pro Glu Asn Gly Phe Ile Arg
                645                 650                 655
Asn Glu Lys Gln Leu Tyr Leu Val Gly Glu Asp Val Glu Ile Ser Cys
            660                 665                 670
Leu Thr Gly Phe Glu Thr Val Gly Tyr Gln Tyr Phe Arg Cys Leu Pro
            675                 680                 685
Asp Gly Thr Trp Arg Gln Gly Asp Val Glu Cys Gln Arg Thr Glu Cys
            690                 695                 700
Ile Lys Pro Val Val Gln Glu Val Leu Thr Ile Thr Pro Phe Gln Arg
705                 710                 715                 720
Leu Tyr Arg Ile Gly Glu Ser Ile Glu Leu Thr Cys Pro Lys Gly Phe
                725                 730                 735
Val Val Ala Gly Pro Ser Arg Tyr Thr Cys Gln Gly Asn Ser Trp Thr
            740                 745                 750
```

Pro Pro Ile Ser Asn Ser Leu Thr Cys Glu Lys Asp Thr Leu Thr Lys
        755                 760                 765

Leu Lys Gly His Cys Gln Leu Gly Gln Lys Gln Ser Gly Ser Glu Cys
    770                 775                 780

Ile Cys Met Ser Pro Glu Glu Asp Cys Ser His His Ser Glu Asp Leu
785                 790                 795                 800

Cys Val Phe Asp Thr Asp Ser Asn Asp Tyr Phe Thr Ser Pro Ala Cys
                805                 810                 815

Lys Phe Leu Ala Glu Lys Cys Leu Asn Asn Gln Gln Leu His Phe Leu
                820                 825                 830

His Ile Gly Ser Cys Gln Asp Gly Arg Gln Leu Glu Trp Gly Leu Glu
                835                 840                 845

Arg Thr Arg Leu Ser Ser Asn Ser Thr Lys Lys Glu Ser Cys Gly Tyr
    850                 855                 860

Asp Thr Cys Tyr Asp Trp Glu Lys Cys Ser Ala Ser Thr Ser Lys Cys
865                 870                 875                 880

Val Cys Leu Leu Pro Pro Gln Cys Phe Lys Gly Gly Asn Gln Leu Tyr
                885                 890                 895

Cys Val Lys Met Gly Ser Ser Thr Ser Glu Lys Thr Leu Asn Ile Cys
                900                 905                 910

Glu Val Gly Thr Ile Arg Cys Ala Asn Arg Lys Met Glu Ile Leu His
                915                 920                 925

Pro Gly Lys Cys Leu Ala
    930

<210> SEQ ID NO 13
<211> LENGTH: 584
<212> TYPE: PRT
<213> ORGANISM: Homo sapiens

<400> SEQUENCE: 13

Met Phe Ala Val Val Phe Phe Ile Leu Ser Leu Met Thr Cys Gln Pro
1               5                   10                  15

Gly Val Thr Ala Gln Glu Lys Val Asn Gln Arg Val Arg Arg Ala Ala
                20                  25                  30

Thr Pro Ala Ala Val Thr Cys Gln Leu Ser Asn Trp Ser Glu Trp Thr
            35                  40                  45

Asp Cys Phe Pro Cys Gln Asp Lys Lys Tyr Arg His Arg Ser Leu Leu
    50                  55                  60

Gln Pro Asn Lys Phe Gly Gly Thr Ile Cys Ser Gly Asp Ile Trp Asp
65                  70                  75                  80

Gln Ala Ser Cys Ser Ser Ser Thr Thr Cys Val Arg Gln Ala Gln Cys
                85                  90                  95

Gly Gln Asp Phe Gln Cys Lys Glu Thr Gly Arg Cys Leu Lys Arg His
                100                 105                 110

Leu Val Cys Asn Gly Asp Gln Asp Cys Leu Asp Gly Ser Asp Glu Asp
            115                 120                 125

Asp Cys Glu Asp Val Arg Ala Ile Asp Glu Asp Cys Ser Gln Tyr Glu
    130                 135                 140

Pro Ile Pro Gly Ser Gln Lys Ala Ala Leu Gly Tyr Asn Ile Leu Thr
145                 150                 155                 160

Gln Glu Asp Ala Gln Ser Val Tyr Asp Ala Ser Tyr Tyr Gly Gly Gln
                165                 170                 175

Cys Glu Thr Val Tyr Asn Gly Glu Trp Arg Glu Leu Arg Tyr Asp Ser

```
            180             185             190
Thr Cys Glu Arg Leu Tyr Tyr Gly Asp Asp Glu Lys Tyr Phe Arg Lys
        195                 200                 205
Pro Tyr Asn Phe Leu Lys Tyr His Phe Glu Ala Leu Ala Asp Thr Gly
    210                 215                 220
Ile Ser Ser Glu Phe Tyr Asp Asn Ala Asn Asp Leu Leu Ser Lys Val
225                 230                 235                 240
Lys Lys Asp Lys Ser Asp Ser Phe Gly Val Thr Ile Gly Ile Gly Pro
                245                 250                 255
Ala Gly Ser Pro Leu Leu Val Gly Val Gly Val Ser His Ser Gln Asp
            260                 265                 270
Thr Ser Phe Leu Asn Glu Leu Asn Lys Tyr Asn Glu Lys Lys Phe Ile
        275                 280                 285
Phe Thr Arg Ile Phe Thr Lys Val Gln Thr Ala His Phe Lys Met Arg
    290                 295                 300
Lys Asp Asp Ile Met Leu Asp Glu Gly Met Leu Gln Ser Leu Met Glu
305                 310                 315                 320
Leu Pro Asp Gln Tyr Asn Tyr Gly Met Tyr Ala Lys Phe Ile Asn Asp
                325                 330                 335
Tyr Gly Thr His Tyr Ile Thr Ser Gly Ser Met Gly Gly Ile Tyr Glu
            340                 345                 350
Tyr Ile Leu Val Ile Asp Lys Ala Lys Met Glu Ser Leu Gly Ile Thr
        355                 360                 365
Ser Arg Asp Ile Thr Thr Cys Phe Gly Gly Ser Leu Gly Ile Gln Tyr
    370                 375                 380
Glu Asp Lys Ile Asn Val Gly Gly Gly Leu Ser Gly Asp His Cys Lys
385                 390                 395                 400
Lys Phe Gly Gly Gly Lys Thr Glu Arg Ala Arg Lys Ala Met Ala Val
                405                 410                 415
Glu Asp Ile Ile Ser Arg Val Arg Gly Gly Ser Ser Gly Trp Ser Gly
            420                 425                 430
Gly Leu Ala Gln Asn Arg Ser Thr Ile Thr Tyr Arg Ser Trp Gly Arg
        435                 440                 445
Ser Leu Lys Tyr Asn Pro Val Val Ile Asp Phe Glu Met Gln Pro Ile
    450                 455                 460
His Glu Val Leu Arg His Thr Ser Leu Gly Pro Leu Glu Ala Lys Arg
465                 470                 475                 480
Gln Asn Leu Arg Arg Ala Leu Asp Gln Tyr Leu Met Glu Phe Asn Ala
                485                 490                 495
Cys Arg Cys Gly Pro Cys Phe Asn Asn Gly Val Pro Ile Leu Glu Gly
            500                 505                 510
Thr Ser Cys Arg Cys Gln Cys Arg Leu Gly Ser Leu Gly Ala Ala Cys
        515                 520                 525
Glu Gln Thr Gln Thr Glu Gly Ala Lys Ala Asp Gly Ser Trp Ser Cys
    530                 535                 540
Trp Ser Ser Trp Ser Val Cys Arg Ala Gly Ile Gln Glu Arg Arg Arg
545                 550                 555                 560
Glu Cys Asp Asn Pro Ala Pro Gln Asn Gly Gly Ala Ser Cys Pro Gly
                565                 570                 575
Arg Lys Val Gln Thr Gln Ala Cys
            580

<210> SEQ ID NO 14
```

```
<211> LENGTH: 406
<212> TYPE: PRT
<213> ORGANISM: Homo sapiens

<400> SEQUENCE: 14

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
    370                 375                 380

Glu Tyr Gly Val Tyr Val Lys Val Thr Ser Ile Gln Asp Trp Val Gln
```

```
385             390             395             400
Lys Thr Ile Ala Glu Asn
                405
```

<210> SEQ ID NO 15
<211> LENGTH: 340
<212> TYPE: PRT
<213> ORGANISM: Homo sapiens

<400> SEQUENCE: 15

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Glu Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340
```

<210> SEQ ID NO 16
<211> LENGTH: 330
<212> TYPE: PRT
<213> ORGANISM: Homo sapiens

<400> SEQUENCE: 16

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 17
<211> LENGTH: 326
<212> TYPE: PRT
<213> ORGANISM: Homo sapiens

<400> SEQUENCE: 17

-continued

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 18
<211> LENGTH: 453
<212> TYPE: PRT
<213> ORGANISM: Homo sapiens

<400> SEQUENCE: 18

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45
```

```
Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450
```

<210> SEQ ID NO 19
<211> LENGTH: 638
<212> TYPE: PRT
<213> ORGANISM: Homo sapiens

<400> SEQUENCE: 19

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
        115                 120                 125

Ser Lys Val Ser Ser Val Glu Glu Cys Gln Lys Arg Cys Thr Asn Asn
130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
    210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Ser Thr Pro Gln
            260                 265                 270

Glu Asn Thr Ile Ser Gly Tyr Ser Leu Leu Thr Cys Lys Arg Thr Leu
        275                 280                 285

Pro Glu Pro Cys His Ser Lys Ile Tyr Pro Gly Val Asp Phe Gly Gly
    290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Glu Cys Lys Cys Phe Leu Arg Leu Ser
            340                 345                 350

Met Asp Gly Ser Pro Thr Arg Ile Ala Tyr Gly Thr Gln Gly Ser Ser
        355                 360                 365

Gly Tyr Ser Leu Arg Leu Cys Asn Thr Gly Asp Asn Ser Val Cys Thr
    370                 375                 380

-continued

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
            405                 410                 415

His Leu Cys Gly Gly Ser Leu Ile Gly His Gln Trp Val Leu Thr Ala
        420                 425                 430

Ala His Cys Phe Asp Gly Leu Pro Leu Gln Asp Val Trp Arg Ile Tyr
    435                 440                 445

Ser Gly Ile Leu Asn Leu Ser Asp Ile Thr Lys Asp Thr Pro Phe Ser
450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
        515                 520                 525

Gly Glu Ile Gln Asn Ile Leu Gln Lys Val Asn Ile Pro Leu Val Thr
    530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
    610                 615                 620

Thr Gln Ser Ser Asp Gly Lys Ala Gln Met Gln Ser Pro Ala
625                 630                 635

<210> SEQ ID NO 20
<211> LENGTH: 698
<212> TYPE: PRT
<213> ORGANISM: Homo sapiens

<400> SEQUENCE: 20

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met

```
            115                 120                 125
Asn Gln Leu Arg Gly Lys Lys Ser Cys His Thr Gly Leu Gly Arg Ser
            130                 135                 140
Ala Gly Trp Asn Ile Pro Ile Gly Leu Leu Tyr Cys Asp Leu Pro Glu
145                 150                 155                 160
Pro Arg Lys Pro Leu Glu Lys Ala Val Ala Asn Phe Phe Ser Gly Ser
                165                 170                 175
Cys Ala Pro Cys Ala Asp Gly Thr Asp Phe Pro Gln Leu Cys Gln Leu
            180                 185                 190
Cys Pro Gly Cys Gly Cys Ser Thr Leu Asn Gln Tyr Phe Gly Tyr Ser
            195                 200                 205
Gly Ala Phe Lys Cys Leu Lys Asp Gly Ala Gly Asp Val Ala Phe Val
            210                 215                 220
Lys His Ser Thr Ile Phe Glu Asn Leu Ala Asn Lys Ala Asp Arg Asp
225                 230                 235                 240
Gln Tyr Glu Leu Leu Cys Leu Asp Asn Thr Arg Lys Pro Val Asp Glu
                245                 250                 255
Tyr Lys Asp Cys His Leu Ala Gln Val Pro Ser His Thr Val Val Ala
            260                 265                 270
Arg Ser Met Gly Gly Lys Glu Asp Leu Ile Trp Glu Leu Leu Asn Gln
            275                 280                 285
Ala Gln Glu His Phe Gly Lys Asp Lys Ser Lys Glu Phe Gln Leu Phe
            290                 295                 300
Ser Ser Pro His Gly Lys Asp Leu Leu Phe Lys Asp Ser Ala His Gly
305                 310                 315                 320
Phe Leu Lys Val Pro Pro Arg Met Asp Ala Lys Met Tyr Leu Gly Tyr
                325                 330                 335
Glu Tyr Val Thr Ala Ile Arg Asn Leu Arg Glu Gly Thr Cys Pro Glu
            340                 345                 350
Ala Pro Thr Asp Glu Cys Lys Pro Val Lys Trp Cys Ala Leu Ser His
            355                 360                 365
His Glu Arg Leu Lys Cys Asp Glu Trp Ser Val Asn Ser Val Gly Lys
            370                 375                 380
Ile Glu Cys Val Ser Ala Glu Thr Thr Glu Asp Cys Ile Ala Lys Ile
385                 390                 395                 400
Met Asn Gly Glu Ala Asp Ala Met Ser Leu Asp Gly Gly Phe Val Tyr
                405                 410                 415
Ile Ala Gly Lys Cys Gly Leu Val Pro Val Leu Ala Glu Asn Tyr Asn
            420                 425                 430
Lys Ser Asp Asn Cys Glu Asp Thr Pro Glu Ala Gly Tyr Phe Ala Ile
            435                 440                 445
Ala Val Val Lys Lys Ser Ala Ser Asp Leu Thr Trp Asp Asn Leu Lys
            450                 455                 460
Gly Lys Lys Ser Cys His Thr Ala Val Gly Arg Thr Ala Gly Trp Asn
465                 470                 475                 480
Ile Pro Met Gly Leu Leu Tyr Asn Lys Ile Asn His Cys Arg Phe Asp
                485                 490                 495
Glu Phe Phe Ser Glu Gly Cys Ala Pro Gly Ser Lys Lys Asp Ser Ser
            500                 505                 510
Leu Cys Lys Leu Cys Met Gly Ser Gly Leu Asn Leu Cys Glu Pro Asn
            515                 520                 525
Asn Lys Glu Gly Tyr Tyr Gly Tyr Thr Gly Ala Phe Arg Cys Leu Val
            530                 535                 540
```

-continued

```
Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
            565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
            645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
690                 695

<210> SEQ ID NO 21
<211> LENGTH: 478
<212> TYPE: PRT
<213> ORGANISM: Homo sapiens

<400> SEQUENCE: 21

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
            115                 120                 125

Ala Ser Lys Pro Glu Gly Ile Asp Ser Arg Pro Glu Thr Leu His Pro
130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
            165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
            195                 200                 205

Ala Phe Thr Arg Ile Asn Cys Gln Gly Lys Thr Tyr Leu Phe Lys Gly
```

```
                210                 215                 220
Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Arg Ser Gln Arg Gly
    370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Gly Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Ser Gly Asp Lys Tyr Tyr Arg Val Asn
        435                 440                 445

Leu Arg Thr Arg Arg Val Asp Thr Val Asp Pro Pro Tyr Pro Arg Ser
    450                 455                 460

Ile Ala Gln Tyr Trp Leu Gly Cys Pro Ala Pro Gly His Leu
465                 470                 475

<210> SEQ ID NO 22
<211> LENGTH: 298
<212> TYPE: PRT
<213> ORGANISM: Homo sapiens

<400> SEQUENCE: 22

Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
                20                  25                  30

Ile Tyr Thr Gly Leu Ser Lys His Val Glu Asp Val Pro Ala Phe Gln
            35                  40                  45

Ala Leu Gly Ser Leu Asn Asp Leu Gln Phe Phe Arg Tyr Asn Ser Lys
        50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110
```

```
Gly Ser His Val Leu Gln Gly Arg Phe Gly Cys Glu Ile Glu Asn Asn
            115                 120                 125

Arg Ser Ser Gly Ala Phe Trp Lys Tyr Tyr Asp Gly Lys Asp Tyr
130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Glu Cys Pro Ala Thr Leu Arg Lys
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Lys Leu Lys
    210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser
    290                 295

<210> SEQ ID NO 23
<211> LENGTH: 16
<212> TYPE: PRT
<213> ORGANISM: Homo sapiens

<400> SEQUENCE: 23

Tyr Leu Gly Asn Ala Thr Ala Ile Phe Phe Leu Pro Asp Glu Gly Lys
1               5                   10                  15

<210> SEQ ID NO 24
<211> LENGTH: 33
<212> TYPE: PRT
<213> ORGANISM: Homo sapiens

<400> SEQUENCE: 24

Glu Gly Asp His Glu Phe Leu Glu Val Pro Glu Ala Gln Glu Asp Val
1               5                   10                  15

Glu Ala Thr Phe Pro Val His Gln Pro Gly Asn Tyr Ser Cys Ser Tyr
            20                  25                  30

Arg

<210> SEQ ID NO 25
<211> LENGTH: 11
<212> TYPE: PRT
<213> ORGANISM: Homo sapiens

<400> SEQUENCE: 25

Ala Ile Gly Tyr Leu Asn Thr Gly Tyr Gln Arg
1               5                   10

<210> SEQ ID NO 26
<211> LENGTH: 14
<212> TYPE: PRT
<213> ORGANISM: Homo sapiens
```

<400> SEQUENCE: 26

Thr Glu His Pro Phe Thr Val Glu Glu Phe Val Leu Pro Lys
1               5                   10

<210> SEQ ID NO 27
<211> LENGTH: 19
<212> TYPE: PRT
<213> ORGANISM: Homo sapiens

<400> SEQUENCE: 27

Val Ser Asn Gln Thr Leu Ser Leu Phe Phe Thr Val Leu Gln Asp Val
1               5                   10                  15

Pro Val Arg

<210> SEQ ID NO 28
<211> LENGTH: 33
<212> TYPE: PRT
<213> ORGANISM: Homo sapiens

<400> SEQUENCE: 28

Ile Ile Thr Ile Leu Glu Glu Glu Met Asn Val Ser Val Cys Gly Leu
1               5                   10                  15

Tyr Thr Tyr Gly Lys Pro Val Pro Gly His Val Thr Val Ser Ile Cys
                20                  25                  30

Arg

<210> SEQ ID NO 29
<211> LENGTH: 22
<212> TYPE: PRT
<213> ORGANISM: Homo sapiens

<400> SEQUENCE: 29

Gly Cys Val Leu Leu Ser Tyr Leu Asn Glu Thr Val Thr Val Ser Ala
1               5                   10                  15

Ser Leu Glu Ser Val Arg
                20

<210> SEQ ID NO 30
<211> LENGTH: 32
<212> TYPE: PRT
<213> ORGANISM: Homo sapiens

<400> SEQUENCE: 30

Ser Leu Gly Asn Val Asn Phe Thr Val Ser Ala Glu Ala Leu Glu Ser
1               5                   10                  15

Gln Glu Leu Cys Gly Thr Glu Val Pro Ser Val Pro Glu His Gly Arg
                20                  25                  30

<210> SEQ ID NO 31
<211> LENGTH: 56
<212> TYPE: PRT
<213> ORGANISM: Homo sapiens

<400> SEQUENCE: 31

Ala Ser Val Ser Val Leu Gly Asp Ile Leu Gly Ser Ala Met Gln Asn
1               5                   10                  15

Thr Gln Asn Leu Leu Gln Met Pro Tyr Gly Cys Gly Glu Gln Asn Met
                20                  25                  30

Val Leu Phe Ala Pro Asn Ile Tyr Val Leu Asp Tyr Leu Asn Glu Thr
                35                  40                  45

```
Gln Gln Leu Thr Pro Glu Ile Lys
    50                  55

<210> SEQ ID NO 32
<211> LENGTH: 20
<212> TYPE: PRT
<213> ORGANISM: Homo sapiens

<400> SEQUENCE: 32

Phe Asn Leu Thr Glu Thr Ser Glu Ala Glu Ile His Gln Ser Phe Gln
1               5                   10                  15

His Leu Leu Arg
            20

<210> SEQ ID NO 33
<211> LENGTH: 10
<212> TYPE: PRT
<213> ORGANISM: Homo sapiens

<400> SEQUENCE: 33

Asp Ile Glu Asn Phe Asn Ser Thr Gln Lys
1               5                   10

<210> SEQ ID NO 34
<211> LENGTH: 24
<212> TYPE: PRT
<213> ORGANISM: Homo sapiens

<400> SEQUENCE: 34

Gln Ile Pro Leu Cys Ala Asn Leu Val Pro Val Pro Ile Thr Asn Ala
1               5                   10                  15

Thr Leu Asp Gln Ile Thr Gly Lys
            20

<210> SEQ ID NO 35
<211> LENGTH: 15
<212> TYPE: PRT
<213> ORGANISM: Homo sapiens

<400> SEQUENCE: 35

Gln Asp Gln Cys Ile Tyr Asn Thr Thr Tyr Leu Asn Val Gln Arg
1               5                   10                  15

<210> SEQ ID NO 36
<211> LENGTH: 19
<212> TYPE: PRT
<213> ORGANISM: Homo sapiens

<400> SEQUENCE: 36

Phe Ser Glu Phe Trp Asp Leu Asp Pro Glu Val Arg Pro Thr Ser Ala
1               5                   10                  15

Val Ala Ala

<210> SEQ ID NO 37
<211> LENGTH: 23
<212> TYPE: PRT
<213> ORGANISM: Homo sapiens

<400> SEQUENCE: 37

Thr Glu Leu Phe Ser Ser Ser Cys Pro Gly Gly Ile Met Leu Asn Glu
1               5                   10                  15

Thr Gly Gln Gly Tyr Gln Arg
```

```
<210> SEQ ID NO 38
<211> LENGTH: 10
<212> TYPE: PRT
<213> ORGANISM: Homo sapiens

<400> SEQUENCE: 38

Asn Gly Thr Ala Val Cys Ala Thr Asn Arg
1               5                   10

<210> SEQ ID NO 39
<211> LENGTH: 14
<212> TYPE: PRT
<213> ORGANISM: Homo sapiens

<400> SEQUENCE: 39

Leu Ala Asn Leu Thr Gln Gly Glu Asp Gln Tyr Tyr Leu Arg
1               5                   10

<210> SEQ ID NO 40
<211> LENGTH: 11
<212> TYPE: PRT
<213> ORGANISM: Homo sapiens

<400> SEQUENCE: 40

Gly Leu Asn Val Thr Leu Ser Ser Thr Gly Arg
1               5                   10

<210> SEQ ID NO 41
<211> LENGTH: 7
<212> TYPE: PRT
<213> ORGANISM: Homo sapiens

<400> SEQUENCE: 41

Val Leu Asn Phe Thr Thr Lys
1               5

<210> SEQ ID NO 42
<211> LENGTH: 14
<212> TYPE: PRT
<213> ORGANISM: Homo sapiens

<400> SEQUENCE: 42

Gly Gly Ser Ser Gly Trp Ser Gly Gly Leu Ala Gln Asn Arg
1               5                   10

<210> SEQ ID NO 43
<211> LENGTH: 13
<212> TYPE: PRT
<213> ORGANISM: Homo sapiens

<400> SEQUENCE: 43

Asn Leu Phe Leu Asn His Ser Glu Asn Ala Thr Ala Lys
1               5                   10

<210> SEQ ID NO 44
<211> LENGTH: 16
<212> TYPE: PRT
<213> ORGANISM: Homo sapiens

<400> SEQUENCE: 44

Val Val Leu His Pro Asn Tyr Ser Gln Val Asp Ile Gly Leu Ile Lys
1               5                   10                  15
```

```
<210> SEQ ID NO 45
<211> LENGTH: 9
<212> TYPE: PRT
<213> ORGANISM: Homo sapiens

<400> SEQUENCE: 45

Thr Pro Leu Thr Ala Asn Ile Thr Lys
1               5

<210> SEQ ID NO 46
<211> LENGTH: 9
<212> TYPE: PRT
<213> ORGANISM: Homo sapiens

<400> SEQUENCE: 46

Glu Glu Gln Tyr Asn Ser Thr Tyr Arg
1               5

<210> SEQ ID NO 47
<211> LENGTH: 9
<212> TYPE: PRT
<213> ORGANISM: Homo sapiens

<400> SEQUENCE: 47

Glu Glu Gln Phe Asn Ser Thr Phe Arg
1               5

<210> SEQ ID NO 48
<211> LENGTH: 21
<212> TYPE: PRT
<213> ORGANISM: Homo sapiens

<400> SEQUENCE: 48

Gly Leu Thr Phe Gln Gln Asn Ala Ser Ser Met Cys Val Pro Asp Gln
1               5                   10                  15

Asp Thr Ala Ile Arg
            20

<210> SEQ ID NO 49
<211> LENGTH: 19
<212> TYPE: PRT
<213> ORGANISM: Homo sapiens

<400> SEQUENCE: 49

Leu Gln Ala Pro Leu Asn Tyr Thr Glu Phe Gln Lys Pro Ile Cys Leu
1               5                   10                  15

Pro Ser Lys

<210> SEQ ID NO 50
<211> LENGTH: 13
<212> TYPE: PRT
<213> ORGANISM: Homo sapiens

<400> SEQUENCE: 50

Cys Gly Leu Val Pro Val Leu Ala Glu Asn Tyr Asn Lys
1               5                   10

<210> SEQ ID NO 51
<211> LENGTH: 8
<212> TYPE: PRT
<213> ORGANISM: Homo sapiens

<400> SEQUENCE: 51
```

```
Asn Gly Ser Leu Phe Ala Phe Arg
1               5

<210> SEQ ID NO 52
<211> LENGTH: 18
<212> TYPE: PRT
<213> ORGANISM: Homo sapiens

<400> SEQUENCE: 52

Asp Ile Val Glu Tyr Tyr Asn Asp Ser Asn Gly Ser His Val Leu Gln
1               5                   10                  15

Gly Arg

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Cys Asp Met His Tyr Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE
<221> NAME/KEY: MOD_RES
<222> LOCATION: (2)..(2)
<223> OTHER INFORMATION: Alkylated-Cys

<400> SEQUENCE: 54

Glu Cys Asp Met His Tyr Lys
1               5
```